US006825213B2

(12) United States Patent
Feller et al.

(10) Patent No.: US 6,825,213 B2
(45) Date of Patent: Nov. 30, 2004

(54) β₃-ADRENORECEPTOR AGONISTS, AGONIST COMPOSITIONS AND METHODS OF USING

(75) Inventors: Dennis R. Feller, Oxford, MS (US); Duane D. Miller, Germantown, TN (US)

(73) Assignee: Molecular Design International, Inc., Memphis, TN (US)

(*) Notice: Subject to any disclaimer, the term of this patent is extended or adjusted under 35 U.S.C. 154(b) by 0 days.

(21) Appl. No.: 10/603,678

(22) Filed: Jun. 25, 2003

(65) Prior Publication Data

US 2004/0019079 A1 Jan. 29, 2004

Related U.S. Application Data

(63) Continuation of application No. 09/164,047, filed on Sep. 30, 1998, now abandoned.
(60) Provisional application No. 60/061,152, filed on Sep. 30, 1997.

(51) Int. Cl.⁷ ...................... A61K 31/47; C07D 217/20; C07D 217/18
(52) U.S. Cl. ...................... 514/307; 514/309; 546/141; 546/145; 546/146; 546/147; 546/149
(58) Field of Search ................................ 546/141, 145, 546/146, 147, 149; 514/307, 309

(56) References Cited

U.S. PATENT DOCUMENTS

| | | | |
|---|---|---|---|
| 3,337,539 A | 8/1967 | Mészáros et al. |
| 3,438,989 A | 4/1969 | Shavel, Jr. et al. |
| 3,497,516 A | 2/1970 | Mashimo et al. |
| 3,647,799 A | 3/1972 | Watanabe et al. |
| 3,818,015 A | 6/1974 | Yamato et al. |
| 3,872,130 A | 3/1975 | Kreighbaum et al. |
| 3,873,704 A | 3/1975 | Yamato et al. |
| 3,910,915 A | 10/1975 | Yonan |
| 3,910,927 A | 10/1975 | Kreighbaum et al. |
| 3,988,339 A | 10/1976 | Kaiser et al. |
| 4,054,659 A | 10/1977 | Ikezaki et al. |
| 4,321,254 A | 3/1982 | Ali |
| 4,442,108 A | 4/1984 | Le Polles et al. |
| 4,525,589 A | 6/1985 | Hidaka et al. |
| 4,536,510 A | 8/1985 | Wasserman et al. |
| 4,666,918 A | 5/1987 | Ivanova et al. |
| 4,707,485 A | 11/1987 | Kaiser et al. |
| 4,737,504 A | 4/1988 | Miller et al. |
| 4,798,897 A | 1/1989 | Hidaka et al. |
| 4,812,573 A | 3/1989 | Durant et al. |
| 4,857,301 A | 8/1989 | Czarniecki et al. |
| 5,059,608 A | 10/1991 | Takasugi et al. |
| 5,177,085 A | 1/1993 | Naef |
| 5,210,088 A | 5/1993 | Minchin et al. |
| 5,238,935 A | 8/1993 | Dugar et al. |
| 5,246,943 A | 9/1993 | Blankley et al. |
| 5,272,270 A | 12/1993 | Hirsenkorn et al. |
| 5,340,811 A | 8/1994 | Kajihara et al. |
| 5,350,757 A | 9/1994 | Blankley et al. |
| 5,362,736 A | 11/1994 | Ishikawa et al. |
| 5,446,164 A | 8/1995 | Ishikawa et al. |
| 5,498,717 A | 3/1996 | Ishikawa et al. |
| 5,519,034 A | 5/1996 | Kozlik et al. |
| 5,525,614 A | 6/1996 | Blankley et al. |
| 5,707,985 A | 1/1998 | McKenzie et al. |
| 5,750,520 A | 5/1998 | Danilewicz et al. |
| 5,756,516 A | 5/1998 | Liu et al. |
| 5,798,352 A | 8/1998 | Danilewicz |
| 5,804,586 A | 9/1998 | Sargent et al. |
| 5,807,868 A | 9/1998 | Sargent et al. |
| 5,880,285 A | 3/1999 | Broger et al. |
| 5,929,085 A | 7/1999 | MacDonald et al. |
| 6,043,253 A | 3/2000 | Brockunier et al. |
| 6,063,925 A | 5/2000 | Demian et al. |
| 6,127,381 A | 10/2000 | Basu et al. |
| 6,153,608 A | 11/2000 | Hidaka et al. |
| 6,248,754 B1 | 6/2001 | Coulton et al. |
| 6,274,594 B1 | 8/2001 | Coulton et al. |
| 6,277,861 B1 | 8/2001 | Harling et al. |
| 2001/0039289 A1 | 11/2001 | Blok et al. |

FOREIGN PATENT DOCUMENTS

| | | |
|---|---|---|
| EP | 0 210 827 A2 | 2/1987 |
| JP | 47018898 | 9/1972 |
| JP | 52095676 | 8/1977 |
| WO | WO 99/44609 A1 | 9/1999 |

OTHER PUBLICATIONS

Christoff, et al., "Synthesis and Evaluation of Trimetoquinol Derivatives: Novel Thromboxane A₂/Prostaglandin H₂ Antagonists with Diminished β–Adrenergic Agonist Activity", *J. Med. Chem.*, 1997, vol. 40, pp. 85–91.

De Los Angeles, et al., "Iodinated Analogs of Trimetoquinol as Highly Potent and Selective β₂–Adrenoceptor Ligands", *J. Med. Chem.*, 1996, vol. 39, pp. 3701–3711.

He, et al., "Synthesis and Human β–Adrenoceptor Activity of 1,2,3,4–Tetrahydroisoquinoline–6–ol Derivatives, In Vitro", *Am. Chem. Soc.*, 218ᵗʰ ACS National Meeting, Aug. 22–26, 1999, Abstract.

Ishiwata, et al., "Syntheses of Aminoisoquinolines and Related Compounds. VI. A Modified Synthesis of di–pronuciferine", *Chem. Pharm. Bull.*, 1970, vol. 18(6), Abstract.

Ishiwata, et al., "Syntheses of Aminoisoquinolines and Related Compounds. II. Syntheses of 6–amino–1–benzylisoquinolines by the Bischler–Napieralski reaction", *Chem. Pharm. Bull.*, 1969, vol. 17(11), Abstract.

(List continued on next page.)

*Primary Examiner*—Bernard Dentz
(74) *Attorney, Agent, or Firm*—Alston & Bird LLP

(57) ABSTRACT

The invention provides β₃-adrenoreceptor agonists, pharmaceutical compositions comprising β₃-adrenoreceptor agonist compounds, and methods of using such compounds for stimulating, regulating or modulating metabolism of fats in adipose tissue in animals.

28 Claims, No Drawings

OTHER PUBLICATIONS

Ishiwata, et al., "Synthesis of Aminoisoquinolines and Related Compounds. IX. Synthesis of (+−)−0−methylcaseadine", *Chem. Pharm. Bull.*, 1970, vol. 18(9), Abstract.

Memetzidis, et al., "Synthesis of Aromatic Chloroberbines", *Heterocycles*, 1990, vol. 31(2), Abstract.

Nikulin et al., "A Shortened Approach to Parallel Synthesis of Tetrahydroisoquinolines (THI) Via Bishler–Napieralski Cyclization", *Am. Chem. Soc.*, 215th ACS National Meeting, Mar. 29–Apr. 2, 1998.

Zheng, et al., "2–Amino–4–Aryl–4,5,6,7–Tetrahydrothiazolo[5,4–c]Pyridines: Proposed Novel Catechol Bioisosteric Analogs of Trimetoquinol (TMQ)—A Potent β–Adrenoceptor Agonist and TP Receptor Antagonist", *Am. Chem. Soc.*, 1995 Joint Southeast–Southwest Regional Meeting, Nov. 29–Dec. 1, 1995, Abstract.

Adejare, et al., "Syntheses and β–Adrenergic Agonist and Antiaggregatory Properties of N–Substituted Trimetoquinol Analogues[1]", *J. Med. Chem.*, 1986, pp. 1603–1609, vol. 29.

Ahn, et al., "Characterization of the Inhibition of U46619–Mediated Human Platelet Activation by the Trimetoquinol Isomers", *Biochemical Pharmacology*, 1988, pp. 3023–3033, vol. 37, No. 15.

Clark, et al., "5–Fluoro– and 8–Fluorotrimetoquinol: Selective β$_2$–Adrenoceptor Agonists", *J. Med. Chem.*, 1987, pp. 86–90, vol. 30.

Fraundorfer, et al., "Biochemical and Pharmacological Characterization of High–Affinity Trimetoquinol Analogs on Guinea Pig and Human Beta Adrenergic Receptor Subtypes: Evidence for Partial Agonism[1]", *J. Pharmacology and Experimental Therapeutics*, 1994, pp. 665–674, vol. 270, No. 2.

Fraundorfer, Paul F., "Functional and Biochemical Characterization of Trimetoquinol (TMQ) Analog Interactions with β–Adrenergic Receptor Subtypes", A Dissertation, The Ohio State University, 1993.

Harrold, et al., "Synthesis and Platelet Antiaggregatory Activity of Trimetoquinol Analogs as Endoperoxide/Thromboxane A$_2$ Antagonists", *Drug Design and Delivery*, 1987, pp. 193–207, vol. 1.

Howe, Ralph, "β$_3$–Adrenergic agonists", *Drugs of the Future*, 1993, pp. 529–549, vol. 18, No. 6.

Iwasawa, et al., Studies on Tetrahydroisoquinolines (THI) (I) Bronchodilator Activity and Structure–Activity Relationship, *Jap. J. Pharmacol.*, 1967, pp. 143–152, vol. 17.

Kajigaeshi, et al., Halogenation Using Quaternary Ammonium Polyhalides. VII. [1)] Iodination of Aromatic Amines by Use of Benzyltrimethylammonium Dichloroiodate(1–), *Bull. Chem. Soc. Jpn.*, 1988, pp. 600–602, vol. 61, No. 2.

Mayo, et al., "Stereo–Dependent Inhibition of Human Platelet Function by the Optical Isomers of Trimetoquinol", *Biochemical Pharmacology*, 1981, pp. 2237–2241, vol. 30, No. 16.

Shin, et al., "Interactions of Nonprostanoid Trimetoquinol Analogs with Thromboxane A$_2$/Prostaglandin H$_2$ Receptors in Human Platelets, Rat Vascular Endothelial Cells and Rat Vascular Smooth Muscle Cells[1]", *J. Pharmacology and Experimental Therapeutics*, 1993, pp. 1017–1023, vol. 267, No. 3.

Shin, et al., "Pharmacologic Antagonism of Thromboxane A$_2$ Receptors by Trimetoquinol Analogs In Vitro and In Vivo", *Chirality*, 1991, pp. 112–117, vol. 3.

Shin, et al., "Stereospecific Interactions of Nonprostanoid Trimetoquinol Analogs With Thromboxane A$_2$/Prostaglandin H$_2$ Receptor Sites in Human and Rat Platelets, and Rat Vascular Endothelial and Smooth Muscle Cells", *Pharmacology Communications*, 1992, pp. 303–312, vol. 1, No. 4.

Yamato, et al., "Synthesis of 6,7–Dihydroxy–1,2,3,4–Tetrahydroisoquinoline Derivatives", *Tetrahedron*, 1966, pp. 129–134, Suppl. 8, Part 1.

Konkar A. et al., "Pharmacological activites of trimetoquinol and 1–benzyl halogen–substituted analogues on rat β–adrenoceptor subtypes", *European Journal of Pharmacology*, 1996, pp. 63–71, vol. 305.

$\beta_3$-ADRENORECEPTOR AGONISTS, AGONIST COMPOSITIONS AND METHODS OF USING

CROSS-REFERENCE TO RELATED APPLICATIONS

This application is a continuation of U.S. application Ser. No. 09/164,047, filed Sep. 30, 1998, now abandoned, which claims the benefit of U.S. Provisional Patent Application Ser. No. 60/061,152, filed Sep. 30, 1997, which are incorporated herein by reference in their entirety.

BACKGROUND

1. Technical Field

The present invention relates to the field of $\beta_3$-Adrenoreceptor agonists and to methods of their preparation, formulation and use to stimulate, regulate and modulate metabolism of fats in adipose tissues in animals, particularly humans and other mammals. More particularly, the present invention relates to the field of treating obesity and overweight conditions in animals, particularly humans and other mammals and associated effects of conditions associated with obesity and overweight, including Type II diabetes mellitus (non-insulin dependent diabetes), insulin resistance, glucose intolerance, hypothyroidism, morbid obesity, and the like.

2. Prior Art

It was long thought that obesity was a consequence of self-indulgence and undisciplined behavior. Obesity was seen as evidence of gluttony, through a lack of will or capacity for self-discipline. The overweight have been disparaged, and thinness has been celebrated. Indeed, the perception of thinness as a major aspect of human beauty and attractiveness has become endemic in modern culture, and overweight conditions and obesity has increasingly grown to be an unacceptable condition for social reasons.

Masked by these cultural icons are the hard medical facts: for many individuals, a tendency to overweight and even obesity are often symptoms of organic disease or disorders of the metabolism, associated with serious and even life-threatening conditions. In medical economic terms alone, the costs attributable to overweight and obesity are staggeringly high.

A wide variety of approaches to the alleviation of obesity have ebbed and flowed though modern culture, ranging from a diverse collection of dietary strategies, to drugs, to surgical interventions, to hypnosis. All have met with indifferent success at best. Some have proved to be outright quackery. Others have proved to be effective only for the short-term, with loss of effectiveness over time. Still others have proved to be generally or at least partially successful so long as the regimen is sustained, but long term compliance is difficult to attain and in some cases has proved hazardous to other aspects of health and well-being. Some surgical procedures have had some successes, but as with any invasive procedures, there are risks. Some approaches to weight loss and control, in the extreme, lead to conditions which are themselves pathological, such as bulimia and anorexia nervosa. Other effects are less extreme, but still highly undesirable, such as amennorhea, vitamin and essential nutrient deficiencies, and the like.

A great deal of the difficulty in the art and practice of obesity and overweight management has been a consequence of attention focused on the control of appetite, and reducing the amount of food intake. It has long been the belief of many that only by the control of caloric intake is it possible to regulate body weight and fat deposition and utilization. Since appetite is controlled and regulated in the brain, brain pharmacology and the alteration of brain chemistry has been a primary focus of weight regulation and control efforts. Such approaches have led to addictions to appetite suppressants, to primary pulmonary myopathy, cardiac valve damage, and to reports of serotonin disruptions and disorders and psychotic episodes among users. Morbidities and mortalities have been unacceptably high.

In another aspect of technology relating to fat is the dietary emphasis on limiting dietary fat intake. For those who eat meats, there is increasing emphasis on low fat content meats in the carcasses of the animals employed in food stocks. Much recent efforts have been devoted to the production of beef, pork, poultry and the like with reduced fat content. Breeding patterns are being manipulated and generic engineering of farm animals is being directed at lowering fat content of the animals. The techniques of fattening of animals intended for table meat production is highly developed, but is gradually being limited by the emphasis on limiting dietary fats and interest in leaner carcass animals.

Only in very recent times has obesity been addressed in relation to the metabolic pathways of the body and their role and import in fat storage and usage in the body.

Recent research has elucidated some of the mechanisms of obesity and overweight, and has revealed that much of the limitation of prior and current weight-loss techniques stems from the fact that they are biochemically and particularly metabolically unsound and incapable of stimulating, regulating and modulating metabolism of fats in adipose tissues. Without these characteristics, it is now known, weight loss and control strategies are likely to fail or to produce conditions as bad as or worse than the weight problems they are intended to alleviate. Without heroic dedication and discipline, and even fanaticism, by the subject, most strategies are short term in their weight loss and control effects.

Increasing efforts have been directed to biochemical research into the mechanisms of fat deposition and metabolism and into stimulating, regulating and modulating metabolism of fats in adipose tissues. Considerable recent progress has been made.

Among the biochemical work of note has been the recent recognition of a role of $\beta$-Adreno-receptor activity in the metabolism of fats. It has been recognized that agonists for $\beta$-Adrenoreceptors have, in some cases, produced marked weight loss in animals, particularly humans and other mammals.

More recently, the loss of weight has been identified with the $\beta$-Adrenoreceptor sub-type, $\beta_3$-Adrenoreceptors. The specific structure of the b3-Adrenoreceptor has been characterized, and demonstrated to be a distinct cellular structure which is Distinguishable from the b1-Adrenoreceptor and the b2-Adrenoreceptor.

It has been demonstrated that compounds which are significant $\beta_3$-Adrenoreceptor agonists produce marked weight loss in animals, and that the loss is sustained with continuation of the administration of such compounds. These compounds provide potent regulation of fat metabolism. The compounds employed to date are also agonists for the $\beta_1$-Adrenoreceptor and the $\beta_2$-Adrenoreceptor sites. The lack of selectivity represents unwanted side effects of such compounds, and the compounds known as $\beta_3$-Adrenoreceptor agonists to date are not suitable candidates for therapeutic usage because of the unwanted and dangerous side effects.

PROBLEMS AND NEEDS IN THE ART

The existing strategies for weight and body fat regulation are inadequate. The current strategies are ineffective, unsafe, or both. Whether through diet manipulations or through drug usage, or combinations of such strategies, there is a lack of a clear path to safe and effective regulation of body weight and body fat which is safe and effective, which can provide significant and long lasting relief from the health consequences of overweight and obesity and the conditions associated therewith, and from the disease conditions which are aggravated by overweight and obesity.

It is clear that the art lacks and needs therapeutic agents which are highly potent and highly selective $\beta_3$-Adrenoreceptor agonists for effective stimulation, regulation and modulation of metabolism of fats in adipose tissues.

It is also clear that the art lacks and needs agents which are effective $\beta_3$-Adrenoreceptor agonists free of unwanted side effects, and which are safe for stimulating, regulating and modulating metabolism of fats in adipose tissues.

It is clear that the art lacks and needs agents which are effective at regulating the body fat of animals, particularly humans and other mammals, both in the reduction of body weight in the obese and the attendant health problems and issues, and in the production of low fat table meats from domesticated animals for human consumption.

OBJECTS OF THE INVENTION

It is an object of the present invention to provide novel compounds which are safe and effective $\beta_3$-Adrenoreceptor agonists.

It is another object of the present invention to provide syntheses of such $\beta_3$-Adrenoreceptor agonists.

Another object of the present invention is the provision of safe and effective $\beta_3$-Adrenoreceptor formulations for administration to stimulate, regulate and modulate metabolism of fats in adipose tissues in animals, particularly humans and other mammals.

Still another object of the present invention is to provide safe and effective administration of $\beta_3$-Adrenoreceptor agonists for stimulating, regulating and modulating metabolism of fats in adipose tissues in animals, particularly humans and other mammals.

Yet another object of the present invention is to provide a safe and effective regimen for causing and promoting weight loss in humans, and for the maintenance of healthy and personally desired body fat levels.

Still another object of the present invention is to provide safe and effective adjuncts to the husbandry of domesticated animals for the production of low fat dietary meats for human consumption.

The primary objective of the present invention is to provide for weight and body fat regulation through modalities which are effective and safe. The present invention provides a clear path to safe and effective regulation of body weight and body fat which is safe and effective, which can provide significant and long lasting relief from the health consequences of overweight and obesity and the conditions associated therewith, and from the disease conditions which are aggravated by overweight and obesity.

These and related objectives are met by the terms of the present invention as set out in detail in the following specification and defined in the claims appended hereto.

SUMMARY OF THE INVENTION

Compounds which are highly potent and highly specific $\beta_3$-Adrenoreceptor agonists are provided. The compounds are formulated into pharmaceutical preparations and administered for stimulating, regulating and modulating metabolism of fats in adipose tissues in animals, particularly humans and other mammals.

The compounds of the invention have one of the structures:

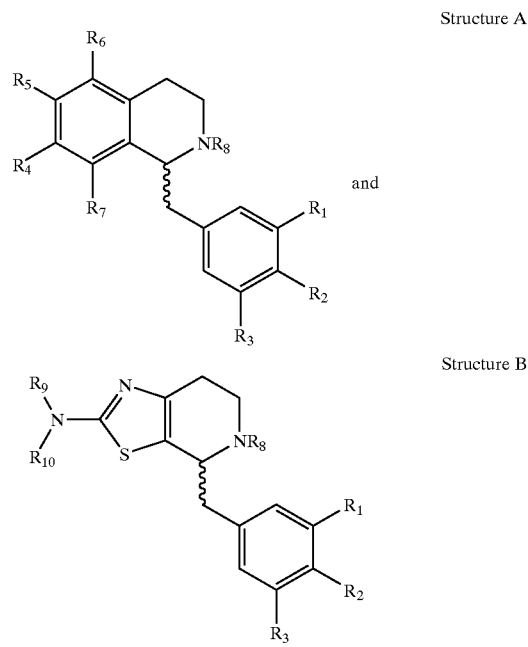

wherein:

$R_1$ and $R_3$ are independently members selected from the group consisting of H, F, Cl, Br, I, OCH$_3$, CF$_3$, CH$_3$, alkyl and aryl alkyl;

$R_2$ is a member selected from the group consisting of H, I, OCH$_3$, NH$_2$, NHR$_{13}$, NHCOR$_{13}$, NHCONHR$_{13}$ and NHCOSR$_{13}$, and provided that, when both $R_1$ and $R_3$ are CF$_3$, $R_2$ is not H;

$R_4$ and $R_5$ are each members independently selected from the group consisting of H, OH, F, Cl, Br and I, and provided that, when $R_4$ and $R_5$ are both OH or both OCH$_3$, then $R_2$ is neither NH$_2$ nor OCH$_3$;

$R_6$ and $R_7$ are independently members selected from the group consisting of H, F, Cl, Br and I;

$R_8$ and $R_{13}$ are independently members selected from the group consisting of H, lower alkyl and aryl alkyl of from 1 to about 8 carbons, F, Cl, Br, I, OCH$_3$, and CF$_3$, and provided that, when $R_{13}$ is CH$_3$, only one or none of $R_1$ and $R_3$ is I;

wherein $R_9$ and $R_{10}$ are independently members selected from the group consisting of H, lower straight chain and branched alkyl of from 1 to 8 carbon atoms,

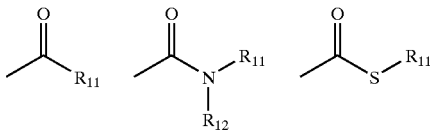

and where $R_{11}$, and $R_{12}$ are independently members selected from the group consisting of H, lower straight chain and branched alkyl of from 1 to 8 carbon atoms, and wherein $R_1$ and $R_2$, taken together, $R_2$ and $R_3$, taken together and $R_4$ and $R_5$, taken together may additionally form a member selected from the group consisting of moieties having the structure:

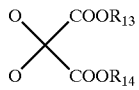

wherein $R_{13}$ and $R_{14}$ are independently members selected from the group consisting of H, lower straight chain and branched alkyl of from 1 to 8 carbon atoms,

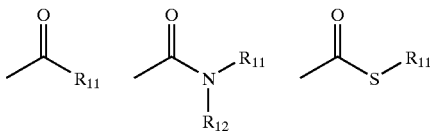

and where $R_{11}$ and $R_{12}$ are independently members selected from the group consisting of H, lower straight chain and branched alkyl of from 1 to 8 carbon atoms, and the simple inorganic and lower alkyl, of from 1 to about 8 carbons, carboxyllic acid salts thereof.

The preferred compounds of the invention are those wherein one of $R_4$ and $R_5$ is OH and the other is H. More preferably, $R_5$ is OH and $R_4$ is H. Most preferably, the compound has the following structure:

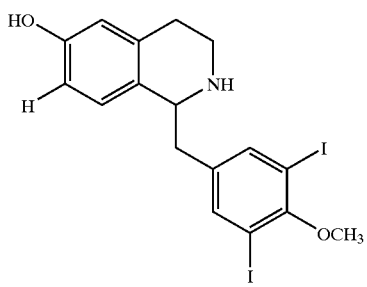

The invention is also directed to a method and pharmaceutical composition for stimulating, regulating and modulating metabolism of fats in adipose tissues in animals comprising preparing and administering an effective amount of a $\beta_3$-Adrenoreceptor selective agonist which is a member of the group consisting of:

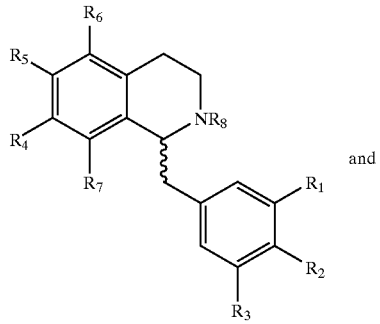

Structure A and

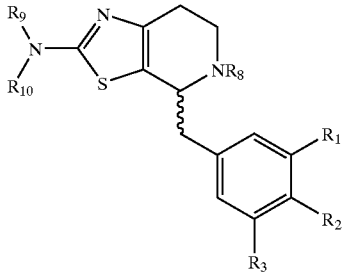

Structure B wherein:

$R_1$ and $R_3$ are independently members selected from the group consisting of H, F, Cl, Br, I, $OCH_3$, $CF_3$, $CH_3$, alkyl and aryl alkyl;

$R_2$ is a member selected from the group consisting of H, I, $OCH_3$, $NH_2$, $NHR_{13}$, $NHCOR_{13}$, $NHCONHR_{13}$ and $NHCOSR_{13}$;

$R_4$ and $R_5$ are each members independently selected from the group consisting of H, OH, F, Cl, Br and I;

$R_6$ and $R_7$ are independently members selected from the group consisting of H, F, Cl, Br and I;

$R_8$ and $R_{13}$ are independently members selected from the group consisting of H, lower alkyl and aryl alkyl of from 1 to about 8 carbons, F, Cl, Br, I, $OCH_3$, and $CF_3$;

wherein $R_9$ and $R_{10}$ are independently members selected from the group consisting of H, lower straight chain and branched alkyl of from 1 to 8 carbon atoms,

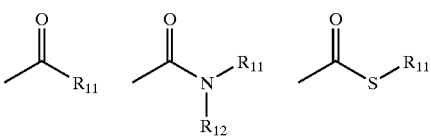

and where $R_{11}$ and $R_{12}$ are independently members selected from the group consisting of H, lower straight chain and branched alkyl of from 1 to 8 carbon atoms, and wherein $R_1$ and $R_2$, taken together, $R_2$ and $R_3$, taken together and $R_4$ and $R_5$, taken together may additionally form a member selected from the group consisting of moieties having the structure:

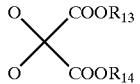

wherein $R_{13}$ and $R_{14}$ are independently members selected from the group consisting of H, lower straight chain and branched alkyl of from 1 to 8 carbon atoms,

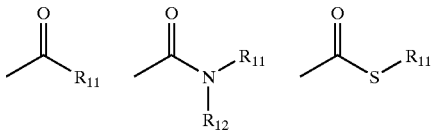

and where $R_{11}$ and $R_{12}$ are independently members selected from the group consisting of H, lower straight chain and branched alkyl of from 1 to 8 carbon atoms,
and the simple inorganic and lower alkyl, of from 1 to about 8 carbons, carboxyllic acid salts thereof.

Preferably, the method and composition use an agonist wherein one of $R_4$ and $R_5$ is OH and the other is H. More preferably, $R_5$ is OH and $R_4$ is H. Most preferably, the agonist has the following structure:

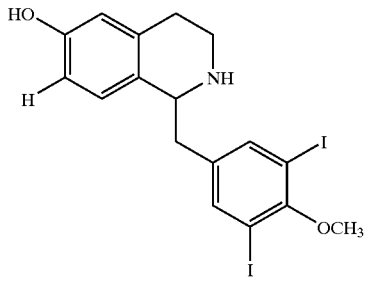

These compounds are formulated into pharmaceutical carriers to serve as highly selective, effective and safe $\beta_3$-Adrenoreceptor agonists to provide long term weight control.

In humans, the compositions are administered to control body fat levels, and to maintain acceptable body fat levels over time.

In domesticated animals, the compositions are administered to attain desirably low fat content in carcass meats intended for human consumption.

DETAILED DESCRIPTION

The following is a description of the invention, the compounds of the present invention, the method of their synthesis, their formulation into pharmaceutical compositions suitable for administration, and the method of their use for stimulating, regulating and modulating metabolism of fats in adipose tissues in animals, particularly humans and other mammals.

The discussion and presentation of bioactivity information and data in the present description is made in compliance with the standards of the Journal of Medicinal Chemistry. All chemical compounds are named in accordance with the standards of the American Chemical Society rules of standard nomenclature, employing accepted "trivial names" where applicable. All chemical structures are shown in "skeletal" form, for clarity in understanding the most significant considerations and information about the structures, with implicit hydrogen atoms not relevant to the conformation of structures not shown, in the fashion typically employed in the Journal of Medicinal Chemistry and most other journals of chemistry. The use of such structural notation is most convenient to understand the structures of such molecules, and those of ordinary levels of skill in the relevant arts are accustomed to such representations and are readily able to identify and understand such "skeletal" structures, including the implicit hydrogen atoms not shown.

Introduction

The risks and unacceptable levels of adverse consequences of many weight control and weight loss strategies available to individuals and to the medical community make the development of safe and effective modalities for stimulating, regulating and modulating metabolism of fats in adipose tissues an important need in the art and in society as a whole.

The importance of regulating dietary fat intake, and particularly saturated animal fat, has long been recognized. Consumption of meats is primary in the diet in most developed countries, and substantial efforts have been devoted to the development of leaner animals, among other strategies, to facilitate regulating and limiting of dietary intake of saturated animal fats.

In the present invention, the highly desirable goals of stimulating, regulating and modulating metabolism of fats in adipose tissues in animals, particularly humans and other mammals through the modality of administering a pharmaceutical formulation of one or more compounds which are $\beta_3$-Adrenoreceptor selective agonists is provided.

The regulatory and modulatory effect of the compounds of the present invention are dependent on continued administration over time, and the attainment of an equilibrium state which is believed to be dose dependent. In that fashion, the present invention affords the control of body fat in animals, particularly humans and other mammals, over sustained periods, at desirable levels of body fat and/or body mass indices, as defined in the medical literature.

Overview of the Invention

Safe and effective control of body fat and body mass indices have been a long sought but quite elusive goal for the medical community. The modalities in use over the past half century have proved to be both dangerous and limited in effectiveness. The longer the effort is sustained, in general, the higher the risk and the lower the effectiveness.

The weight loss effect of $\beta$-Adrenoreceptor agonists generally has been known per se for a considerable period. That recognition has not led to safe and effective weight loss or regulation because of the copious and highly dangerous side effects.

The recent discovery of the $\beta_3$-Adrenoreceptor and its focal role in fat metabolism holds the promise of the employment of $\beta_3$-Adrenoreceptor agonists in weight loss and regulation. Through the development of compounds which are highly selective for the $\beta_3$-Adrenoreceptor without activation of the $\beta_1$ Adrenoreceptor and $\beta_2$ Adrenoreceptor the present invention makes that goal attainable.

The $\beta_3$-Adrenoreceptor has not been characterized to date, which makes the search for safe and effective agonists with the required high selectivity a difficult and arduous task. Without a clear understanding of the receptor binding site, the design of effective compounds is based largely on structural activity correlations which are uncertain, unpredictable and unreliable. Even the most minor changes in structure can produce wide deviations in binding affinity, binding specificity, and agonist activity. The compounds of the present invention attain the high affinity for the $\beta_3$-Adrenoreceptor, the low affinity for the $\beta_1$ Adrenoreceptor and the $\beta_2$ Adrenoreceptor required for effective selectivity and freedom from adverse side effects, and high levels of agonist activity to make the compounds effect in their required role in fat metabolism.

The β-Adrenoreceptor Family

β Adrenoreceptors have long been known and have been studied for their role in response to the catechol amine hormones adrenaline (epinephrine), noradrenaline (norepinephrine) and dopamine.

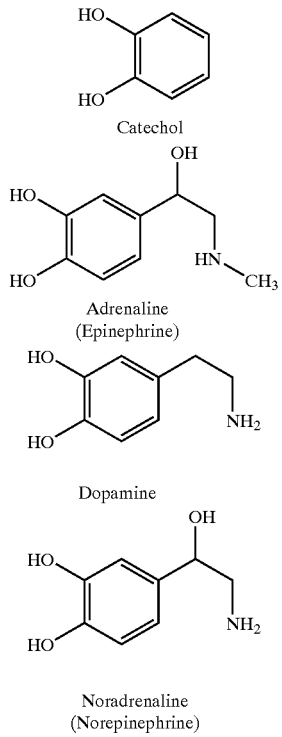

Adrenaline, to exemplify the biochemical action of these catechol amine hormones, is a primary agonist for these receptors in the body, and activates metabolic processes within the cells to which it binds. Adrenaline is associated with specific cellular processes which are dependent upon the nature of the cell to which it is bound. The action of adrenaline on the cell is to activate an enzyme within the cell, adenylate cyclase. The adenylate cyclase in turn catalyses further reactions within the target cell, typically beginning an enzyme cascade until the enzyme is broken down or deactivated by cellular regulatory mechanisms. The primary action of adenylate cyclase is the conversion of ATP to cAMP (cyclic adenosine monophosphate or "cyclic adenylate").

In the liver cells, the cAMP activates, in turn, an enzyme cascade which catalyses the conversion of glycogen into glucose and inhibits the conversion of glucose into glycogen, greatly increasing extra-cellular levels of blood glucose in the body.

In muscle tissues, cAMP triggers the breakdown of glycogen into lactate and ATP, providing high levels of ATP to support high levels of muscular activity. In the heart muscle, in particular, the effect is hypertensive and is accompanied by vasodilation throughout the body, increasing blood flow and transport of blood glucose to the cells.

β-blockers are among the commonly prescribed drugs in the field of cardiology. For the hypertensive patient, competitive binding of the blocking agent to the β Adrenoreceptors modulates and limits the additional hypertensive action of adrenaline on the heart muscle. The β-blockers may be employed in combination with vasodilators, decreasing the resistance to blood flow peripherally without increasing the heart rate and strength of contraction. A reduction in blood pressure and the work requirement on the heart muscle results.

In the lung, cAMP acts to cause bronchodilation which, when combined with increased blood flow, supplies higher levels of oxygen transport.

(Adrenaline, or epinephrine, is widely employed to stimulate bronchodilation in the treatment of asthma and allergenic reactions which constrict the bronchia.)

Others of the catechol amine hormones have comparable activities.

The release of free fatty acids from adipose tissue has been observed as an action provided by β Adrenoreceptor agonists.

A variety of β Adrenoreceptor agonists and blockers have been known for some time, and have proved to be a fruitful field for drug development.

It has been recognized that there are sub-types of the β Adrenoreceptor, designate the $\beta_1$ Adrenoreceptor and the $\beta_2$ Adrenoreceptor. Lands, et al., "Differentiation of Receptor Systems Activated by Sympathomimetic Amines" Nature, 214:597–598 (1967). Lands, et al, associate the release of free fatty acids from adipose tissue with $\beta_1$ Adrenoreceptor activation.

Subsequent studies have provided a spectrum of β Adrenoreceptor agonists and blockers. Among the blockers are both competitive and non-competitive (non-equilibrium) binding agents. Some of such agents are ubiquitous in their action, while others exhibit varying degrees of selectivity for the two sub-types (and hence in the action response produced).

Selective agonist studies show both qualitative and quantitative differentiation of the sub-types. $\beta_1$ Adrenoreceptor activation have been demonstrated to cause cardiac stimulation, release of free fatty acids from adipose tissue, and intestinal inhibition. In contrast, $\beta_2$ Adrenoreceptor activation produces broncho- and vaso-dilation.

The $\beta_3$-Adrenoreceptor

Quite recently, a third sub-type of the β Adrenoreceptor family has been identified. Howe, R. "Beta-3 adrenergic agonists." Drugs Future 1993, 18, 529–549. It has been designated the β3 Adrenoreceptor. It has also been specifically identified with the release of free fatty acids from adipose tissue, previously attributed by Lands et al. with the β1 Adrenoreceptor.

While $\beta_1$ Adrenoreceptor and $\beta_2$ Adrenoreceptor sites are ubiquitous, it has been found that the $\beta_3$-Adrenoreceptor sites are more specialized and are predominantly located on adipose tissue cells, and from studies to date appear to be rather specifically associated with the metabolism of fats.

$\beta_3$-Adrenoreceptor Agonists

This discovery leads quite directly to the search for selective and potent agonists for the $\beta_3$ Adrenoreceptor for the treatment of obesity and control of weight. The search is hindered by the lack of characterization of the receptor, but the information from binding studies and other work on β Adrenoreceptor agonists generally indicates that $\beta_3$ Adrenoreceptor agonists should be similar in structure to the catechol amine hormones.

Rather little has been published to date on $\beta_3$ Adrenoreceptor agonists. See, however, Howe, R. "Beta-3 adrenergic agonists" Drugs Future 1993, 18, 529–549. It is accordingly necessary to extrapolate from the information available about $\beta_1$ Adrenoreceptor and $\beta_2$ Adrenoreceptor agonists, and to engage in an attempt to discern structural and activity relationships from the available data. The following comments on $\beta_1$ Adrenoreceptor and $\beta_2$ Adrenoreceptor considerations summarizes what is known in the literature upon which the effort to develop $\beta_3$-Adrenoreceptor agonists can be based.

Trimetoquinol is a potent nonspecific β-adrenoreceptor (β-AR) agonist clinically used in Japan as a bronchorelaxant. Iwasawa, Y.; Kiyomoto, A. "Studies of tetrahydroisoquinolines (THI) 1. Bronchodilator activity and structure-activity relationships." *Jap. J. Pharmacol.* 1967, 17, 143–152. Optical resolution of trimetoquinol and subsequent evaluation of the stereoisomers revealed that the (S)-(−)-isomer of trimetoquinol is a potent β-adrenoreceptor agonist in heart and lung tissues; whereas, the (R)-(+)-isomer acts as a selective and highly stereospecific thromboxane A$_2$/prostaglandin H$_2$ (TP) receptor antagonist. Yamamoto, E.; Hirakura, M.; Sugasawa, S. "Synthesis of 6,7-dihydroxy-1,2,3,4-tetrahydroisoquinoline derivatives" *Tetraheron Suppl.* 1966, 8 (Part 1), 129–134. Mayo, J. R.; Navaran, S. S.; Akbar, H.; Miller, D. D.; Feller, D. R. "Stereodependent inhibition of human platelet function by the optical isomers of trimethoquinol" *Biochem. Pharmacol.* 1981, 30, 2237–2241. Ahn, C. H.; Romstedt, K. J.; Wallace, L. J.; Miller, D. D.; Feller, D. R. "Characterization of the inhibition of U46619-mediated human platelet activation by the trimetoquinol isomers. Evidence for endoperoxide/thromboxane A$_2$ receptor blockade" *Biochem Pharmacol* 1988, 37, 3023–33. Shin, Y.; Romstedt, K. J.; Miller, D. D.; Feller, D. R. "Stereodependent antagonism of thromboxane A$_2$/prostaglandin H$_2$ receptor sites by trimetoquinol isomers in human platelets, rat vascular endothelial cells and rat vascular smooth muscle cells" *Pharmacol. Commun.* 1993, 1, 303–312. Radioligand competition binding studies at β-adrenoreceptor and TP receptors show high stereoselective binding (>100-fold) for the S(−)-isomer and R(+)-isomer, respectively. This stereoselectivity is also observed in the binding of fluorinated trimetoquinol analogs at β-adrenoreceptor. Clark, M. T.; Adejare, A.; Shams, G.; Feller, D. R.; Miller, D. D. "5-fluoro- and 8-fluorotrimetoquinol: selective beta 2-adrenoceptor agonists" *J Med Chem* 1987, 30, 86–90.

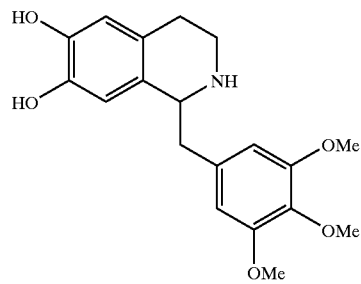

Trimetoquinol

The basic catechol structure of catecholamine hormones, such as epinephrine, norepinephrine, dopamine, and the β-adrenoreceptor agonist isoproterenol, is incorporated within the tetrahydroisoquinoline nucleus of trimetoquinol. In studies using mutated hamster $\beta_2$ Adrenoreceptor expressed in Chinese hamster ovary (CHO) cells, replacement of Asp113 with Asn113 abolished receptor binding of trimetoquinol and its analogs. Fraundorfer, P. F. "Functional and biochemical characterization of trimetoquinol (TMQ) analog interactions with β-adrenergic receptor subtypes" Ph. D. Thesis, The Ohio State University, 1993 ("Fraundorfer-2"). In addition, replacement of Ser204 and Ser207 with Ala204 and Ala207 decreased the binding affinity of trimetoquinol analogs in $\beta_2$ Adrenoreceptor to a lesser extent, but greatly diminished their ability to stimulate cAMP accumulation. "Fraundorfer-2", supra. However, both the binding and functional activities of isoproterenol are significantly reduced in the $\beta_2$ adrenoreceptor Asn113, Ala204 and Ala207 mutants. These results suggest that although trimetoquinol analogs may interact with the same amino acid residues in the binding site as isoproterenol, the contribution of catechol interactions with these mutated $\beta_2$ Adrenoreceptors is less significant in terms of ligand binding and may well be overshadowed by the binding contributions of the trimethoxybenzyl group of trimetoquinol.

Substitution with fluorine or iodine on the 5- or 8-positions of trimetoquinol resulted in only a modest (~10-fold) increase in $\beta_2$ Adrenoreceptor versus $\beta_1$ adrenoreceptor selectivity as compared to trimetoquinol in functional and binding studies. Clark, et al., supra; Fraundorfer, P. F.; Fertel, R. H.; Miller, D. D.; Feller, D. R. "Biochemical and pharmacological characterization of high-affinity trimetoquinol analogs on guinea pig and human beta adrenergic receptor subtypes: evidence for partial agonism" *J Pharmacol Exp Ther* 1994, 270, 665–74. In addition, it has also found that replacement of the 3'- and 5'-methoxy substituent of trimetoquinol with iodine atoms (i.e., 2) is well tolerated on both β-adrenoceptor, Fraundorfer, et al., supra, and TP receptors. Shin, Y.; Romstedt, K. J.; Miller, D. D.; Feller, D. R. "Interactions of nonprostanoid trimetoquinol analogs with thromboxane A$_2$/prostaglandin H$_2$ receptors in human platelets, rat vascular endothelial cells and rat vascular smooth muscle cells" *J Pharmacol Exp Ther* 1993, 267, 1017–23.; Harrold, M. W.; Gerhardt, M. A.; Romstedt, K.; Feller, D. R.; Miller, D. D. "Synthesis and platelet antiaggregatory activity of trimetoquinol analogs as endoperoxide/thromboxane A2 antagonists" *Drug Des Deliv* 1987, 1, 193–207.

Interestingly, although its binding affinity at $\beta_1$ adrenoreceptor is slightly better than trimetoquinol, compound 2 displays a much higher affinity than trimetoquinol for $\beta_2$ adrenoreceptor:

Compound 2

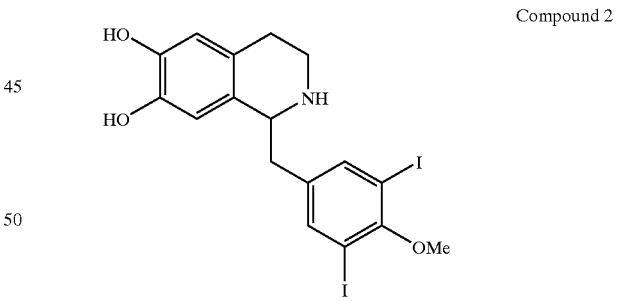

These earlier findings suggest that trimetoquinol analogs interact with an auxiliary site through the substituted benzyl group in addition to the binding site shared by catecholamines. This subsite can be used to advantage in the development of more site-selective agents. The high potency of compound 2 seems to suggest that this auxiliary site is hydrophobic in nature. On TP receptors, the complementary binding sites for trimetoquinol analogs are essentially unknown. However, compound 2 is a more potent TP receptor antagonist than trimetoquinol further suggesting that 1-benzyl ring modifications are appropriate to develop agents with greater selectivity on β-adrenoreceptor versus TP receptors and vice versa.

The literature describes the synthesis and evaluation of iodinated trimetoquinol analogs designed as probes for characterizing the receptor binding interactions, associated with the benzyl substituent of trimetoquinol analogs and as site-selective β-adrenoreceptor and TP receptor ligands. These chemical modifications provide a greater separation of the pharmacological activities for this class of compounds. Site-selective β-adrenoreceptor agents have potential in the treatment of cardiopulmonary diseases, non-insulin dependent diabetes (Type II) and obesity, Howe, R., "Beta-3 adrenergic agonists" *Drugs Future* 1993, 18, 529–549, whereas highly selective TP receptor antagonists have value in the treatment of thrombolytic disorders. Shin, supra; Shin, Y.; Romstedt, K. J.; Miller, D. D.; Feller, D. R., "Interactions of nonprostanoid trimetoquinol analogs with thromboxane $A_2$/prostaglandin $H_2$ receptors in human platelets, rat vascular endothelial cells and rat vascular smooth muscle cells" *J Pharmacol Exp Ther* 1993, 267, 1017–23; Shin, Y.; Romstedt, K.; Doyle, K.; Harrold, M.; Gerhardt, M.; Miller, D.; Feller, D., "Pharmacologic antagonism of thromboxane $A_2$ receptors by trimetoquinol analogs." *Chirality* 1991, 3, 112–117.

Other known $β_1$-adrenoreceptor and $β_2$-adrenoreceptor agonists include isoproterenol, X and Y, having the structures:

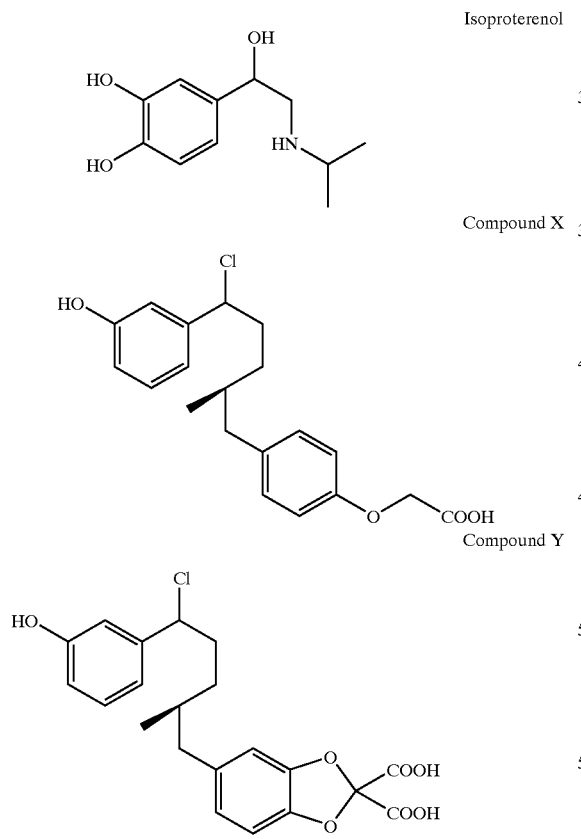

While these compounds are highly active $β_3$-adrenoreceptor agonists, they are also non-selective, and also bind and activate the $β_1$-adrenoreceptor and $β_2$-adrenoreceptor with comparable affinities and activities. They are thus entirely unsuited for use in the present invention, but they do afford good basis for comparative and competitive binding studies, and are employed in the present invention for those purposes when appropriate.

The Compounds of the Invention

The present invention is based on the provision of $β_3$-adrenoreceptor agonists in pharmaceutically acceptable carrier formulations for administration to stimulate, regulate and modulate metabolism of fats in adipose tissues in animals, particularly humans and other mammals.

The present invention additionally provides a method for safe and effective administration of $β_3$-Adrenoreceptor agonists for stimulating, regulating and modulating metabolism of fats in adipose tissues in animals, particularly humans and other mammals.

The present invention provides potent, highly selective $β_3$-Adrenoreceptor agonists which are compounds having the structures:

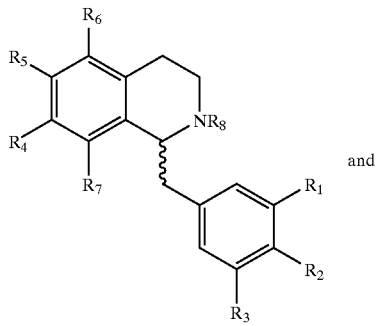
Structure A and

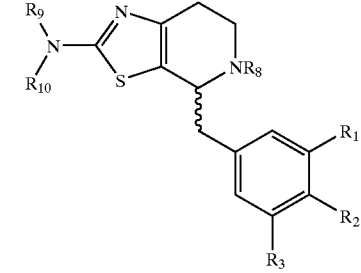
Structure B wherein:

$R_1$ and $R_3$ are independently members selected from the group consisting of H, F, Cl, Br, I, $OCH_3$, $CF_3$ and $CH_3$, alkyl and aryl alkyl;

$R_2$ is a member selected from the group consisting of H, I, $OCH_3$, $NH_2$, $NHR_8$, $NHCOR_{13}$, $NHCONHR_{13}$ and $NHCOSR_{13}$, and provided that, when both $R_1$ and $R_3$ are $CF_3$, $R_2$ is not H;

$R_4$ and $R_5$ are each members independently selected from the group consisting of H, OH, F, Cl, Br and I, and provided that, when both $R_4$ and $R_5$ are OH, then $R_2$ is neither $NH_2$ nor $OCH_3$;

$R_6$ and $R_7$ are independently members selected from the group consisting of H, F, Cl, Br and I;

$R_8$ and $R_{13}$ are independently members selected from the group consisting of H, lower alkyl of from 1 to about 8 carbons, F, Cl, Br, I, $OCH_3$, and $CF_3$ wherein $R_9$ and $R_{10}$ are independently members selected from the group consisting of H, lower straight chain and branched alkyl of from 1 to 8 carbon atoms,

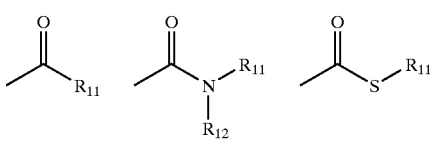

and where $R_{11}$ and $R_{12}$ are independently members selected from the group consisting of H, lower straight chain and branched alkyl of from 1 to 8 carbon atoms, and wherein $R_1$ and $R_2$, taken together, $R_2$ and $R_3$, taken together and $R_4$ and $R_5$, taken together may additionally form a member selected from the group consisting of moieties having the structure:

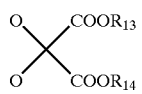

wherein $R_{13}$ and $R_{14}$ are independently members selected from the group consisting of H, lower straight chain and branched alkyl of from 1 to 8 carbon atoms,

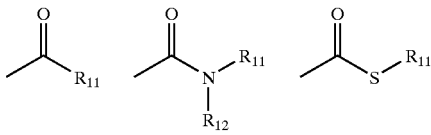

and where $R_{11}$ and $R_{12}$ are independently members selected from the group consisting of H, lower straight chain and branched alkyl of from 1 to 8 carbon atoms, and the simple inorganic and lower alkyl, of from 1 to about 8 carbons, carboxyllic acid salts thereof.

It is preferred that the compounds of the present invention be further qualified and limited to those with high selectivity and high activity for the $\beta_3$-Adrenoreceptor In addition, there are several particularly preferred species, i.e., specific compounds, which are preferred. These particularly preferred species include the following compounds:

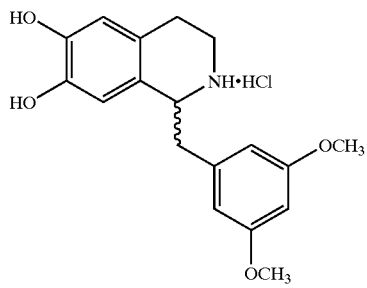

Formula A 1

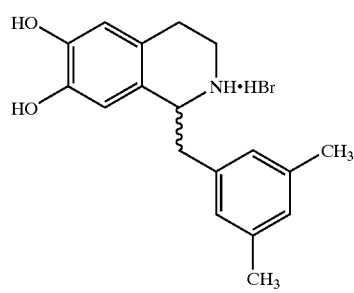

Formula A 2

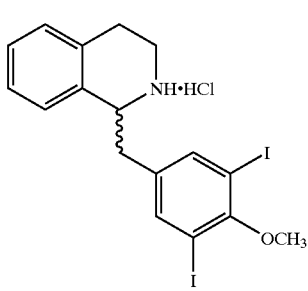

Formula A 3

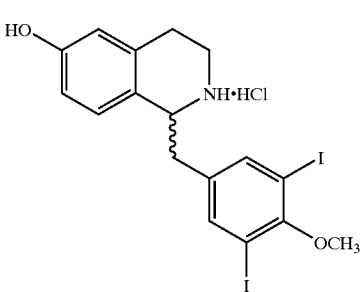

Formula A 4

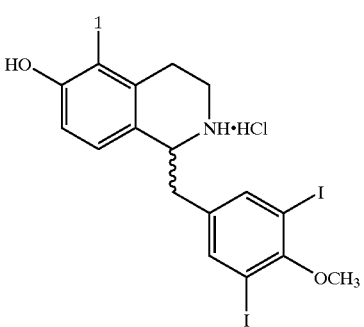

Formula A 5

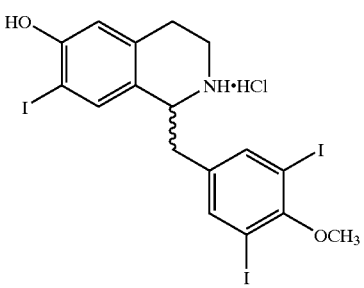

Formula A 6

Formula A 7
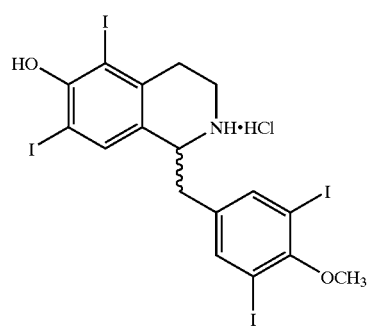
Formula A 8
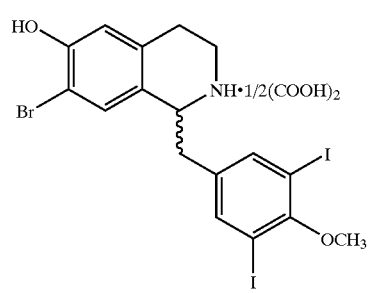
Formula A 9
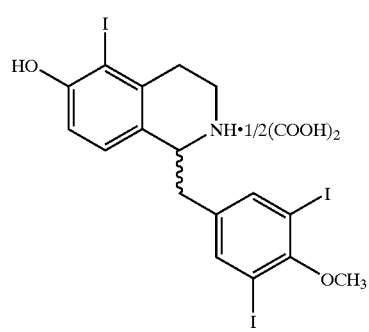
Formula A 10
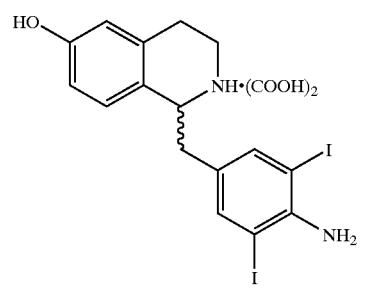
Formula A 11
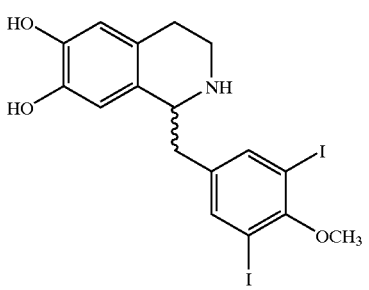
Formula A 12
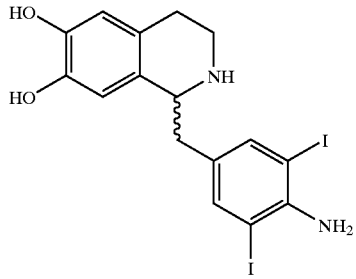
Formula A 13
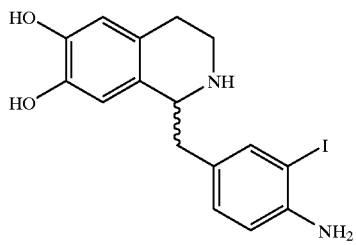
Formula A 14
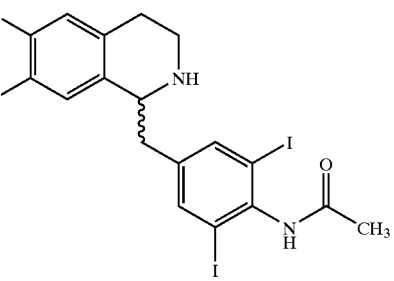
Formula A 15
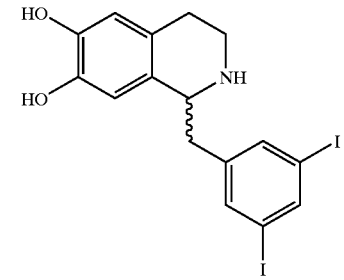
Formula A 16
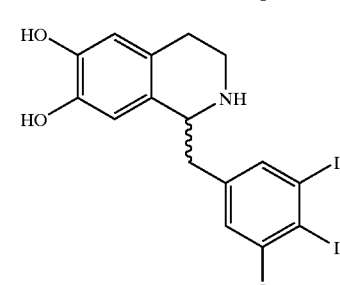

Formula A 17
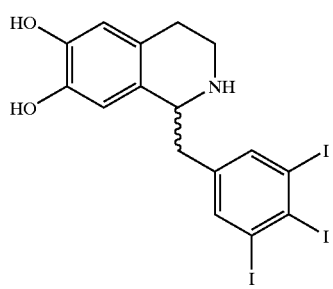
Formula A 18
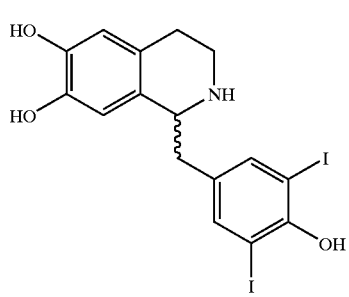
Formula A 19
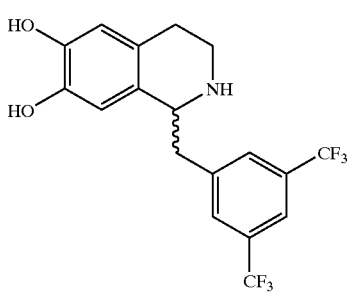
Formula A 20
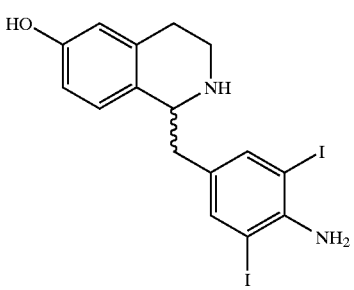
Formula A 21
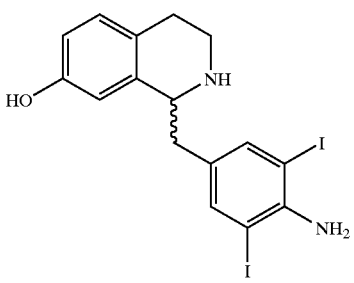
Formula A 22
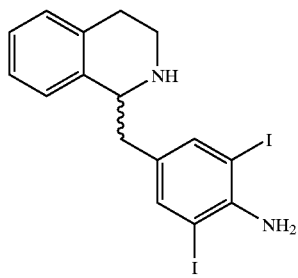
Formula A 23
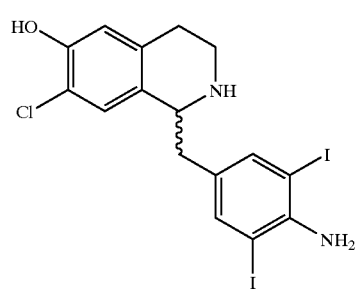
Formula A 24
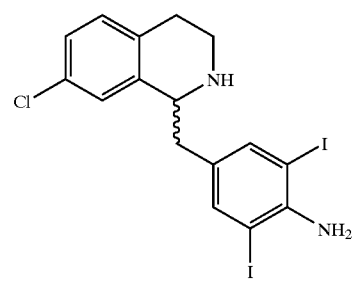
Formula A 25
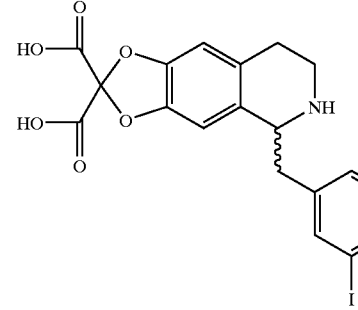
Formula A 26
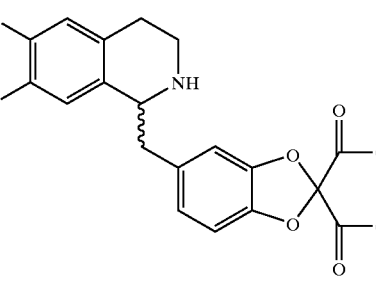

-continued
Formula A 27
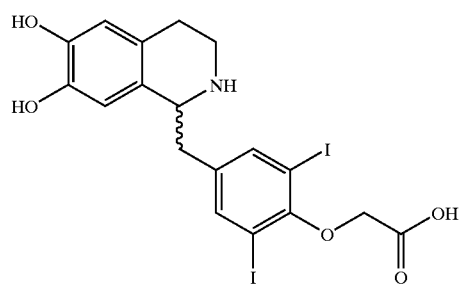
Formula A 28
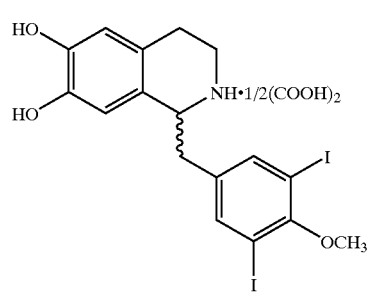
Formula A 29
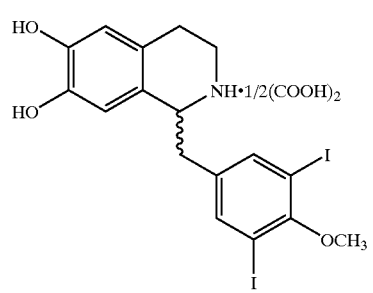
Formula A 30
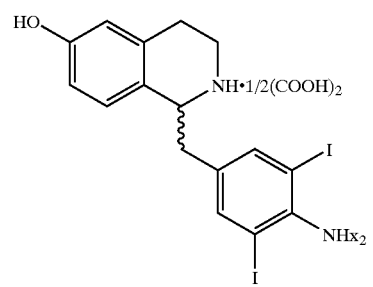
Formula A 31
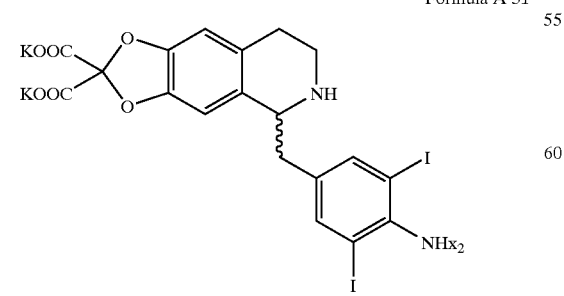
-continued
Formula A 32
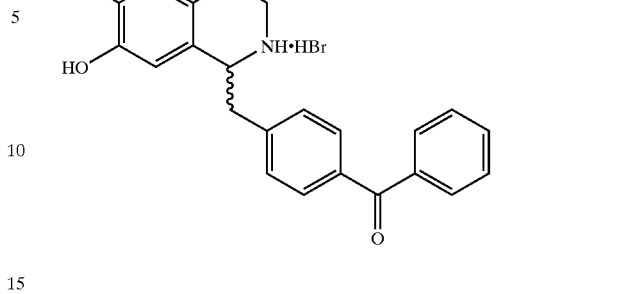
Formula A 33
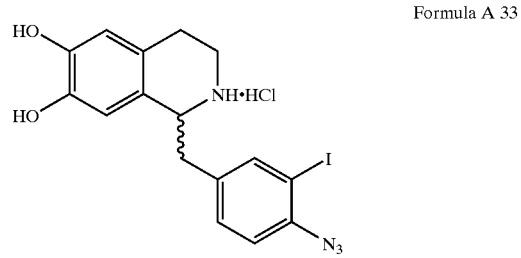
Formula A 34
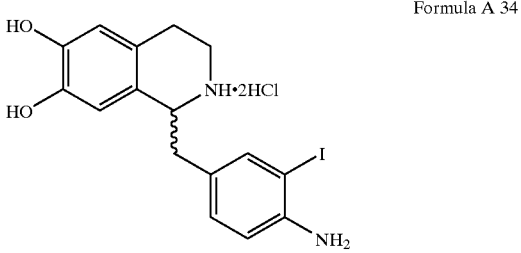
Formula A 35
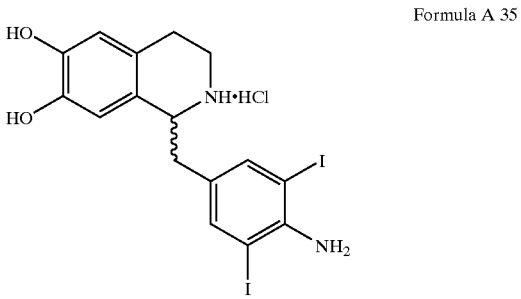
Formula A 36
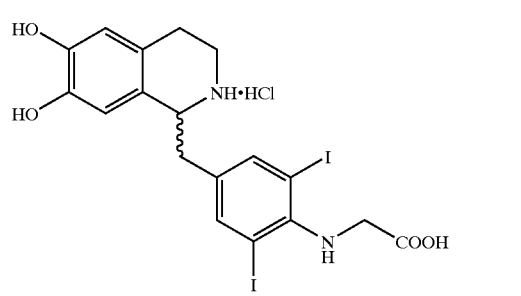

Formula A 37
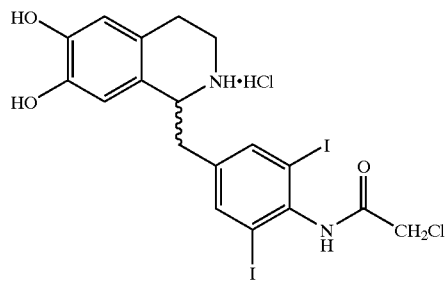
Formula A 38
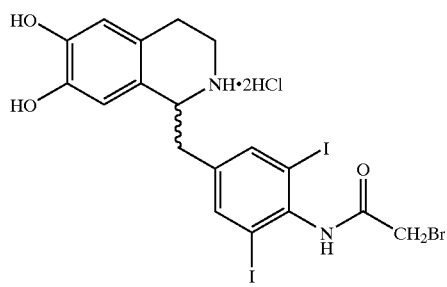
Formula A 39
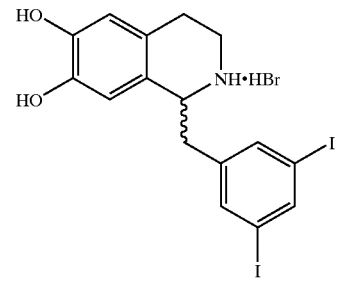
Formula A 40
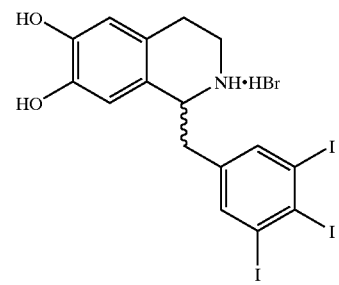
Formula A 41
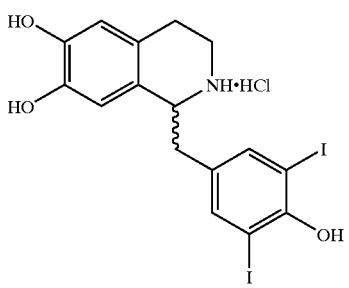
Formula A 42
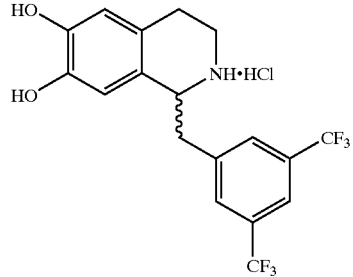
Formula A 43
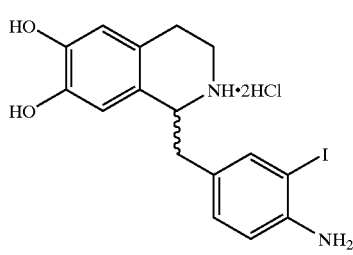
Formula A 44
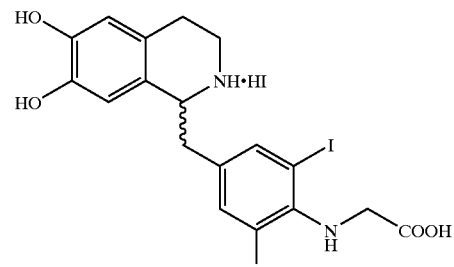
Formula A 45
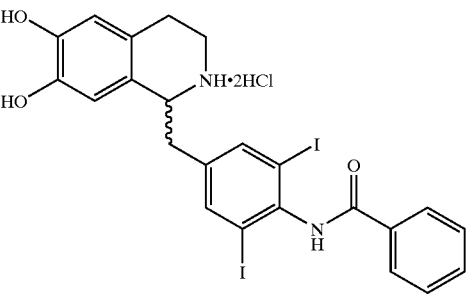
Formula A 46
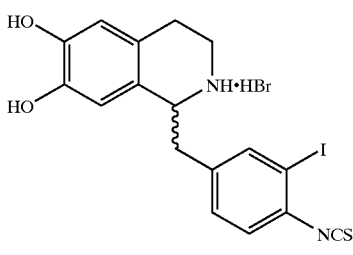

Formula B 1
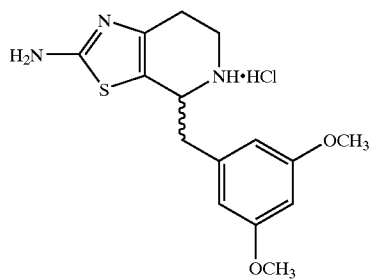
Formula B 2
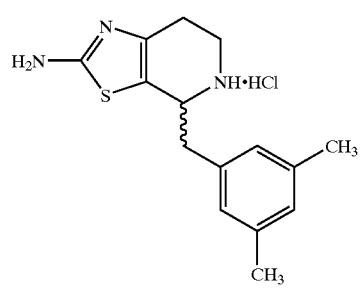
Formula B 3
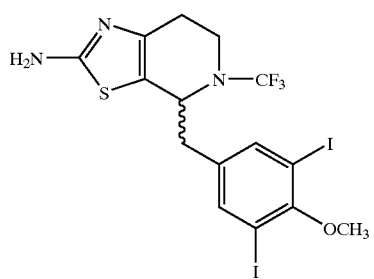
Formula B 4
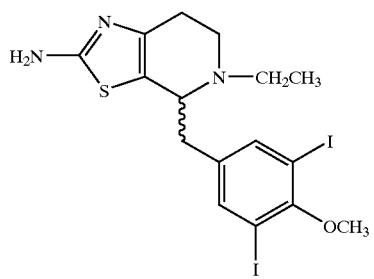
Formula B 5
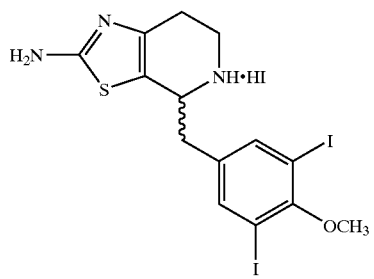
Formula B 6
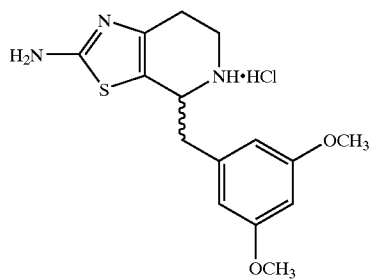
Formula B 7
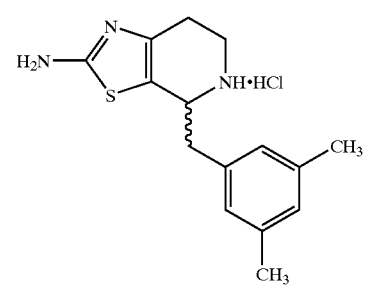
Formula B 8
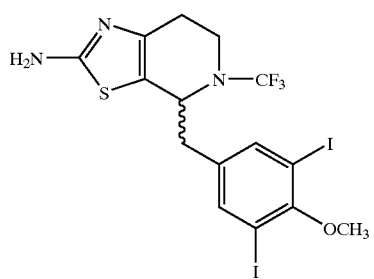
Formula B 9
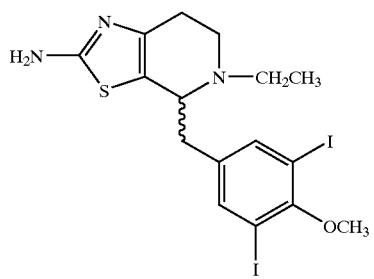
Formula B 10
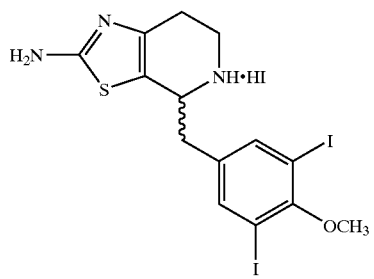

Formula B 11
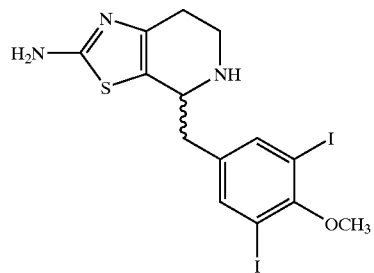
Formula B 12
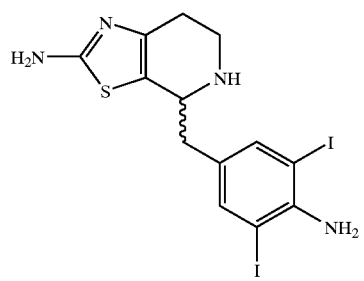
Formula B 13
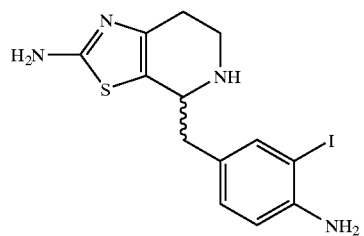
Formula B 14
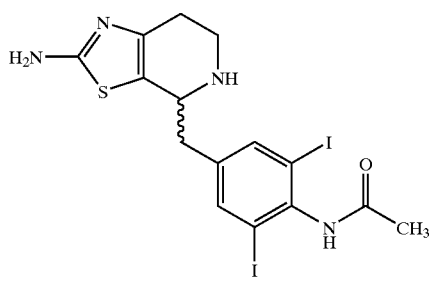
Formula B 15
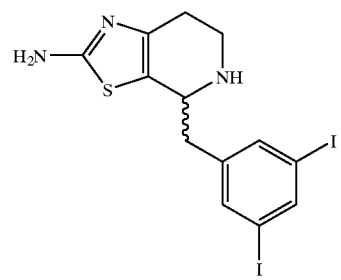
Formula B 16
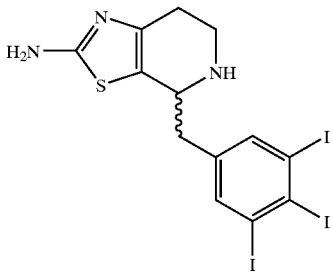
Formula B 17
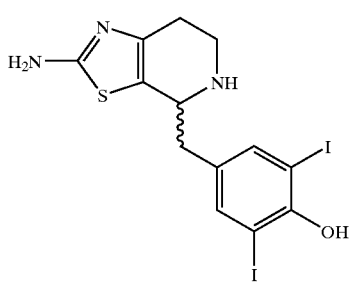
Formula B 18
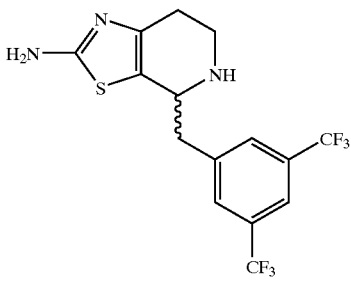
Formula B 19
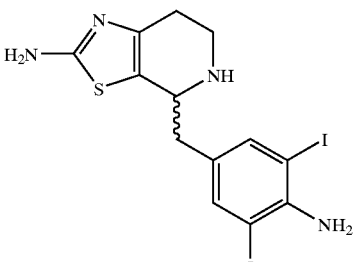
Formula B 20
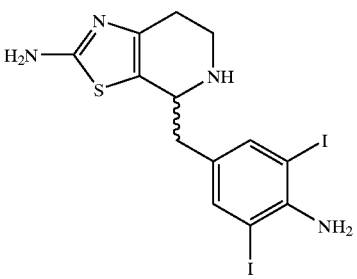

Formula B 21
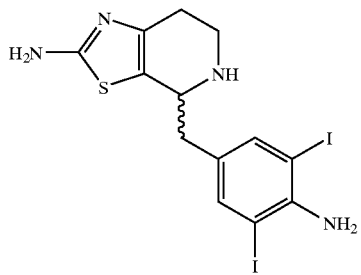

Formula B 22
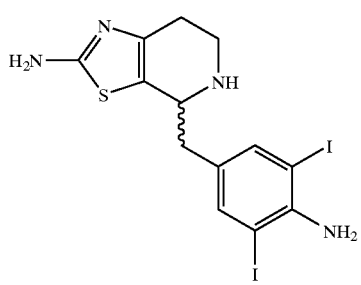

Formula B 23
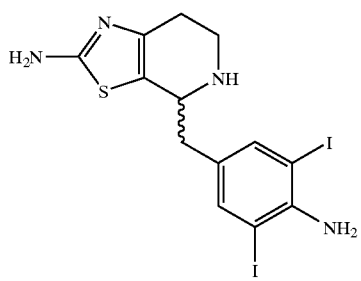

Formula B 24
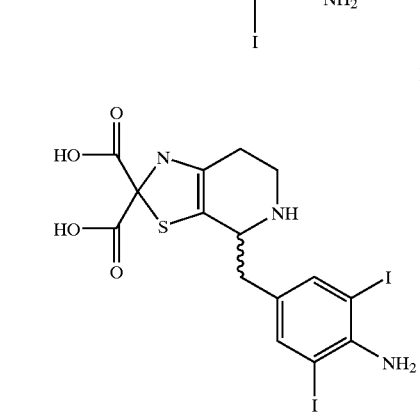

Formula B 25
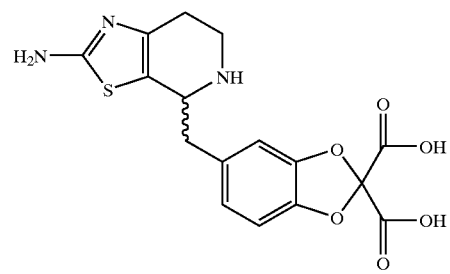

Formula B 26
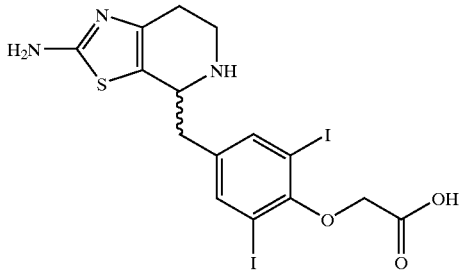

Formula B 27
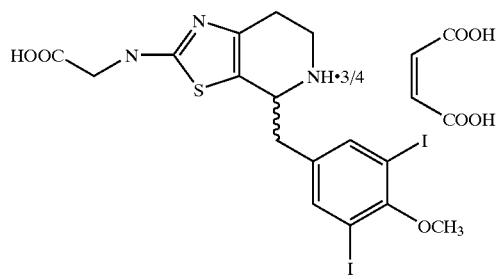

Formula B 28
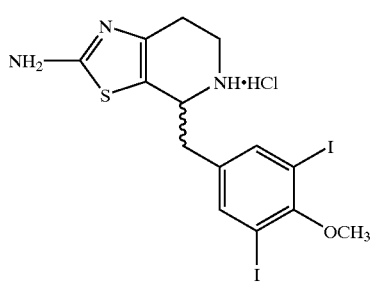

Formula B 29
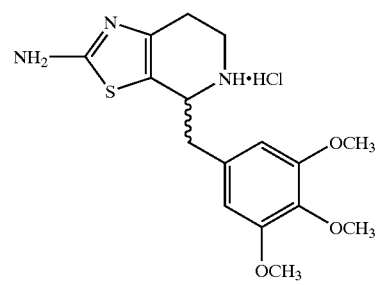

Of these compounds, the following are preferred, A1, A2, A3, A4, A5, A6, A7, A8, A9, A10, A20, A21, A22, A23, A24, A25, A26, A27, A30, A31, A32, A33, A34, A36, A37, A38, A41, A42, A44, A45, A46, and all of the B compounds. At present, the most preferred compound is A4.

Synthesis of TMQ Derivatives

A convenient protection scheme has been devised for the synthesis of the desired $\beta_3$-Adrenoreceptor agonists of the present invention. The triple protected isoquinoline intermediates were synthesized as shown in Scheme 1. The tetrahydroisoquinolines 6a-c were synthesized from the O-methyl or O-benzyl protected catecholamines 3a or 3b, respectively, and 4-nitrophenylacetic acid (4a) or 3,5-bis-trifluoromethylphenylacetic acid (4b) using methods described previously. Clark, M. T.; Adejare, A.; Shams, G.; Feller, D. R.; Miller, D. D. "5-fluoro- and 8-fluorotrimetoquinol: selective beta 2-adrenoceptor agonists" *J Med Chem* 1987, 30, 86–90.; Harrold, M. W.; Gerhardt, M. A.; Romstedt, K.; Feller, D. R.; Miller, D. D. "Synthesis and platelet antiaggregatory activity of trimetoquinol analogs as endoperoxide/thromboxane A2 antagonists" *Drug Des Deliv* 1987, 1, 193–207. Adejare, A.; Miller, D. D.; Fedyna, J. S.; Ahn, C. H.; Feller, D. R. "Syntheses and beta-adrenergic agonist and antiaggregatory properties of N-substituted trimetoquinol analogues" *J Med Chem* 1986, 29, 1603–9. The amino group of 6a and 6b were protected with trifluoroacetyl (TFA) and t-butyloxycarbonyl (t-BOC), respectively. The nitro groups of 7a,b were reduced via catalytic hydrogenation using Pd/C or Raney Nickel, respectively, to give the aniline derivatives 8a,b. Iodination of 8a,b with 1 equivalent of benzyltrimethylammonium dichloroiodate (BTMACl$_2$I) according to Kajigaeshi et al., Kajigaeshi, S.; Kakinami, H.; Fujisaki, S.; Okamoto, T. "Halogenation using quaternary ammonium polyhalides. VII. Iodination of aromatic amines by use of benzyltrimethylammonium dichloroiodate (I$^-$)" *Bull. Chem. Soc. Jpn.* 1968, 61, 600–602, led to the 3'-iodo analogs 9a,b. An additional 3 equivalents of BTMACl$_2$I added in portions over a 3 day period was required to convert 8a completely to the diiodo derivative 10a.

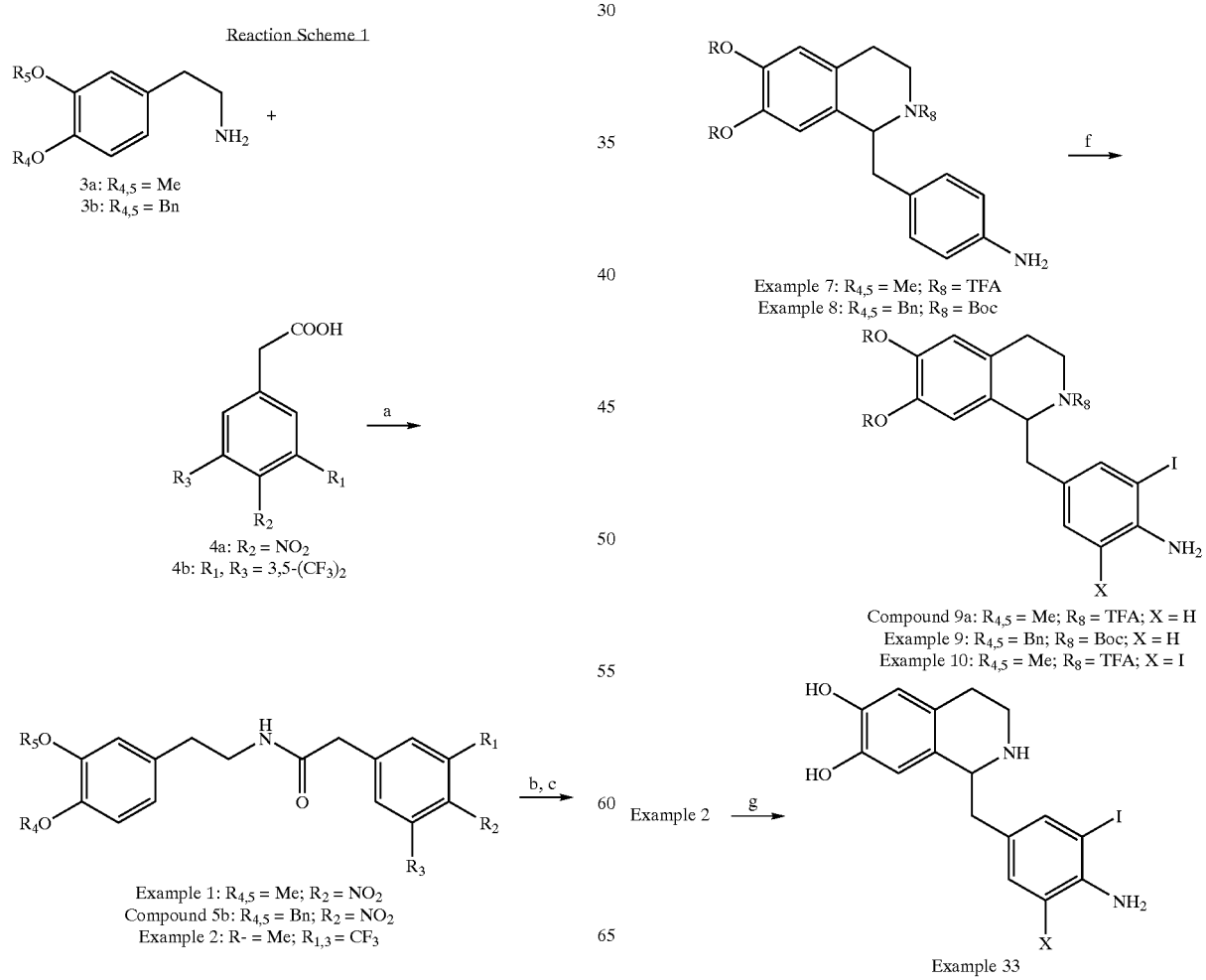

-continued

Notes to Reaction Scheme 1:
(a) Toluene, reflux (Dean-Stark trap), 72 hours;
(b) POCl$_3$, MeCN, reflux;
(c) NaBH$_4$, MeOH;
(d) TFAA, THF (Example 3) or (Boc)$_2$O (NaOH, THF (Example X);
(e) H$_2$, Pd/C (Example 5) or Raney Ni (Example 6);
(f) 1 equiv. Of BTMACl$_2$I, MeOH, CH$_2$Cl$_2$, 20 hours (Examples Examples 7,8), or 4 equiv. Of BTMACl$_2$I, CaCO3, M·OH, CH$_2$Cl$_2$, 3days (Example 7)
(g) 1. BBr$_3$, CH$_2$Cl$_2$, 2. MeOH Interestingly, the diiodo product 10a, was often isolated as light pink to reddish crystals. It has been found that the minor side product 11 (Scheme 2) was responsible of the reddish coloration. TLC analysis of the reaction mixture and isolated crude product indicate that compound 11 is formed mostly during workup. Compound 11 was isolated by flash chromatography. The structure 11 and its ceacetylatioin product 12 was proven by $^1$H and $^{13}$CNMR and elemental analysis. Compound 11 was also isolated in an attempt to convert the 4'-amino of 10a to a hydrazine group. Thus, diazotization of 10a, followed by reduction with H$_2$SO$_3$ gave compound 11 as the only isolated product in low yield.

der aromatischen Reihe Ber. 1894, 27, 93–101. With this in mind, mono-acetylation was accomplished by reacting 10a with 5 equivalents of acetyl chloride in the presence of 4-dimethylaminopyridine (DMAP) and triethylamine at room temperature to afford 13. Basic hydrolysis of the trifluoroacetyl protecting group of 10a and 13gave 20c and 14, respectively. The methoxy derivatives 20c, 14, and 6c were demethylated with BBr$_3$ to afford the desired trimetoquinol analogs 21c, 15, and 27, respectively, as hydrobromide salts (Sch m 1 and 3). In a similar manner, the 6,7-dibenzyloxy-1-(3,5-diiodo-4-methoxybenzyl)-1,2,3,4-tetrahydro-isoquinoline, Harrold, M. W.; Gerhardt,. M. A.; Romstedt, K.; Feller, D. R.; Miller, D. D. Synthesis and platelet antiaggregatory activity of trimetoquinol analogs as endoperoxide/thromboxane A2 antagonists *Drug Des Deliv* 1987, 1, 193–207, was dealkylated with BBr$_3$ to give 6,7-dihydroxy-1-(3,5-diiodo-4-hydroxybenzyl)-1,2,3,4-tetrahydroisoquinoline (18) the desmethyl analog of 2. Diazotization of 10a (Scheme 3) followed by reaction of the

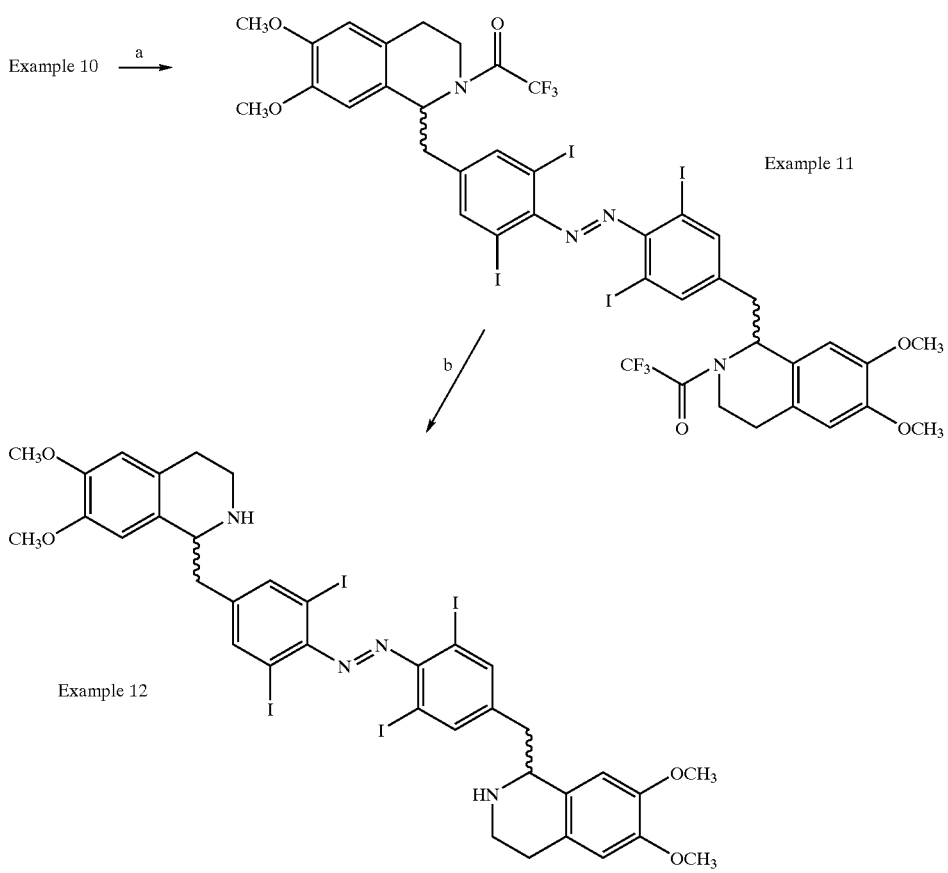

Notes to Reaction Scheme 2:
(a) 1. NaNO$_2$, H$_2$SO$_4$, AcOH, 2. H$_2$SO$_3$
(b) NaNO$_2$, H$_2$SO$_4$, H$_2$O While reaction of 10a with acetic anhydride at room temperature did not give the desired 4'-acetamido derivative 13, heating 10a in acetic anhydride at reflux resulted in the diacetylation product 16(Scheme 3). Similar diacetylation has been reported with the reaction of 2,6-dibromo-4-toluidine with refluxing acetic anhydride while lower temperatures gave a mixture of mono and diacetylated products. Ulffers, F.; von Janson, A. Diacetylderivate einer Amine diazonium salt with H$_3$PO$_2$ or potassium iodide (KI) gave the diiodo and triiodo derivatives, 19a and 19b, respectively. Basic hydrolysis of the trifluoroacetyl group of 19a,b as before gave 20a,b. Demethylation of 20a,b with BBr$_3$ proceeded smoothly to give 21a,b. Compound 9a was acylated with acetic anhydride in refluxing benzene to give 22which was deprotected in the same manner as 14to give 23(Scheme 4).

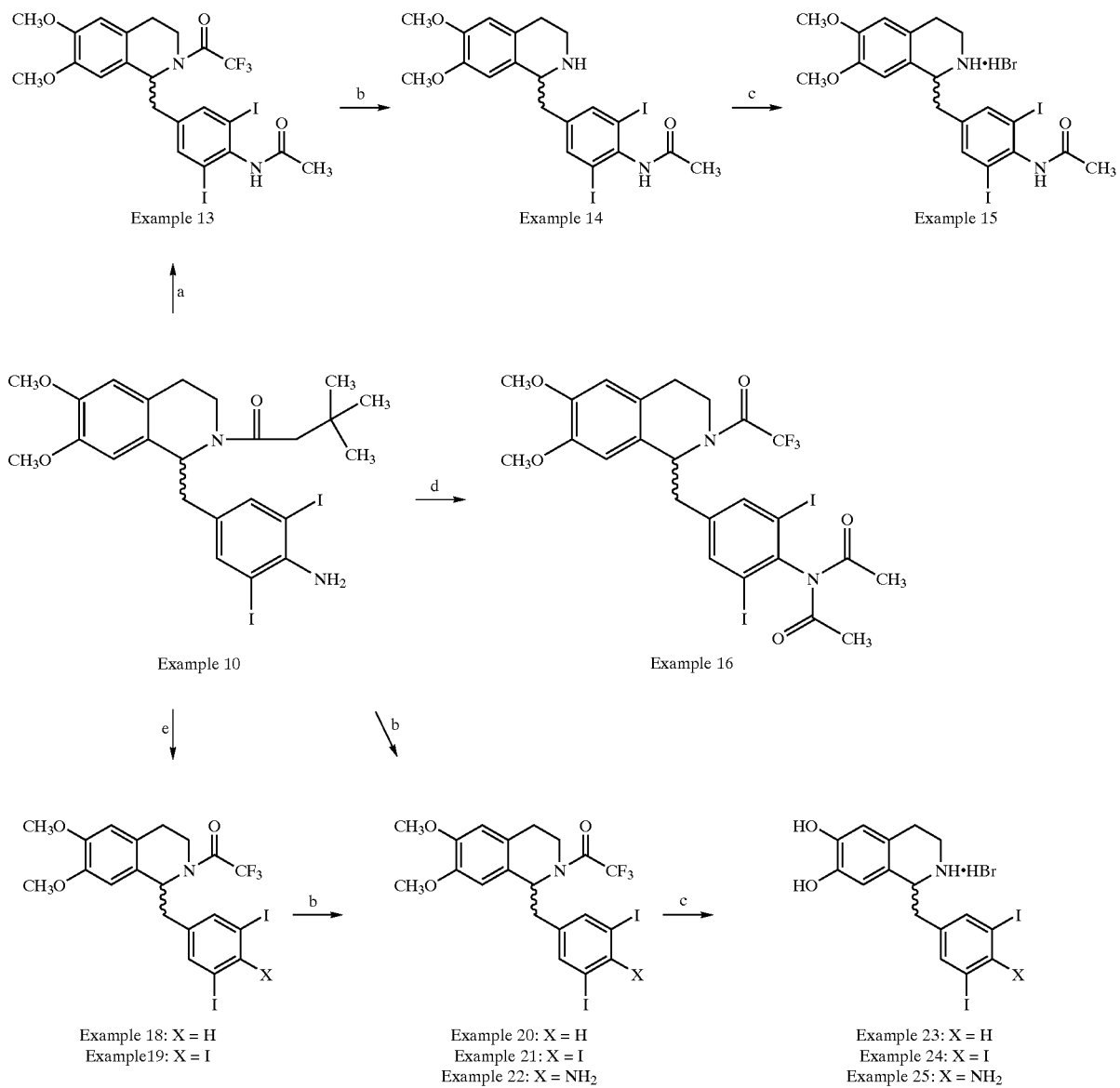

Reaction Scheme 3

Notes to Reaction Scheme 3:
(a) AcCl, Et₃N, DMAP;
(b) K₂CO₃, MeOH, H₂O;
(c) 1. BBr₃, CH₂Cl₂, 2. MeOH;
(d) Ac₂O, reflux;
(e) NaNO₂, H₂SO₄, AcOH, 2. H₃PO₂ or KI However, attempts to demethylate 23 with BBr₃ failed to give the desired product 26a. Surprisingly, the amide bond of 23 was cleaved to give aniline 24. This indicates the importance of both ortho-iodine atoms as a steric hindrance toward cleavage of the acetamido group of 14 by BBr₃. Trimethylsilyliodide (TMSI) was thus employed as a mild reagent for ether cleavage. However, this agent was too weak to effect demethylation of 23; therefore, the catechol O-methyl ether protecting groups were changed to benzyl ethers. Hence, compounds 26a and 26b were prepared from the O-benzyl and N-t-BOC protected 9b (Schem 4). The acylated compounds 25a and 25b were deblocked using TMSI. Initially, using the procedure of Lott, R. S.; Chauhan, V. S.; Stammer, C. H. "Trimethylsilyl iodide as a peptide deblocking agent" J. Chem. Soc. Chem. Comm. 1979, 495–496, (TMSI, MeCN, 50° C. 2 h) amide 25a gave the desired amide 26a along with a significant amount of the deacetylation product 24. Ordinarily, amides are stable to TMSI. To optimize the selectivity, the TMSI deprotection reaction was monitored by NMR spectroscopy at room temperature. The O-benzyl protecting groups were removed within 6 h and no cleavage of the amide bond was observed at this temperature for 20 h. Thus, using the following reaction conditions: 4–6 eq. of TMSI, MeCN, room temperature, 6 h, 26a and 26b from 25a and 25b were obtained, respectively.

Reaction Scheme 4
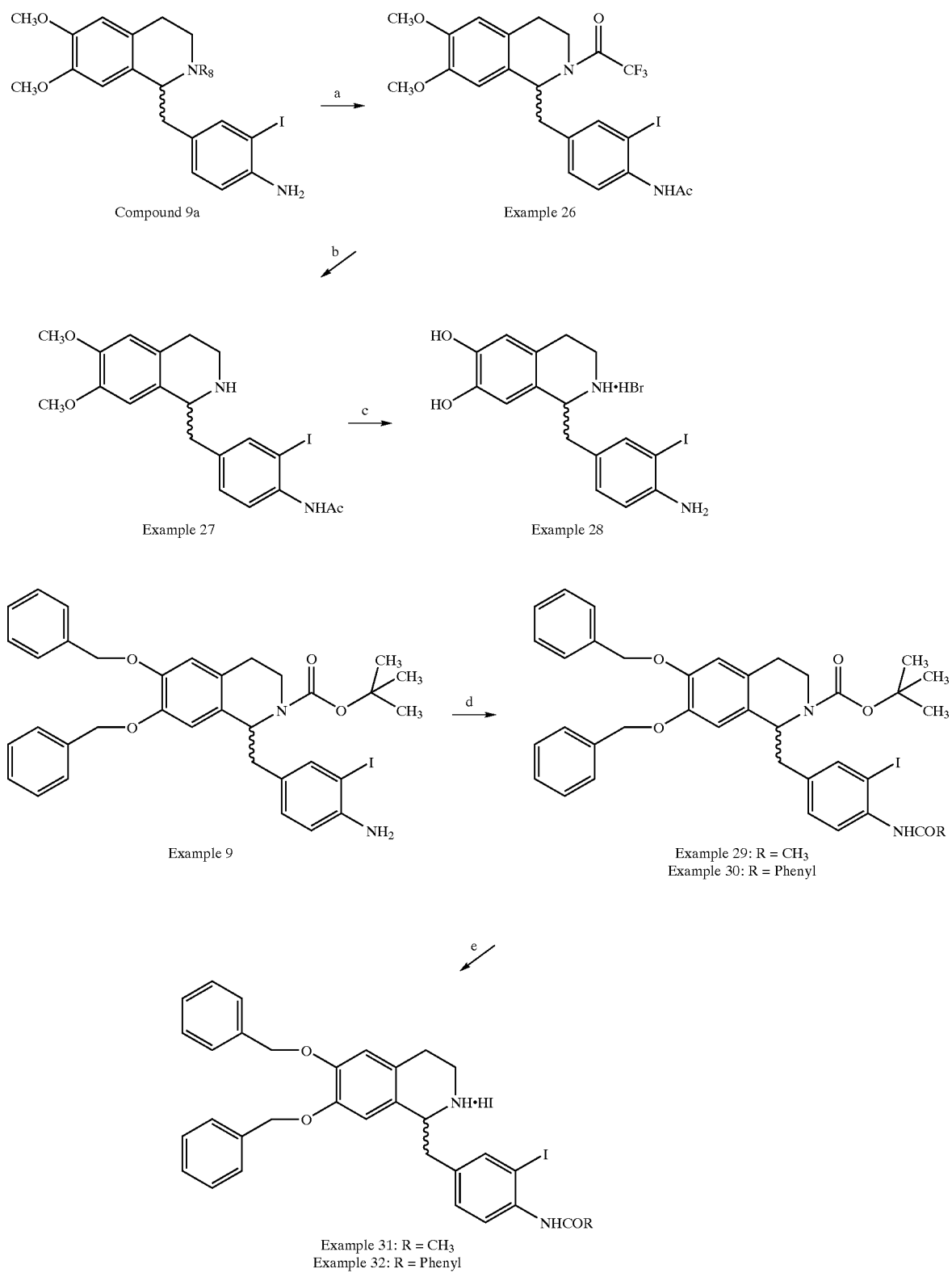
Notes to Reaction Scheme 4:
(a) AcCl, Et₃N
(b) K₂CO₃, MeOH, H₂O
(c) 1. BBr₃, CH₂Cl₂; 2. MeOH,
(d) Ac₂O, Δ or PhCOCl, Et₃N
(e) 1. TMSI, MeCN; 2. MeOH The proton NMR spectra of synthesized compounds were quite complicated, especially the 2-t-BOC derivatives which displayed complex splitting patterns reflecting two relatively stable conformations with ratios ranging from 5:2 to 5:4, similar to those observed for N-Ac and N-Me substituted tetrahydroisoquinolines,. Dalton, D. R.; Cava, M. P.; Buck, K. T. "Hindered rotation in 1-benzyl-1,2,3,4-tetrahydro-6,7-dimethoxyisoquinolines" *Tett. Lett.* 1965, 2687–2690; Tomita, M.; Shingu, T.; Fujitani, K.; Furikawa, H. "Studies on the alkaloids of menispermaceous plants. CCXVI. Nuclear magnetic resonance spectra of benzylisoquinoline derivatives. (1). N-Methylcoclaurine type bases" *Chem. Phar. Bull.* 1965, 13, 921–926. However, the $^{13}$C NMR spectra of 1-benzyl tetrahydroisoquinolines can be easily used for structure identification because of their relative simplicity. Assignments of signals (final compounds) were made based on the $^{13}$C-NMR spectra of salsolinol, Iwasa, K.; Kamigauchi, M.; Takao, N. "Metabolism of salsalinol by tissue cultures of some Papaveraceae" *Phytochemistry* 1991, 30, 2973–2975, on effects of substituents in benzene ring, and off-resonance spectra. For 2-TFA derivatives, the chemical shift of the C-3 atom appears as a quartet ($^4$J C-F≈3.7 Hz) indicating its close proximity to the $CF_3$ group.

It should be noted that all the compounds produced in the foregoing syntheses are racemic mixtures of the stereoisomers, with a site of asymmetry at $C_{10}$. It has been observed that the binding specificity and activity of the individual isomers will differ, with the (−) species generally the more specific and active as agonists. Typically, the difference will be relatively modest, and the values of the (+/−) racemic mixtures will be intermediate of the values of the individual isomers and are generally equivalent in their bioactivities to the isolated isomers. It is generally preferred to employ the racemic mixture for reasons of economy and simplicity of the synthesis, but the individual isomers are also a part of the present invention In suitable cases, the individual isomers can be isolated by stereospecific synthesis or by separatory techniques, both of which are per se known to those of ordinary levels of skill in the art.

Little has been published on the biochemical action of $\beta_3$-adrenoreceptor agonists and the behavior of these compounds in vivo is not entirely clear. What is clear is that the activity of these agents is dependent upon binding to the $\beta_3$-adrenoreceptor. It is also clear that affinity alone is not the sole consideration, as the compounds vary in their selectivity, some also binding $\beta_1$ adrenoreceptor and $\beta_2$ adrenoreceptor sites, producing unwanted side effects consistent with a role as agonists or blockers of those sites. They also vary in the degree of agonist activity when bound at the $\beta_3$-adrenoreceptor agonists site. The effect is at least analogous to adrenaline binding to the $\beta_3$-adrenoreceptor and the agonist activity provided by adrenaline, but in the present invention is more selective and substantially free of $\beta_1$ adrenoreceptor agonist or blocker activity, $\beta_2$ adrenoreceptor agonist or blocker activity, or TP agonist or blocker activity.

The mode of action of these agonists when bound at the $\beta_3$-adrenoreceptor site has not been fully characterized. Although there is no wish to be bound thereby, it is believed that the activation of the cellular mechanisms produced by the agonist activity is the same as that provided by adrenaline, which has been studied. No indications have been seen which are inconsistent with the adrenaline-like agonist behavior, except that the compounds of the present invention are far more selective for the $\beta_3$-adrenoreceptors and minimally bound to the $\beta_1$ adrenoreceptor and $\beta_2$ adrenoreceptor sites.

The action of the $\beta_3$-adrenoreceptor agonists of the present invention are also more persistent than the effect of adrenaline. The compounds appear to be less readily broken down in vivo, remain bound to the $\beta_3$-adrenoreceptor sites longer than does adrenaline, and continue to be active for a longer prior of time. It is known that the effects of adrenaline are very rapidly induced by the release of adrenaline into the circulation in response to a stimulus, and are nearly equally rapidly dissipated when the release of adrenaline is slowed to base levels in vivo. While these effects pass within seconds or at most a few minutes, the compounds of the present invention typically persist in their action for an interval of up to about two and often four hours.

As those of ordinary skill in the art will recognize, these features are consistent, in part, with the high binding affinities of the present compounds.

As in the case of adrenaline and other compounds observed to activate $\beta_3$-adrenoreceptors in vivo, the present compounds cause the breakdown of adipose tissue at the cellular level, and increase release of glucose into the circulation and, separately, suppress the conversion of carbohydrates into glucose in the liver. Excess levels of glucose in the blood stream are excreted, primarily in the urine, either per se or as "ketone bodies" produced in the liver. These mechanisms are well studied and characterized and do not form a part of the present invention. It is important in the case of diabetics to be aware of these effects and take them into account in the management of diabetes to avoid the assumption that these conditions are an exacerbation of the diabetes or a failure of the diabetes therapies.

The trimethoxybenzyl portion of trimetoquinol was modified by replacing one or more of the methoxy groups with a variety of halogenated substitutions. The effects of these modifications on the receptor binding affinity of trimetoquinol analogs (Table 1) for human $\beta_2$ adrenoreceptor, expressed in CHO cells and human TP receptors (platelets) were determined by radioligand competition binding assays using [$^{125}$I]-iodocynopindolol (ICYP) and [$^3$H] SQ 29548 as radioligands, respectively.

Most of the modifications made on the trimethoxybenzyl portion of trimetoquinol resulted in enhancement of $\beta_2$ Adrenoreceptor affinity. Previously, it was shown that replacement of the 3' and 5'-methoxy groups of trimetoquinol with iodines [i.e., 1 (pKi=7.36) 2 (pKi=8.69)] resulted in a more than 20-fold increase in affinity, Fraundorfer, P. F.; Fertel, R. H.; Miller, D. D.; Feller, D. R. "Biochemical and pharmacological characterization of high-affinity trimetoquinol analogs on guinea pig and human beta adrenergic receptor subtypes: evidence for partial agonism" *J Pharmacol Exp Ther* 1994, 270, 665–74. In the present study, complete replacement of the 3'-, 4'- and 5'-methoxy groups of trimetoquinol (1) with iodine atoms to give the triiodo analog 21b (pKi=8.82) enhanced $\beta_2$-adrenoreceptor affinity 29-fold versus trimetoquinol (1) but with respect to 2, the additional iodine substituent at the 4'-position adds little to the binding affinity.

Studies on human $\beta_2$ Adrenoreceptor indicate that 4'-position substituents of reflecting varying size and chemical properties are well tolerated. Replacement of the 4'-methoxy of 2 with an amino group [i.e., 2 ØØ21c (pKi=8.81)] did not significantly alter affinity, while replacement with a 4'-acetamido [i.e., 15 (pKi=8.06)] reduced affinity only 4-fold. A similar replacement with a hydroxy (i.e., 18, pKi=7.93) reduced affinity about 5-fold as compared to 2. The receptor binding pocket that interacts with substituents at the 4'-position seems to be sufficiently large to accommodate the 4'-benzamido moiety of 26b (pKi=8.70). Interestingly, the diiodo analog 21a (pKi=9.52), which lacks a 4'-substituent, exhibits the most potent affinity with a Ki value in the sub-nanomolar range.

It appears that one meta-iodo substituent is sufficient to retain high affinity since removing one of the iodo groups of either 21c or 15 [i.e., 21c ØØ24 (pKi=8.19) or 15 ØØ26a (pKi=8.11)] resulted in only minor shifts in affinity. To determine the nature (hydrophobic or electronic) of the binding contributions of 3' and 5'-substituents (methoxy and iodo), the bis-trifluoromethyl analog 27 was synthesized. While the hydrophobic property ($\pi$) of the trifluoromethyl group ($\pi$=0.88) is similar to iodine ($\pi$=1.12), this functional group exerts a much stronger electron withdrawing effect. The binding affinity of the bis-trifluoromethyl analog 27 (pKi=5.36) was five orders of magnitude lower than the diiodo analog 21a. Thus, trifluoromethyl substituents at the 3'- and 5'-positions abolish binding affinity. Since, a trifluoromethyl group is similar in size to an iodine atom, the significantly stronger electron withdrawing property of the trifluoromethyl ($\sigma_p$=0.54 versus $\sigma_p$=0.18 for iodine) is likely responsible for the greatly reduced binding affinity of 27. The electron withdrawing effect of the trifluoromethyl substituents on the $\pi$-electron system of the aromatic ring may interfere with its capability to form aromatic interactions with the receptor binding site. These aromatic interactions may be more important for binding than hydrophobic interactions.

Although replacement of the 3' and 5'-methoxy groups of trimetoquinol 1, with iodine atoms (i.e., 2) resulted in a 21-fold increase in $\beta_2$ adrenoreceptor affinity, a similar increase in binding affinity was not observed at $\beta_1$ adrenoreceptor (Table 2). As a result, the diiodo analog 2 exhibits moderate (ca. 40-fold) selectivity for $\beta_2$ adrenoreceptor versus $\beta_1$ adrenoreceptor. More importantly, the influence of a 4'-substituent is markedly different for $\beta_2$ adrenoreceptor versus $\beta_1$ adrenoreceptor. While the absence of a 4'-substituent (i.e., 21a) does not significantly alter $\beta_1$ Adrenoreceptor affinity (pKi=6.74), the same feature increased $\beta_2$ Adrenoreceptor affinity. Consequently, analog 21a displays more than 600-fold selectivity for $\beta_2$ Adrenoreceptor versus $\beta_1$ Adrenoreceptor, and is the most selective trimetoquinol analog yet reported. These results indicate a remarkable difference in the receptor binding site or pocket of $\beta_2$- and $\beta_1$ adrenoreceptor that interacts with substituents at the 4'-position of trimetoquinol analogs.

In general, replacement of the 3' and 5'-methoxy groups of trimetoquinol (1, pKi=6.79) with iodine to give analog 2 (pKi=7.33) resulted in only a slight increase (3-fold) in affinity. However, replacement of all three methoxy groups of trimetoquinol with iodines to give the triiodo analog 21b (pKi=4.22) practically abolished binding to TP receptors. In addition, demethylation of the 4'-methoxy substituent of 2 to give 18 (pKi=4.72) resulted in a similar 380-fold reduction in binding affinity. The very low binding affinity of 18 is in contrast to a recent observation, Christoff, J. J. "Part 1: Synthesis of arylalkylguanidines as dopamine agonists, Part 2, Section A: Modifications of trimetoquinol and the effects on beta-adrenergic and thromboxane $A_2$ receptor system, Section B: Approaches to the asymmetric synthesis of irreversibly binding iodinated derivatives of trimetoquinol." Ph. D. Thesis, The Ohio State University, 1993, where 6,7-dihydroxy-1-(4'-hydroxy-3'-nitrobenzyl)-1,2,3,4-tetrahydroisoquinoline exhibited good binding affinity. By contrast, substitution of the same methoxy group with an amino moiety (i.e. 21c, pKi=6.73) resulted in only a 3-fold decrease in affinity. Interestingly, removal of the 4-'substituent of 2 or 21c to give 21a (pKi=6.75) did not affect binding affinity significantly. Acetylation of the 4'-amino group of 21c was also tolerated as 15 (pKi=6.45) displayed binding affinity similar to 21c. Thus, while a primary amine, acetamide, or a methoxy group is tolerated at the 4'-position, a free hydroxy group or an iodo group is detrimental to binding affinity. Removal of one of the iodines of 21c and 15 to give 24 (pKi=6.00) and 26a (pKi=5.83), respectively, resulted in 5-fold decrease in binding affinity, suggesting that hydrophobic interactions of 3' or 5'-substituents contribute to binding. However, replacement of the 3' and 5'-iodo groups of 21a with similarly hydrophobic trifluoromethyl substituents resulted in drastic reduction in binding affinity. As with $\beta_2$ adrenoreceptor, in terms of contribution to overall binding affinity, hydrophobic interactions appear secondary to aromatic interactions.

Synthesis of Thiazolopyridine Derivatives

The preparation of 2-amino-4,5,6,7-tetrahydrothiazolo[5,4-c]pyridines has been well documented in the literature (Thomae, K. 4,5,6,7-Tetrahydrothiazolo[5,4-c]pyridines. Neth. Appl. 6 610 324, 1967; *Chem. Abstr.* 1968, 68, 49593p. Thomae, K. Analgesic Tetrahydrothiazolo[5,4-c] pyridines. Fr. Addn. 94 123, 1969; *Chem. Abstr.* 1970, 72, 100685g. Hantzsch, A.; Traumann, V. Amidothiazole aus Sulfoharnstoff und Halogenisirten Ketonen, resp. Aldehyden, *Berichte* 1888, 21, 938–941). They are constructed by two approaches: a) Pictet-Spengler reaction—the condensation and subsequent cyclization between an aldehyde and 2-(2'-amino-4'-thiazolyl)ethylamine derivatives; and b) Hantzsch thiazole synthesis—the condensation and subsequent cyclization between an α-bromopiperidone derivative and thiourea (FIG. 3).

FIG. 3

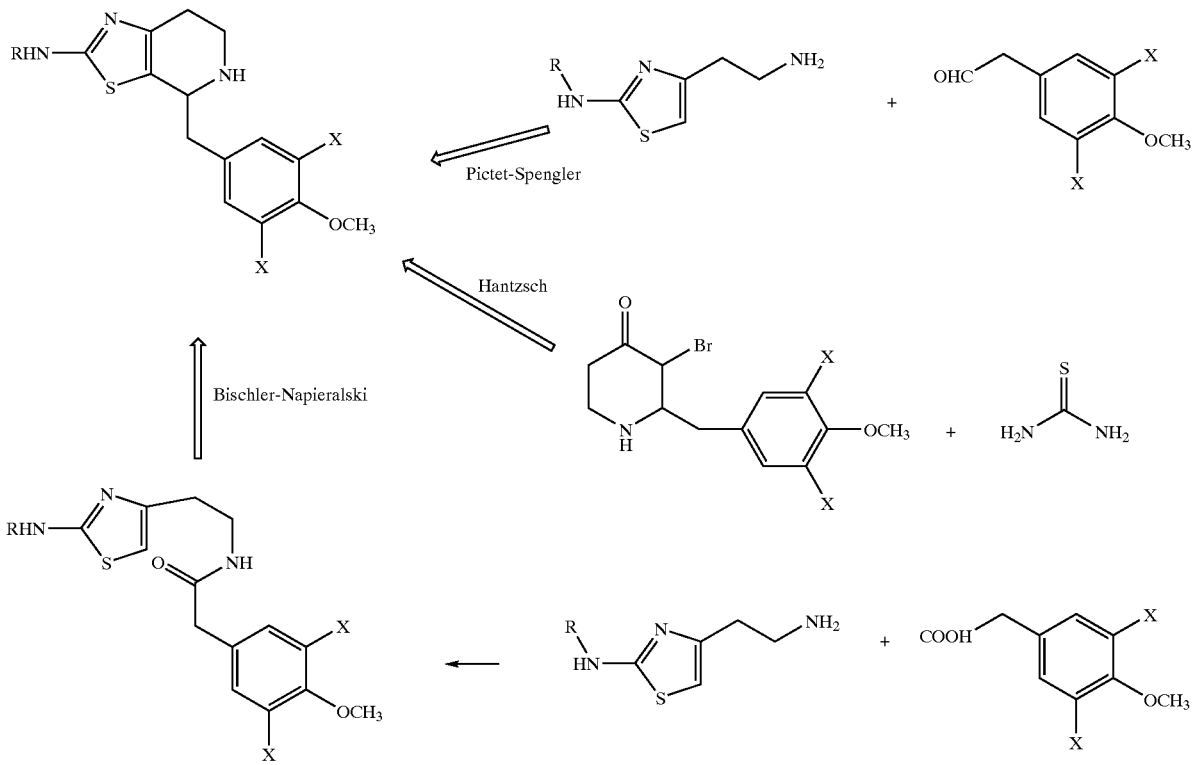

However, it was envisioned that both of these approaches would not meet our synthetic challenge. The Pictet-Spengler reaction would necessitate the use of an inherently unstable substituted phenylacetaldehyde whereas, the required α-bromopiperidone for Hantzsch thiazole synthesis is not readily accessible synthetically. Alternatively, the Bischler-Napieralski reaction (FIG. 3) is an attractive approach for the synthesis of our designed TMQ analogs, because the required substituted phenylacetic acids are stable, and readily accessible. The Bischler-Napieralski reaction is routinely used to prepare dihydroquinolines (Whaley, W. M.; Govindachari, T. R. The Preparation of 3,4-Dihydroisoquinolines and Related Compounds by the Bischler-Napieralski Reaction, *Org. React.* 1951, VI, 74–150).

According to Timmerman's synthetic scheme (Eriks, J. C.; Van der Goot, H.; Sterk, G. J.; Timmerman, H. Histamine H₂-Receptor Agonists. Synthesis, in Vitro Pharmacology, and Qualitative Structure-Activity Relationships of Substituted 4- and 5-(2-Aminoethyl)thiazoles, *J. Med. Chem.* 1992, 35, 3239–3246), compound 14, which is the starting amine for the Bischler-Napieralski approach has been prepared (Scheme 1).

Scheme 1

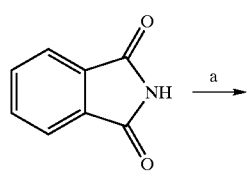

-continued

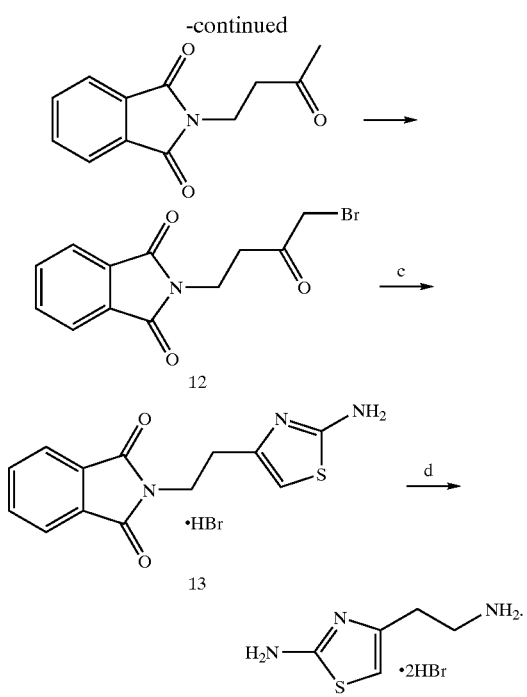

Scheme 1 (a) Methyl vinyl ketone, NaOEt, EtOH, EtOAc, r.t. → reflux; (b) (i) Br₂, MeOH, 0° C. → r.t., (ii) 10.0 M H₂SO₄, r.t.; (c) Thiourea, acetone, r.t.; (d) 30% HBr, reflux.

The transformation from 12 to 13 did not proceed in good yield as described. Instead, the procedure described by Sprague et al (Sprague, J. M.; Land, A. H.; Ziegler, C.

Derivatives of 2-Amino-4-methylthiazole, *J. Am. Chem. Soc.* 1946, 68, 2155–2159) converted 12 to 13 almost quantitatively.

Scheme 2 depicts the synthesis of analogs 7 and 9. Under the Schotten-Baumann condition, substituted phenylacetic acids 15 or 16 (Harrold, M. W.; Gerhardt, M. A.; Romstedt, K.; Feller, D. R.; Miller, D. D. Synthesis and Platelet Antiaggregatory Activity of Trimetoquinol Analogs as Endoperoxide/Thromboxane A₂ Antagonists, *Drug Des. Deliv.* 1987, 1, 193–207) was allowed to react with compound 14. The amide precursors 17 and 18 were obtained and each was treated with POCl₃ in refluxing acetonitrile, and the putative dihydro intermediate was reduced in situ with NaBH₄, giving final compounds 7 and 9 which were purified by crystallization or column chromatography on silica gel.

Scheme 2$^a$: $^a$ (a) Oxalyl chloride, dry benzene, 0° C. → r.t. → reflux; (b) 14, NaOH, CHCl₃, H₂O, r.t.; (c) POCl₃, CH₃CN, reflux; (d) NaBH₄, MeOH, 0° C. → r.t.; (e) 1.0 M HCl in Et₂O.

The acetamido analog 10 was prepared according to Scheme 3. Acetylation of 18 with acetic anhydride gave precursor 19 that was then subjected to POCl₃ and NaBH₄. Compound 10 was isolated as its maleic acid salt.

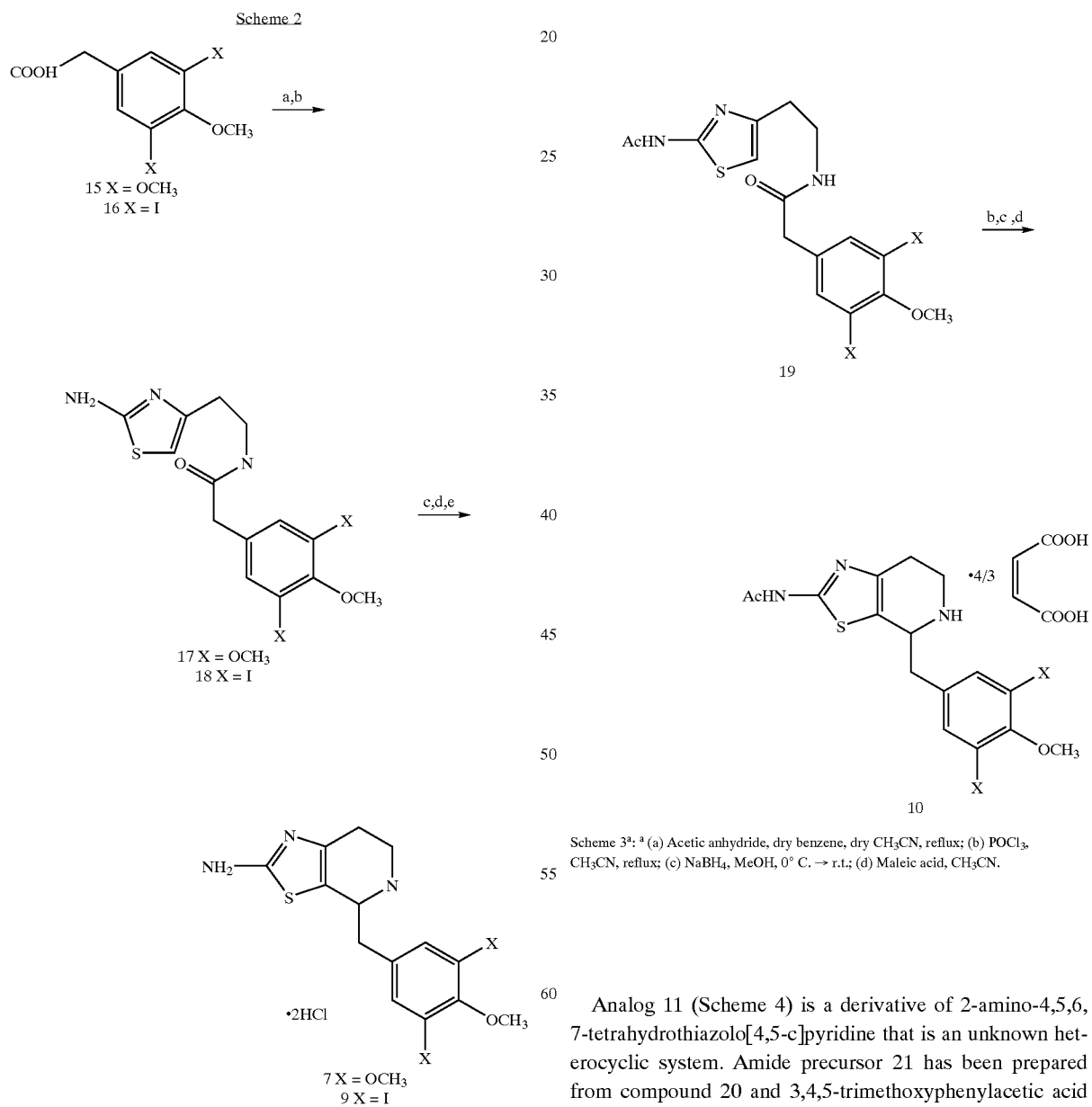

Scheme 3$^a$: $^a$ (a) Acetic anhydride, dry benzene, dry CH₃CN, reflux; (b) POCl₃, CH₃CN, reflux; (c) NaBH₄, MeOH, 0° C. → r.t.; (d) Maleic acid, CH₃CN.

Analog 11 (Scheme 4) is a derivative of 2-amino-4,5,6,7-tetrahydrothiazolo[4,5-c]pyridine that is an unknown heterocyclic system. Amide precursor 21 has been prepared from compound 20 and 3,4,5-trimethoxyphenylacetic acid under Schotten-Baumann condition.

Scheme 4

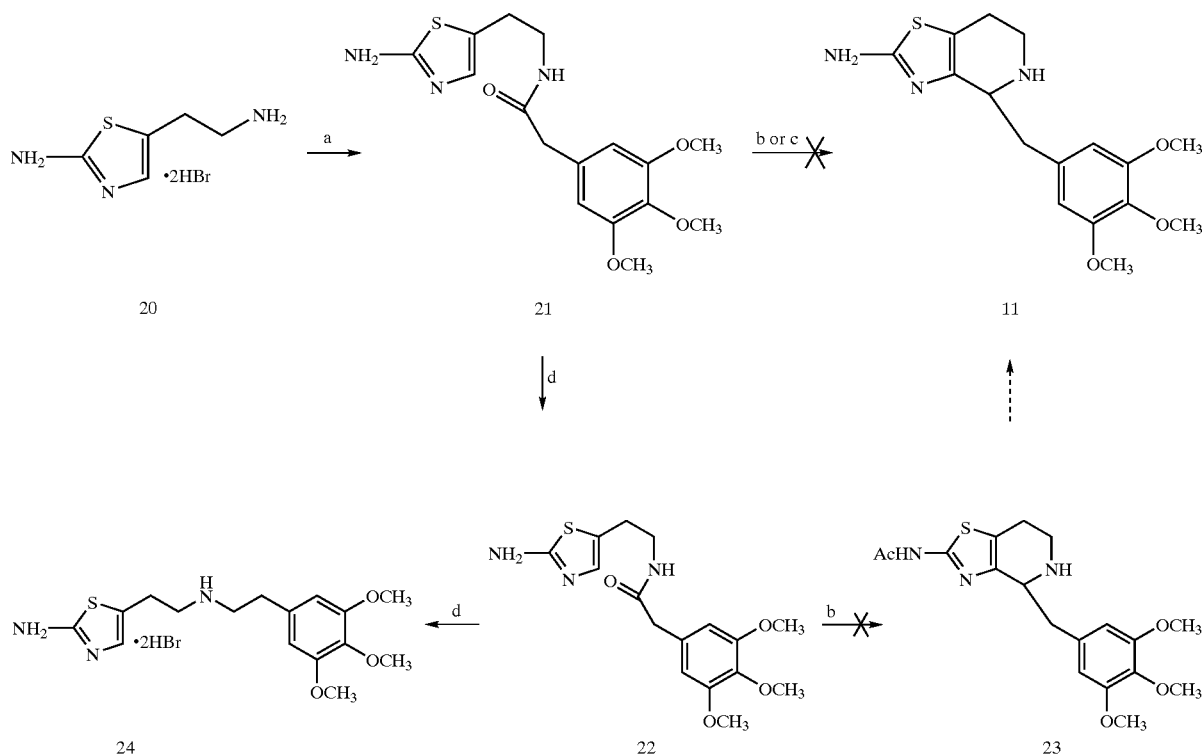

Scheme 4 (a) 3,4,5-Trimethoxyphenylacetyl chloride, NaOH, CHCl₃, H₂O, r.t.;
(b) (i) POCl₃, CH₃CN, reflux, (ii) NaBH₄, MeOH, 0° C. → r.t.; (c) P₂O₅, celite, dry CHCl₃, dry benzene, reflux; (d) Acetic anhydride, dry benzene, dry CH₃CN, reflux;
(e) (i) BH₃•THF, THF, 0° C. → r.t. → reflux, (ii) 1.0 M HCl in Et₂O.

Compound 20 was synthesized according to literature scheme (Scheme 5) (Eriks, J. C.; Van der Goot, H.; Sterk, G. J.; Timmerman, H. Histamine H₂-Receptor Agonists. Synthesis, in Vitro Pharmacology, and Qualitative Sturcture-Activity Relationships of Substituted 4- and 5-(2-Aminoethyl)thiazoles, *J. Med. Chem.* 1992, 35, 3239–3246).

Scheme 5

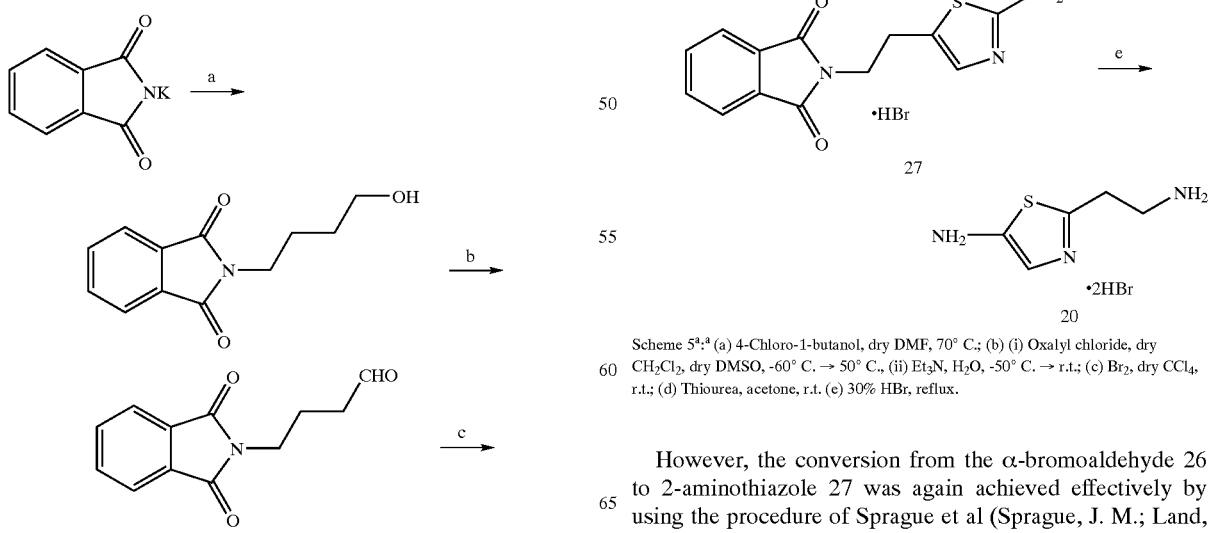

Scheme 5ª:ª (a) 4-Chloro-1-butanol, dry DMF, 70° C.; (b) (i) Oxalyl chloride, dry CH₂Cl₂, dry DMSO, -60° C. → 50° C., (ii) Et₃N, H₂O, -50° C. → r.t.; (c) Br₂, dry CCl₄, r.t.; (d) Thiourea, acetone, r.t. (e) 30% HBr, reflux.

However, the conversion from the α-bromoaldehyde 26 to 2-aminothiazole 27 was again achieved effectively by using the procedure of Sprague et al (Sprague, J. M.; Land, A. H.; Ziegler, C. Derivatives of 2-Amino-4-methylthiazole,

*J. Am. Chem. Soc.* 1946, 68, 2155–2159). Using various conditions (Whaley, W. M.; Govindachari, T. R. The Preparation of 3,4-Dihydroisoquinolines and Related Compounds by the Bischler-Napieralski Reaction, *Org. React.* 1951, VI, 74–150; Kametani, T.; Fukumoto, K.; Fujihara, M. Studies on the Syntheses of Heterocyclic Compounds. Part CDLIV. Abnormal Dienone-Phenol Rearrangement of Procularine, *J. Chem. Soc. Perkin Trans. I* 1972, 394–396; Rice, K. C.; Brossi, A. Expedient Synthesis of Racemic and Optically Active N-Norreticuline and N-Substituted and 6'-Bromo-N-norreticulines, *J. Org. Chem.* 1980, 45, 592–601) of Bischler-Napieralski reaction, attempts to cyclize the amide precursor 21 proved to be unsuccessful. However, it has been reduced by $BH_3$ to give the open chain analog 24 that has also been examined in all three human β-AR subtypes. Similarly, the acetamido amide precursor 22 also failed to give the cyclized product under the reaction condition described.

Competitive Binding Studies

The competitive binding studies indicate that the compounds of the present invention are reversibly bound and confirms that they are equilibrium competitive binding species, No evidence of covalent bonding or other non-equilibrium binding mechanisms to the receptor sites is seen.

Binding to the $β_1$ adrenoreceptor, $β_2$ adrenoreceptor and the TP receptor sites is low, indicating that few side effects associated with these receptors is observed.

Binding to other types of receptors is unlikely.

Biochemical actions other than those associated with $β_3$-adrenoreceptor binding and agonist activity are not observed. In particular, the compounds of the present invention exhibit low acute toxicities, low long-term subacute toxicity, no evidence of receptor down regulation or other loss of effectiveness over time, and no indications to date of adverse side reactions or side effects, short term or long term, which would represent contraindications for the indicated use.

The chemical properties and stability of the compounds permits their formulation into substantially any suitable vehicle or carrier consistent with the intended mode of administration. Those of ordinary levels of skill in the pharmaceutical industry are fully capable of devising appropriate carriers for the administration of the compounds consistent with the intended mode of administration, and such carriers are employed in the present invention, but are not per se an inventive part thereof.

The compounds of the present invention can be administered effectively by any route or modality consistent with the administration of water-soluble, polar pharmaceutical compounds. Administration may be oral, injectable (via im, iv, ip and subcutaneous, injections), or may be implanted for sustained release by employment of known implantable systems for the administration of bioactive agents. Absorption from suppositories is also effective, although generally limited by patient reluctance.

Topical administration is also effective, although provision must be made for a suitable skin transport agent to be associated with the compounds to assure that an effective level of the compounds are administered to provide useful systemic levels.

Oral administration and, in suitable cases, implantable sustained release systems are the preferred mode of administration. Implants are particularly effective for those with acute obesity, for those who are inconsistent and/or non-compliant with scheduled oral dosages, and related circumstances. For general usage, oral administration will ordinarily be preferred.

At the outset of administration, the compounds of the present invention produce marked weight loss in over-weight subjects, often at rates of greater than one pound per day and in acute subjects, at rates greater than two pounds per day. The rate is generally sustained until the level of adipose tissue is markedly reduced, and the loss of weight and fatty tissue slows until, at an equilibrium point which is directly related to dosage levels, the body weight of the subject stabilizes. The dosage level may require adjustment from time to time to attain a suitable equilibrium level, which may be suitably defined by the percentage of body fat, the "body mass index" as that term is generally defined in the medical literature, or by other known factors.

If the compounds of the present invention are withdrawn, unless "semi-permanent" metabolic changes are induced as hypothesized below, the benefits of the present invention will be lost over time, and the body weight and body fat will, unregulated, tend to return to its former level.

Substantially all the adverse effects of over-weight and obesity will be eliminated, or at the least be materially reduced, as the levels of fatty tissues and body mass are reduced.

The problems of glucose intolerance, insulin resistance and Type II diabetes (non-insulin dependent diabetes), in particular, will be reduced in magnitude or eliminated. In particular, the adverse and progressive effects of such conditions will generally be arrested, the risks of non-compliance with specific treatments and dietary management will be reduced or eliminated, and the causes of such conditions may, in some cases, be moderated or even reversed.

As body fat is reduced, and body mass is reduced, the load on joint in the body will be reduced, which may produce beneficial palliation of the effects of osteo-arthritis, rheumatoid arthritis and other joint disorders and sources of pain. Those having limited mobility associated with obesity will be better able to exercise and improved mobility can be expected to result.

In most uses, the present invention will produce improved psychological profiles in those concerned with body image and appearance. Such effects are virtually always healthy and beneficial developments.

As the level of body fat declines, and so long as serum levels of glucose are kept low, there will generally be an increase in the metabolism of dietary fat for the production of catabolic energy requirements. A decline in serum cholesterol, low density lipids, total serum lipids and related problems will occur. The anti-hypercholersteremic effect is a highly desirable consequence of the practice of the present invention. Such effects can be enhanced by a diet which limits carbohydrate intake. Over time, such effects may limit the progress of or even reduce arterial occlusion and the incidence of ischemic and related consequences, including, among others, stroke and myocardial infarction.

The increased reliance on dietary fats instead of carbohydrates, and particularly serum glucose, may become so substantial, in fact, that in some cases intake of dietary fats will need to be increased to support normal catabolic energy requirements.

It is hypothesized that, over a long term, the effect of the administration of the compounds of the present invention will so limit blood glucose and the conversion of blood glucose into fats that the body will undergo a "semi-permanent" metabolic change, with increased (up-regulated) insulin receptors, decreased glucose intolerance (increased insulin responsiveness and efficiency generally), and reduced (down-regulated) mechanisms for the conversion of glucose and other carbohydrates into adipose fat tissues. Increased reliance on dietary fat as energy sources for catabolic processes would continue with the alteration of glucose responses and the hypocholesterolemic effects would continue. These effects are not expected to occur until a suitable equilibrium state is attained, and will lag substantially behind body mass and fatty tissue reduction, and will arise only as mitosis produces new cells adapted to the equilibrium conditions, with environmentally "adjusted" receptor populations. These effects would be of particular benefit in preventing or treating Type 11 diabetes and glucose intolerance, in particular. These effects would alter the body mass equilibrium point in a fundamental fashion, and would require reducing the dosage of the compounds of the present invention and may, with suitable dietary modifications and other behavioral modification, permit weaning the subject from reliance on the compounds altogether.

All indications to date suggest that the $\beta_3$-Adrenoreceptor agonists of the present invention are fully effective modulators of body weight without reliance on adjunctive or combination therapies. When such additional modalities, such as dietary restrictions and/or exercise, are desirable for other reasons, or where the need for weight regulation and glucose modulation at the cellular level is needed in concert with treatment of other disorders, such as diabetes and the like, there is no evidence that the present compounds and the utilization thereof conflict in any way with such additional or adjunctive treatments and therapies.

In particular, the present compounds do not interfere with the administration of insulin or other agents to diabetic patients.

In addition, the present compounds are not inconsistent with special diets employed to regulate glucose intolerance, insulin intolerance and related disorders, including very low carbohydrate diets, very high protein diets, and the like.

Where appetite and eating disorders are factors, the modalities of the action of the present invention do not conflict with the usual and common treatments and therapies employed to control such conditions, including behavior modification, drug therapies and surgical interventions, although the present invention may in many cases eliminate the need to resort to such higher risk strategies and the problems and consequences thereof may often be regulated by the present invention without resort to such additional strategies. The present invention results in an intrinsic suppression of appetite, tends to trigger satiety and tends to modulate the factors which promote appetite and eating disorders, and is likely, over time, to result in substantial behavior modification as the causes of such disorders are modulated. The use of appetite suppression is generally not indicated or required with the present invention.

In general, when the compounds of the present invention are administered, it is highly desirable to assure a balanced diet and adequate intake of vitamins and minerals. The nature of the action of the compounds of the present invention can accelerate the excretion of both oil soluble and water soluble vitamins and of minerals. In addition, it is advisable to maintain high fluid intake to aid in the excretion of the high levels of glucose to be eliminated via the kidneys.

It is also appropriate in many cases to induce a suitable exercise program to improve muscle tone, strength, mobility and agility in parallel with the practice of the present invention. While many overweight individuals exercise considerably, many more do not. The compounds of the present invention do not increase muscle strength or endurance, although the user will benefit from the reduced body mass and the attendant load the muscles must carry, so that greater endurance and "perceived strength" or "relative strength" may increase and increased activity levels and exercise levels will often be a desirable side benefit of the practice of the invention.

Particularly those with limited joint functionality as an incident of arthritic conditions and other like causes will find substantial palliation and increased joint functionality as adipose tissue and body mass are reduced and the load on the joints is reduced as a consequence.

The loss of body bulk may provide enhanced joint flexibility and increased range of motion in some subjects who have been limited by obesity.

No absolute contraindications or adverse side effects of the compounds of the present invention have been found to date.

Those with impaired liver or kidney function may face adverse consequences from the increased levels of glucose in the circulation and the increased load on the blood glucose processing and excretion. Such individuals may require reduced dosages (and more gradual effects) to limit the loading on the liver and kidneys. The invention has not, to date, been tested with individuals with partially or totally incompetent kidneys, i.e. kidney deficient dialysis patients, but it appears that the present invention is not likely to exacerbate either the conditions which require reliance on dialysis or the risks of dialysis procedures themselves.

These compounds do not significantly bind or activate the $\beta_1$ adrenoreceptor or the $\beta_2$ adrenoreceptor and thus do not produce the usual responses of agonists or blockers for these sites. There is no indication of significant or measurable binding to $\alpha$-adrenoreceptors, and no indication of any activity consistent with such agonist or blocking activity. There is accordingly no hypertensive effect, no vasodilator effect, and no bronchodilator effect observed in connection with the administration of the compounds of the present invention. These observations are, of course, consistent with the high level of selectivity of these compounds for the $\beta_3$-Adrenoreceptors.

EXAMPLES

The following specific examples demonstrate and illustrate the synthesis of the compounds of the present invention and intermediates prepared in the course of the synthesis. The following apply to all the examples related to the syntheses of compounds:

Melting points were determined on a Thomas-Hoover capillary melting point apparatus and are uncorrected. Infrared spectra were recorded on a Perkin Elmer System 2000 FT-IR. Proton and carbon-13 magnetic resonance spectra were obtained on a Bruker AX 300 spectrometer (300 and 75 MHz for $^1$H and $^{13}$C, respectively). Chemical shift values are reported as parts per million ($\delta$) relative to tetramethylsilane (TMS). Spectral data are consistent with assigned structures. Elemental analyses were performed by Atlantic Microlab Inc., Norcross, Ga., and found values are within 0.4% of the theoretical values. Routine thin-layer chromatography (TLC) was performed on silica gel GHIF plates (250 m, 2.5×10 cm; Analtech Inc., Newark, Del.). Flash chromatography was performed on silica gel (Merck, grade 60, 230–400 mesh, 60 Å). Tetrahydrofuran (THF) was dried by distillation from sodium metal, and acetonitrile (MeCN), CHCl$_3$ and methylene chloride (CH$_2$Cl$_2$) were dried by distillation from $\beta_2$O$_5$. All anhydrous solvents (except anhydrous Et$_2$O and THF) were stored over 3- or 4-Å molecular sieves.

TMQ Derivatives

Example 1
N-(3,4-dimethoxyphenethyl)-4-nitrophenylacetamide

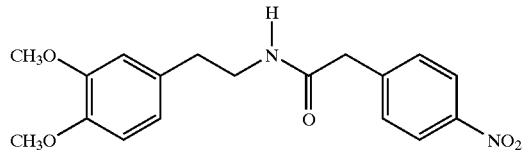

A solution of 3,4-dimethoxyphenethylamine (5.0 g, 27.6 mmol) and 4-nitrophenylacetic acid (7.5 g, 41.4 mmol) in toluene (150 mL) was heated at reflux for 72 h in a flask equipped with a Dean-Stark trap under an argon atmosphere. The solvent was evaporated in vacuo and the residue was taken up in $CH_2Cl_2$ (200 mL). The solution was washed consecutively with $H_2O$ (100 mL), 10% HCl (2×100 mL), $H_2O$ (2×100 mL), 10% $NaHCO_3$ (2×200 mL), $H_2O$ (2×100 mL) and dried over $MgSO_4$. The solvent was evaporated and the crude solid was recrystallized from EtOAc to give 5.49 g (58%) of the product as ivory colored needles: mp 119–121° C. (lit.[22] 130–132° C., ethanol-isopropanol); $^1$H NMR ($CDCl_3$) δ8.16 (d, J=8.8 Hz, 2H, ArH), 7.37 (d, J=8.8 Hz, 2H, ArH), 6.73 (d, J=8.1 Hz, 1H, ArH), 6.65 (d, J=1.9 Hz, 1H, ArH), 6.60 (dd, J=8.1 & 1.9 Hz, 1H, ArH), 5.40 (m, 1H, NH), 3.86 (s, 3H, OMe), 3.84 (s, 3H, OMe), 3.59 (s, 2H, $CH_2$), 3.51 (q, J=6.9 Hz, 2H, $CH_2$), 2.73 (t, J=6.9 Hz, $CH_2$); IR (KBr) 3320 (NH), 1650 (C=O) cm$^{-1}$; Anal. ($C_{18}H_{20}N_2O_5$) C, H, N.

Example 2
N-(3,4-dimethoxyphenethyl)-3,5-bis-trifluoromethylphenylacetamide

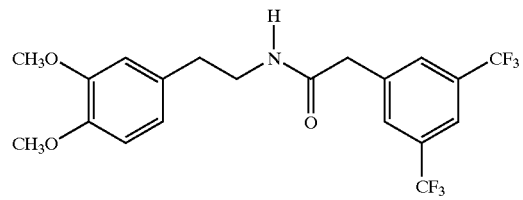

A solution of 3,4-dimethoxyphenethylamine (2.72 g, 15 mmol) and 3,5-bis-trifluoromethylphenylacetic acid (2.72 g, 10 mmol) in toluene (50 mL) was heated at reflux for 80 h in a flask equipped with a Dean-Stark trap. The solvent was evaporated in vacuo and the residue was taken up in $CH_2Cl_2$. The solution was washed consecutively with 0.1 N HCl (30 mL), $H_2O$ (50 mL), 0.1 N NaOH (30 mL), $H_2O$ (50 mL) and dried over $MgSO_4$. The solvent was evaporated and the crude solid was recrystallized from toluene to give 3.44 g (79%) of the product as white needles: mp 127–128° C.; $^1$H NMR ($CDCl_3$) δ7.79 (s, 1H, ArH), 7.72 (s, 2H, ArH), 6.75 (d, J=8.1 Hz, 1H, ArH), 6.67 (d, J=1.9 Hz, 1H, ArH), 6.61 (dd, J=8.1 & 1.9 Hz, 1H, NH), 3.85 (s, 3H, OMe), 3.84 (s, 3H, OMe), 3.58 (s, 2H, $CH_2$), 3.52 (q, J=6.9 Hz, 2H, $CH_2$N), 2.75 (t, J=6.9 Hz, $CH_2$); $^{13}$C NMR ($CDCl_3$) δ168.72, 149.20, 147.87, 137.28, 131.90, 130.79, 129.47, 123.16, 121.20, 120.56, 111.72, 111.27, 55.83, 42.85, 40.90, 34.97; IR (KBr) 3323 (NH), 1651 (C=O) cm$^{-1}$; Anal. ($C_{20}H_{13}F_6NO_3$) C, H, N.

Example 3
6,7-Dimethoxy-1-(4-nitrobenzyl)-1,2,3,4-tetrahydroisoquinoline

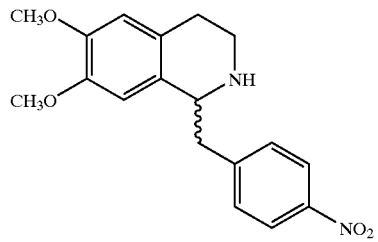

A mixture of 5a (8.0 g, 23.2 mmol) and $POCl_3$ (15.6 mL, 167.4 mmol) in dry MeCN (160 mL) was heated at reflux for 4 hours. The solvent was evaporated in vacuo to give a glassy residue which was taken up in methanol (250 mL) and evaporated to dryness three times until the residue was a solid. The solid residue was dissolved in MeOH (250 mL) then cooled in an ice bath. Excess $NaBH_4$ (17.56 g, 167.4 mmol) was carefully added in portions. The mixture was stirred at room temperature overnight. The solvent was removed in vacuo and the solid residue was partitioned in $CH_2Cl_2$ (250 mL) and $H_2O$ (150 mL). The layers were separated and the $H_2O$ layer was extracted with $CH_2Cl_2$ (100 mL). The combined organic fraction was washed successively with $H_2O$ (2×50 mL), 2N NaOH (2×50 mL), $H_2O$ (50 mL), and dried with $Na_2SO_4$. The solvent was evaporated to give a reddish oil. The oil was taken up in a minimum amount of methanol. The product crystallized upon standing and was collected by filtration (3.02 g, 40%): mp 134–36° C.; $^1$H NMR ($CDCl_3$) δ8.18 (d, J=8.7 Hz, 2H, ArH), 7.43 (d, J=8.7 Hz, 2H, ArH), 6.62 (s, 1H, ArH), 6.61 (s, 1H, ArH), 4.44 (dd, J=9.5, 4.1 Hz, ArCH—N), 3.87 (s, 3H, OMe), 3.84 (s, 3H, OMe), 3.28 (dd, J=13.7, 4.1 Hz, 1H, ArCH$_2$), 3.23–3.15 (m, 1H, NCH), 3.04 (dd, J=13.7, 9.5 Hz, 1H, ArCH), 3.00–2.91 (m, 1H, NCH), 2.71 (m, 2H, ArCH$_2$); Anal. ($C_{18}H_{20}N_2O_4$) C, H, N.

Example 4
6,7-Dimethoxy-1-(3,5-bis-trifluoromethybenzyl)-1,2,3,4-tetrahydroisoquinoline hydrochloride

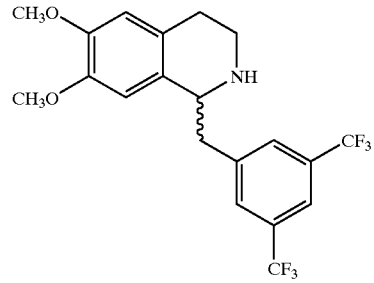

The amide 5c (1.31 g, 3 mmol) was cyclized in the same manner as 6a (7 mL of 1M HCl in ether was added to the methanolic solution of a crude product) to give 6c (0.84 g, 60%) as a hydrochloride salt: mp 104–115° C. (MeOH-ether); $^1$H NMR ($CDCl_3$) δ10.34 (bs, 2H, NH), 7.82 (s, 1H, ArH), 7.75 (s, 2H, ArH), 6.61 (s, 1H, ArH), 5.87 (s, 1H, ArH), 4.77 (m, 1H, CH), 3.91 (m, 1H, CH), 3.84 (s, 3H, OMe), 3.47 (s, 3H, OMe), 3.44 (m, 2H, CH), 3.28 (m, 2H, CH), 3.02 (m, 1H, CH); $^{13}$C NMR ($CDCl_3$) δ149.29, 147.74, 138.74, 132.08, 130.39, 123.33, 123.07, 121.40, 111.71, 109.43, 55.92, 55.38, 54.94, 40.46, 38.30, 24.80; IR (KBr)

Example 5
6,7-Dimethoxy-1-(4-nitrobenzyl)-2-trifluoroacetyl-1,2,3,4-tetrahydroisoquinoline

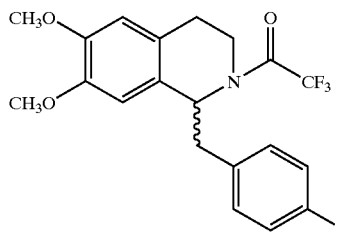

A solution of 6,7-dimethoxy-1-(4-nitrobenzyl)-1,2,3,4-tetrahydrisoquinoline (6a) (3.0 g, 9.14 mmol) in dry THF (150 mL) was added to trifluoroacetic anhydride (20 mL) with stirring at 0° C. The mixture was stirred at room temperature overnight with the flask equipped with a $CaCl_2$ drying tube. The reaction mixture was poured onto ice (200 g) and the mixture stirred for 30 minutes. $CH_2Cl_2$ (200 mL) was added and stirring was continued for 10 minutes. The layers were separated and the organic layer was washed consecutively with $H_2O$ (50 mL), 0.2N NaOH (100 mL), $H_2O$, (100 mL), and then dried with $Na_2SO_4$. The solvent was evaporated in vacuo to give a yellow solid. Recrystallization from EtOAc-MeOH gave 1.94 g (50%) of yellow crystals: mp 162–64° C.; $^1$H NMR (CDCl$_3$) δ8.14 (m, 2H, ArH), 7.28 (m, 2H, ArH), 6.62 (s, 1H, ArH), 6.34 (s, 1H, ArH), 5.64 (t, J=6.7 Hz, ArCH—N), 3.87 (s, 3H, OMe), 3.72 (s, 3H, OMe), 3.3–3.6 (m, 2H, N-CH$_2$), 3.25 (d, 2H, ArCH$_2$), 2.98–2.6 (m, 2H, ArCH$_2$); IR (KBr) 1686 (C=O), 1519, 1340 (NO$_2$) cm$^{-1}$; MS m/e (m$^+$): 423 (M+H, FAB). Anal. ($C_{20}H_{19}F_3N_2O_5$) C, H, N.

Example 6
6,7-Dibenzyloxy-2-tert-butoxycarbonyl-1-(4-nitrobenzyl)-1,2,3,4-tetrahydroisoquinoline

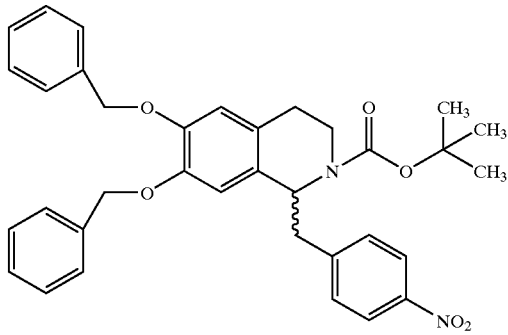

A solution of (Boc)$_2$O (2.84 g, 13 mmol) in THF (10 mL) was added to a cold mixture (ice bath) of isoquinoline 6b (6.20 g, 12 mmol) in THF (100 mL) and 1N NaOH solution (30 mL). The ice bath was removed and stirring was continued at room temperature overnight. THF was evaporated under reduced pressure, water was added and the product was extracted with $CH_2Cl_2$, dried over $MgSO_4$, filtered and evaporated again. The oily residue was dissolved in ether and put in a refrigerator. Pink crystals were filtered and washed with ether to give 6.00 g (86%) of the title compound: mp 150–152° C.; $^1$H NMR (CDCl$_3$) δ(the spectrum consists of two rotamers of 5:4 ratio) 8.11 and 8.06 (d, J=8.2 Hz, 2H, ArH), 7.47–7.27 and 7.21–7.11 (m, 12H, ArH), 6.70 and 6.67 (s, 1H, H-5), 6.56 and 6.44 (s, 1H, ArH), 5.27–4.96 (m, 5H, CH$_2$O+CH), 4.12 and 3.74 (m, 1H, CH), 3.25–3.00 (m, 3H, CH, CH$_2$Ar), 2.87-2-60 (m, 1H, CH), 2.57–2.37 (m, 1H, CH), 1.38 and 1.25 (s, 9 H, t-Bu); IR (KBr) 1688 (C=O), 1518, 1345 (NO$_2$) cm$^{-1}$. Anal. ($C_{35}H_{36}N_2O_6$) C, H, N.

Example 7
1-(4-Aminobenzyl)-6,7-dimethoxy-2-trifluoroacetyl-1,2,3,4-tetrahydroisoquinoline

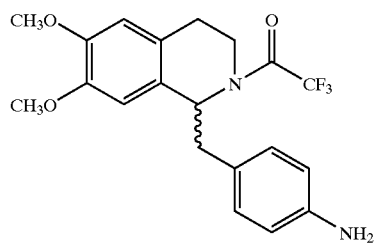

A solution of 7a (5.20 g, 12.24 mmol) in ethyl acetate (200 mL) was hydrogenated (60 psi) over 5% Pd/C (1 g) for 2 hours. The catalyst was removed by filtration and the filtrate was evaporated to dryness to give a beige solid. Recrystallization from ethyl acetate and hexane gave 4.20 (87%) of the product as light pink to white crystals: mp 157–160° C.; $^1$H NMR (CDCl$_3$) δ6.88 (d, 2H, ArH), 6.59(d, 3H, ArH), 6.32 (s, 1H, ArH), 5.53 (t, 1H, ArCH—N), 3.99 (m, 1H, CH), 3.86 (s, 3H, OMe), 3.71 (s, 3H, OMe), 3.60 (bs, 2H, NH$_2$), 3.42–3.56 (m, 2H, CH), 2.85–3.20 (m, 3H, CH), 2.59–2.73 (m, 1H, CH); IR (KBr) 3370 (m, NH$_2$), 1689 (C=O) cm$^{-1}$; MS m/e (m+): 395 (M+H, FAB). Anal. ($C_{20}H_{21}F_3N_2O_3$)C, H, N.

Example 8
1-(4-Aminobenzyl)-6,7-dibenzyloxy-2-tert-butoxycarbonyl-1,2,3,4-tetrahydroisoquinoline

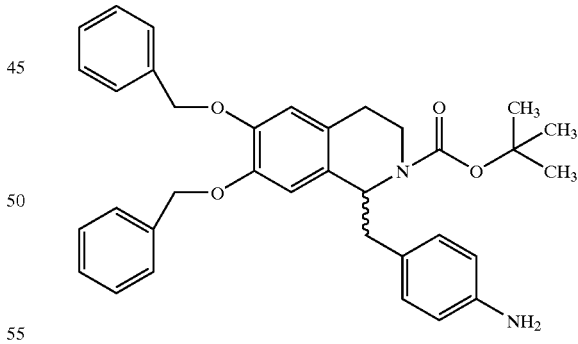

The nitro compound 7b (6.00 g, 10.3 mmol) was dissolved in EtOAc (230 mL) in a Parr bottle. The solution was charged with a slurry of Raney-Ni (4 mL) and hydrogenated at 50 psi for 3 h. The solution was filtered through celite and evaporated to give 5.10 g (90%) of the crude compound. The product was purified by flash chromatography (silica gel, hexane-EtOAc 2:1) to give a foamy glassy solid (4.51 g, 71%); $^1$H NMR (CDCl$_3$) δ(the spectrum consists of 2 rotamers of 5:2 ratio) 7.48–7.24 (m, 10H, 2×Ph), 6.82 (m, J=8.2 Hz, ArH), 6.68 and 6.64 (s, 1H, ArH), 6.58 (m, J=8.2 Hz, 2H, ArH), 6.49 and 6.32 (s, 1H, ArH), 5.12–4.81 (m, 5H, 2×CH₂O+CH), 4.18–4.08 and 3.81–3.71 (m, 1H, CH), 3.27–3.09 (m, 1H, CH), 3.00–2.60 (m, 3H, CH₂Ar), 2.59–2.40 (m, 1H, CH), 1.43 and 1.32 (s, 9H, t-Bu); IR (KBr) 3451 and 3365 (NH₂), 1684 (C=O), 1624 (NH bend), 1517 (C=C Ar) cm⁻¹. Anal. (C₃₅H₃₈N₂O₄) C, H, N.

Example 9
1-(4-Amino-3-iodobenzyl)-6,7-dibenzyloxy-2-tert-butoxycarbonyl-1,2,3,4-tetrahydroisoquinoline

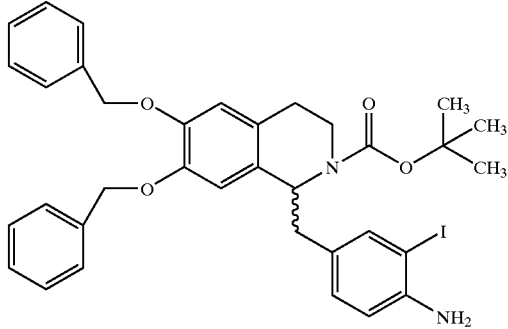

A mixture of isoquinoline 8b (1.11 g, 3.2 mmol), BTMACl₂I (1.1 g, 3.2 mmol), CaCO₃ (0.44 g, 4.4 mmol) in CH₂Cl₂ (50 mL) and MeOH (20 mL) was stirred overnight at room temperature. CaCO₃ was filtered and washed with CH₂Cl₂. The filtrate was washed with solution of Na₂S₂O₃ (×2), H₂O (×2), dissolved in CHCl₃ and EtOH and concentrated till the beginning of crystallization to give 1.59 g (81%) of title compound as pink crystals: mp 169–171° C.; ¹H NMR (CDCl₃) δ(the spectrum consists of 2 rotamers of 2:1 ratio) 7.47–7.25 (m, 11H, ArH), 6.81 (dd, J=8.1, J=1.6 Hz, 1H, ArH), 6.70–6.59 (m, 2H, ArH), 6.49 and 6.30 (s, 1H, ArH), 5.20–5.85 (m, 5H, CH₂O+CH), 4.13 and 3.74 (m, 1H, CH), 4.01 (s, NH₂), 3.30–3.10 (m, 1H, CH), 2.96–2.59 (m, 3H, CH₂Ar+CH), 2.59–2.43 (m, 1H, CH), 1.44 and 1.32 (s, 9H, t-Bu); IR (KBr) 3453 and 3334 (NH₂), 1667 (C=O), 1627 (NH bend), 1520 and 1498 (C=C Ar) cm⁻¹. Anal. (C₃₅H₃₇IN₂O₄) C, H, N.

Example 10
1-(4-Amino-3,5-diiodobenzyl)-2-trifluoroacetyl-6,7-dimethoxy-1,2,3,4-tetrahydroisoquinoline

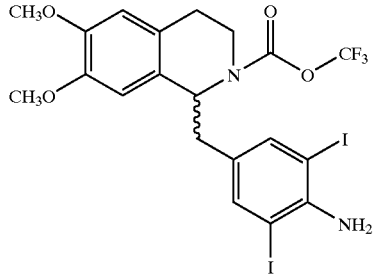

To a solution of 8a (0.1 g, 2.54 mmoL) in CH₂Cl₂ (50 mL) and methanol (20 mL) was added BTMACl₂I (2.0 g, 5.77 mmoL) and CaCO₃ (2.0 g). The mixture was stirred overnight at room temperature. A second portion of BTMACl₂I (0.97 g, 2.8 mmol) was added and stirring was continued overnight. Analysis of the reaction indicated a mixture of mono- and diiodinated products. The reaction mixture was filtered. The filtrate was washed consecutively with aqueous 5% Na₂S₂O₃ (40 mL) and water (50 mL), then dried with Na₂SO₄. Evaporation of the solvent gave a reddish glassy solid. The desired diiodinated product was purified from the crude mixture by flash chromatography (CH₂Cl₂:EtOAc, 9:1). The appropriate fractions were combined and evaporated in vacuo to give 0.72 g (44%) of the product as a white solid: mp 183–184.5° C.; 1H NMR (CDCl₃) δ7.37 (s, 2H, ArH), 6.61 (s, 1H, ArH), 6.29 (s, 1H, ArH), 5.43 (m, 1H, ArH), 4.56 (bs, 2H, NH₂), 3.87 (s, 3H, OMe), 3.73 (s, 3H, OMe), 3.60 (m, 1H, CH), 2.91 (m, 4H, CH), 2.70 (m, 1H, CH); IR (KBr) 3429, 3348 (NH), 1685 (C=O) cm⁻¹; Anal. (C₂₀H₁₉F₃I₂N₂O₃) C, H, N.

Example 11
4',4"-Azobis[1-(4-Amino-3,5-diiodobenzyl)-6,7-dimethoxy-2-trifluoroacetyl-1,2,3,4-tetrahydroisoquinoline]

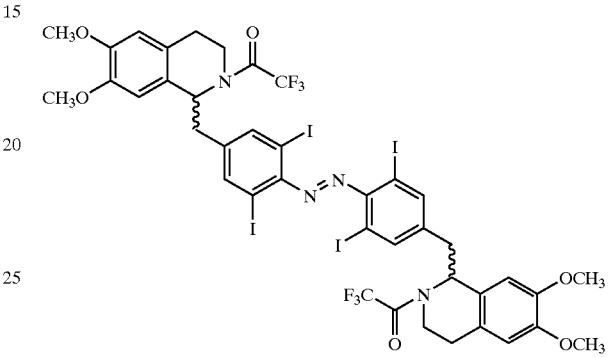

Was isolated from the above mixture as a bottom spot, deep-purple solid: mp 229–232° C.; 1H NMR (CDCl₃) δ7.78 (s, 2H, ArH), 6.65 (s, 1H, ArH), 6.18 (s, 1H, ArH), 5.53 (dd, J=7.9, 5.6 Hz, 1H, ArH), 3.99 (m, 1H, CH), 3.88 (s, 3H, OMe), 3.74 (m, 1H, CH), 3.72 (s, 3H, OMe), 3.16 (dd, J=13.0, 5.3 Hz, 1H, CH), 2.96 (m, 2H, CH), 2.80 (dt, J=16.2, 4.5 Hz, 1H, CH); ¹³C NMR (CDCl₃) δ156.14, (q) 148.89, 148.54, 147.59, 142.27, 141.53, 125.60, 125.05, 116.47 (q), 111.28, 110.42, 89.83, 56.15, 56.01, 55.54, 40.88 (q), 40.60, 28.45; IR (KBr) 1688 (C=O), 1520 (C=C Ar) cm⁻¹; Anal. (C₄₀H₃₄F₆I₄N₄O₆) C, H, N.

The same product was obtained via diazotization of 10a (0.32 g, 0.5 mmol, see below) and stirring overnight with 20 mL of 6% H₂SO₃ at room temperature, yield 0.03 g (10%) after flash column chromatography.

Example 12
4',4"-Azobis[1-(4-Amino-3,5-diiodobenzyl)-6,7-dimethoxy-1,2,3,4-tetrahydroisoquinoline]

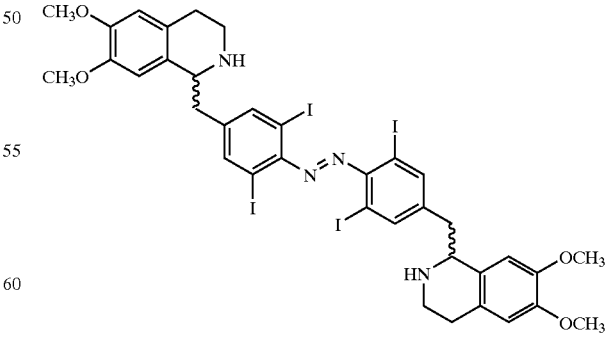

A solution of azo-compound 11 (0.26 g, 0.2 mmol) in 35 mL of MeOH and 0.85 g of K₂CO₃ in 11 mL was refluxed for 4 h and evaporated. Flash chromatography on silica gel (CH₂Cl₂, CH₂Cl₂-MeOH 50:1, 30:1) gave 0.15 g (70%) of the product, mp 176–177° C. (dec.); 1H NMR (300 MHz, CDCl₃) δ7.96 (s, 2H, ArH), 6.62 (s, 1H, ArH), 6.61 (s, 1H, ArH), 4.20 (dd, J=9.6, 4.0 Hz, 1H, ArH), 3.87 (s, 3H, OMe), 3.86 (s, 3H, OMe), 3.10–3.30 (m, 2H, CH), 3.00 (m, 1H, CH), 2.68–2.90 (m, 2H, CH); ¹³C NMR (CDCl₃) δ148.43, 147.75, 147.21, 144.05, 141.87, 129.76, 127.43, 112.03, 109.34, 90.43, 56.61, 56.16, 55.88, 41.65, 40.51, 29.36; IR (KBr) 1515 (C=C, Ar) cm⁻¹; Anal. (C₃₆H₃₆I₄N₄O₄) C, H, N.

Example 13
1-(4-Acetamido-3,5-diiodobenzyl)-6,7-dimethoxy-2-trifluoroacetyl-1,2,3,4-tetrahydroisoquinoline

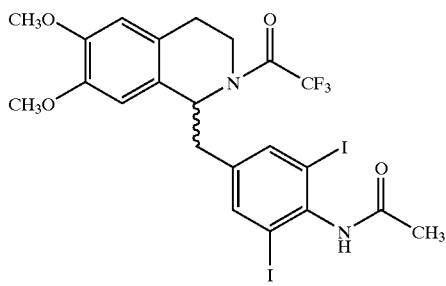

A solution of acetyl chloride (0.80 g, 7.8 mmol) in dry THF (2 mL) was added dropwise to a stirred solution of 10a (1.0 g, 1.56 mmol), Et₃N (0.40 g, 7.8 mmol), and N,N-dimethylaminopyridine (DMAP, @10 mg) in dry THF (20 mL) at 0° C. under an argon atmosphere. After the addition the reaction mixture was allowed to warm to room temperature and stirring was continued overnight (14 h). The reaction was quenched with H₂O (20 mL) and stirred for 30 min. The solution was extracted with Et₂OAc (3×75 mL). The organic extract was washed with H₂O (20 mL), dried (Na₂SO₄) and evaporated in vacuo to give a tan solid. Recrystallization of the crude product from EtOH and H₂O gave 0.93 g (87%) of the title compound as light beige needles: mp 218–219° C.; ¹H NMR (CDCl₃) δ7.5–7.75 (bm, 2H, ArH), 6.96 (s, 1H, CONH), 6.62 (s, 1H, ArH), 6.24 (s, 1H, ArH), 5.47 (t, J=6.7 Hz, 1H, CH)3.98 (m, 1H, CH), 3.87 (s, 3H, OMe), 3.73 (s, 3H, OMe), 2.83–3.18 (m, 4H, CH), 2.74, (m, 1H, CH), 2.22 (s, 3H, Ac); ¹³C NMR (CDCl₃) δ168.14, 156.02, (q), 148.39, 147.68, 140.58, 140.31, 139.35, 125.71, 124.85, 116.4 (q), 98.73, 56.09, 55.93, 55.44, 40.63 (q), 40.48, 28.43, 23.62 IR (KBr) 3387 (NH), 1683 (CO). Anal. (C₂₂H₂₁F₃I₂N₂O₄) C, H, N.

Example 14
1-(4-Acetamido-3,5-diiodobenzyl)-6,7-dimethoxy-1,2,3,4-tetrahydroisoquinoline Hydrochloride

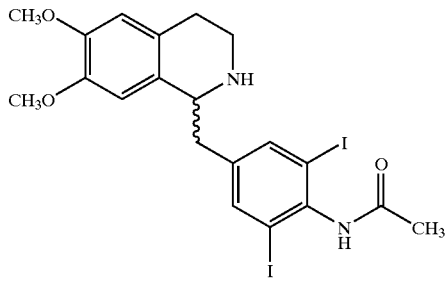

A solution of 13 (1.22 g, 1.78 mmol) in methanol (60 mL) was added to a solution of K₂CO₃ (5.6 g) in 80 mL of 1:1 methanol and water. The mixture was stirred at room temperature for 3 hours. The resulting solution was concentrated then extracted with ethyl acetate (3×80 mL). The organic solution was dried (Na₂SO₄) and evaporated in vacuo to give the 0.79 g (75%) of the product as the free base. The free base converted to the hydrochloride salt and recrystallized from anhydrous ethanol and ethyl ether: mp 196–200° C. (dec); ¹H NMR (DMSO-D₆) δ9.85 (s, 1H, CONH), 9.35 (bm, 2H, NH⁺), 7.98 (s, 1H, ArH), 7.96 (s, 1H, ArH), 6.78 (s, 1H, ArH), 6.65 (s, 1H, ArH), 4.65 (bm, 1H, CH), 3.83 (s, 3H, OMe), 3.73 (s, 3H, OMe) 3.35–3.43 (m, 1H, CH), 2.8–3.2 (m, 5H, CH), 2.01 (s, 3H, Me); IR (KBr) 1677 (C=O), 1514 (C=C Ar) cm⁻¹; MS m/e (m+): 592 (M—HCl, El). Anal. (C₂₀H₂₂I₂N₂O₃·HCl·0.5Et₂O) C, H, N.

Example 15

1-(4-Acetamido-3,5-diiodobenzyl)-6,7-dihydroxy-1,2,3,4-tetrahydroisoquinoline Hydrobromide

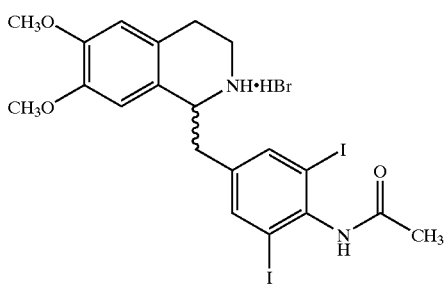

To a solution of 14 (0.50 g, 0.88 mmol) in dry CH₂Cl₂ (50 mL) at 0° C. (ice bath) was added dropwise 1M BBr₃ (4 mL, 4 mmol) in CH₂Cl₂ under an argon atmosphere. The mixture was then allowed to reach room temperature and stirring was continued overnight. The reaction mixture was cooled with an ice bath and methanol (20 mL) was added carefully. The solution was stirred for 10 minutes then evaporated in vacuo. This was repeated four times to give a solid which was stirred with ether overnight. The crude product was collected by filtration and recrystallized from methanol and ethyl ether to give 0.51 g (90%) of the desired product as an off-white solid: mp 202–206 (dec) ° C.; ¹H NMR (DMSO-D₆) δ9.82 (s, 1H, CONH), 9.15 (bm, 1H, OH), 8.91 (bm, 2H, NH⁺), 8.55 (bm, 1H, OH), 7.97 (s, 1H, ArH), 7.94 (s, 1H, ArH), 6.71 (s, 1H, ArH), 6.56 (s, 1H, ArH), 4.66 (bm, 1H, CH), 3.27–3.35 (m, 2H, CH), 3.10–3.16 (m, 2H, CH), 2.70–2.93 (m, 4H, CH), 2.02 (s, 3H, Me); ¹³C NMR (CD₃OD) δ172.51 (C=O), 147.04 and 145.89 (C-6 and C-7), 142.34 (C₄'), 141.90 and 141.73 (C-2' and C-6'), 140.18 (C-1'), 123.67 and 123.09 (C-4a and C-8a), 116.32 (C-5), 114.11 (C-8), 100.61 and 100.46 (C-3' and C-5'), 57.51 (C-1), 41.10 (C-3), 39.31 (CH₂Ar), 25.70 (C-4) 23.09 (COCH₃); IR (KBr) 1652 (CO), 1524 (C—N) cm⁻¹; MS m/e (m+): 565 (M+H, FAB). Anal. (C₁₈H₁₈N₂O₃I₂·HBr·0.25 Et₂O) C, H, N.

Example 16
1-(4-Diacetamido-3,5-diiodobenzyl)-6,7-dimethoxy-2-trifluoroacetyl-1,2,3,4-tetrahydroisoquinoline

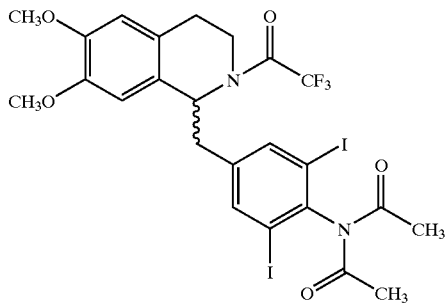

A solution of 10a (0.70 g, 1.08 mmol) in acetic anhydride (10 mL) was heated at reflux for 2 h. The solvent was evaporated in vacuo to give an oily residue. The residue was taken up in hot ethanol. The product crystallized upon cooling to give 0.78 g (99%) of the product as white crystals: mp 190–192° C.; $^1$H NMR (CDCl$_3$) 7.70 (s, 2H, ArH), 6.64 (s, 1H, ArH), 6.39(s, 1H, ArH), 5.53 (t, J=6.7 Hz, 1H, CH), 3.96 (m, 1H, CH), 3.87 (s, 3H, OMe), 3.79 (s, 3H, OMe), 2.68 (m, 1H, CH), 2.94–3.07 (m, 3H, CH), 2.77 (m, 1H, CH), 2.28 (s, 6H, Ac); $^{13}$C NMR (CDCl$_3$) δ71.23, 155.93 (q), 148.48, 147.86, 142.66, 141.36, 141.12, 125.65, 124.83, 116.31 (q), 111.14 109.88, 99.21, 56.08, 55.93, 55.31, 40.58, 40.44 (q), 28.43, 26.60; IR (KBr) 1719, 1683 (C=O), 1235, 1207 (C—O) cm$^{-1}$. Anal. (C$_{24}$H$_{23}$F$_3$I$_2$N$_2$O$_5$) C, H, N.

Example 17
6,7-Dihydroxy-1-(4-hydroxy-3,5-diiodobenzyl)-1,2,3,4-tetrahydroisoquinoline Hydrobromide

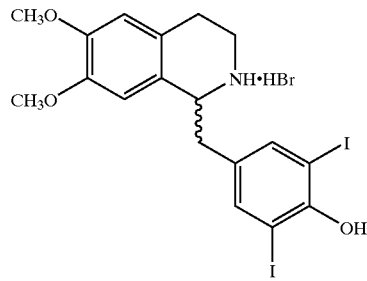

Hydrochloride 17[10] (0.21 g, 0.28 mmol) was dissolved in CHCl$_3$ and washed with 1N NaOH, organic layer was separated, washed with water and dried over MgSO$_4$. The solution was filtered, evaporated and dried under vacuum. The residue was dissolved in CH$_2$Cl$_2$ (4 mL) and 1M BBr$_3$ in CH$_2$Cl$_2$ (1.39 mL, 1.39 mmol) was added at −78° C. under argon atmosphere. The mixture was stirred overnight at room temperature followed by MeOH (1 mL) was added and stirred for 5 h. The resulting solution was evaporated with MeOH 5 times and the residue was recrystallized from MeOH-ether to give 0.078 g (45%) of white crystals: mp 235–237° C. (dec.); $^1$H NMR (DMSO-D$_6$) δ9.50 (s, 1H, OH), 9.14 (s, 1H, OH), 8.89 (s, 1H, OH), 8.78 (br. s, 1H, NH$^+$), 8.43 (br. s, 1H, NH$^+$), 7.76 (s, 2H, ArH), 6.64 (s, 1H, ArH), 6.55 (s, 1H, ArH), 4.55 (m, 1H, CH), 3.40–3.05 (m, 3H, CH), 2.92–2.68 (m, 3H, CH); $^{13}$C NMR (CD$_3$OD) δ156.59 (C-4'), 146.96 and 145.85 (C-6 and C-7), 141.69 (C-2' and C-6'), 132.30 (C-1'), 123.71 and 123.24 (C-4a and C-8a), 116.25 (C-5), 114.14 (C-8), 85.85 (C-3' and C-5'), 57.55 (C-1), 41.08 (C-3), 39.12 (CH$_2$Ar), 25.68 (C4); IR (KBr) 3600–2600 (OH, NH), 1527 (C=C, Ar) cm$^{-1}$. Anal. (C$_{16}$H$_{15}$I$_2$NO$_3$·HBr·0.1Et$_2$O) C, H, N.

Example 18
1-(3,5-Diiodobenzyl)-6,7-dimethoxy-2-trifluoroacetyl-1,2,3,4-tetrahydroisoquinoline

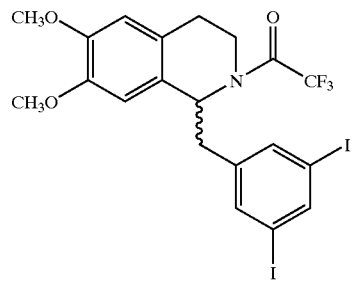

A solution of isoquinoline 10a (1.29 g, 2 mmol) in glacial acetic acid (30 mL) was added to a cold solution of NaNO$_2$ (0.19 g, 2.8 mmol) in concentrated (d 1.84) H$_2$SO$_4$ (3.4 mL), the temperature was kept within 0–5° C. The solution was poured into ice-water (60 g) and H$_3$PO$_2$ (12 ml) was added in 30 min. The cooling bath was removed and the solution was allowed to stand at room temperature for 2 days. The precipitate was filtered, dried and chromatographed on silica gel (hexane-AcOEt 8:1). Recrystallization from AcOEt-hexane gave 0.50 g (40%) of white crystals.: mp 162–163° C.; 1H NMR (CDCl$_3$) δ7.93 (t, J=1.5 Hz, 1H, ArH), 7.43 (d, J=1.5 Hz, 2H, ArH), 6.62 (s, 1H, ArH), 6.24 (s, 1H, ArH), 5.48 (t, J=6.7 Hz, 1H, CH), 3.95 (m, 1H, CH), 3.87 (s, 3H, OMe), 3.72 (s, 3H, OMe), 3.61 (m, 1H, CH), 3.06–2.86 (m, 3H, CH), 2.70 (m, 1H, CH); $^{13}$C NMR (CDCl$_3$) δ155.98 (q) 148.46, 147.67 143.60, 141.25, 137.98, 125.86, 125.00, 116.41 (q), 111.20, 110.19, 94.58, 55.96, 55.93, 55.37, 41.13 40.61 (q), 28.44; IR (KBr) 1686 (C=O), 1541, 1520 (C=C Ar) cm-1. Anal. (C$_{18}$H$_{19}$I$_2$NO$_2$) C, H, N.

Example 19
1-(3,4,5-Triiodobenzyl)-6,7-dimethoxy-2-trifluoroacetyl-1,2,3,4-tetrahydroisoquinoline

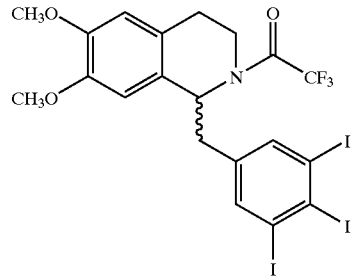

Compound 10a (1.29 g, 2 mmol) was diazotized in the usual manner. The resulting solution was poured in ice-water (60 g) followed by KI (0.47 g, 2.8 mmol) in water (10 mL) was added. The mixture was heated to 80° C. and allowed to cool. The precipitate was filtered, dried and purified by column chromatography (silica gel, hexane-AcOEt 3:1). Yield 0.51 g (34%): mp 215–216° C.; $^1$H NMR (CDCl$_3$) δ7.59 (s, 2H, ArH), 6.63 (s, 1H, ArH), 6.31 (s, 1H, ArH), 5.46 (t, J=6.7 Hz, 1H, ArH), 3.93 (m, 1H, CH), 3.88 (s, 3H, OMe), 3.75 (s, 3H, OMe), 3.61 (ddd, J=13.8, J=9.9, J=4.1 Hz, 1H, CH), 3.02–2.85 (m, 3H, CH$_2$Ar+CH), 2.70 (dt, J=16.2, J=4.3 Hz, 1H, CH); $^{13}$C NMR (CDCl$_3$) δ156.07 (q), 148.48, 147.71, 140.45, 139.90, 125.67, 125.08, 118.91, 116.39 (q), 111.16, 110.08, 106.78, 55.97, 55.10, 40.68 (q), 40.32 28.43; IR (KBr) 1685 (C=O), 1519 (C=C Ar) cm$^{-1}$. Anal. ($C_{20}H_{17}F_3I_3NO_3$) C, H, N.

Example 20

1-(3,5-Diiod benzyl)-6,7-dimethoxy-1,2,3,4-tetrahydroisoquinoline

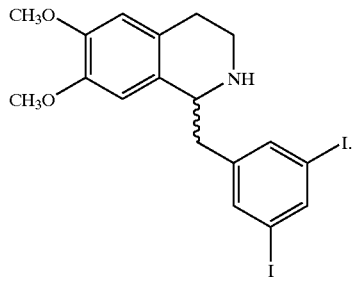

A mixture of isoquinoline 19a (0.38 g, 0.6 mmol) in MeOH (35 mL) and $K_2CO_3$ (0.85 g) in water (11 mL) were refluxed for 1.5 h. MeOH was evaporated and a white precipitate was filtered and dried. The crude product was purified by flash chromatography (silica gel) using a gradient (EtOAc-hexanes 1:2, EtOAc, EtOAc-MeOH 30:1) and recrystallized from EtOAc-hexanes to give 0.25 g (76%) of white crystals: mp 122–124° C.; $^1$H NMR (CDCl$_3$) δ7.94 (t, J=1.4 Hz, 1H, ArH), 7.60 (d, J=1.4 Hz, 2H, ArH), 6.60 (s, 1H, ArH), 6.57 (s, 1H, ArH), 4.10 (m, 1H, CH), 3.86 (s, 3H, OMe), 3.84 (s, 3H, OMe), 3.18 (m, 1H, CH), 3.08 (dd, J=4.1 and 13.7 Hz, 1H, CH), 2.95 (m, 1H, CH), 2.82–2.61 (m, 3H, CH); $^{13}$C NMR (CDCl$_3$) δ147.68, 147.17, 143.78, 143.15, 137.64, 129.86, 127.42, 111.98, 109.32, 94.99, 56.57, 56.06, 55.87, 42.20, 40.55, 29.39; IR (KBr) 3325 (NH), 1516 (C=C Ar) cm$^{-1}$ Anal. ($C_{18}H_{19}I_2NO_2$) C, H, N.

Example 21

6,7-Dimethoxy-1-(3,4,5-triiodobenzyl)-1,2,3,4-tetrahydroisoquinoline

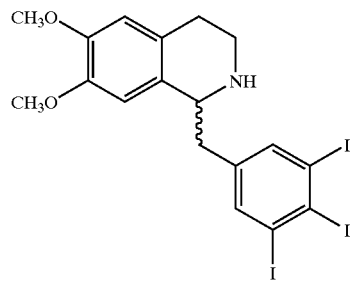

A mixture of isoquinoline 19b (0.454 g, 0.6 mmol) in MeOH (35 mL) and $K_2CO_3$ in water (11 mL) were refluxed for 1.5 h. MeOH was evaporated and a white precipitate was filtered and dried. Recrystallization from CHCl$_3$-hexane gave 0.300 g (76%) of white crystals: mp 168–170° C. (dec.); $^1$H NMR (CDCl$_3$) δ7.79 (s, 2H, ArH), 6.60 (s, 1H, ArH), 6.58 (s, 1H, ArH), 4.09 (dd, J=9.8, 3.8 Hz, 1H, CH), 3.86 (s, 3H, OMe), 3.85 (s, 3H, OMe), 3.17 (m, 1H, CH), 3.04–2.88 (m, 2H, CH), 2.82–2.60 (m, 3H, CH); $^{13}$C NMR (CDCl$_3$) δ147.66, 147.15, 143.00, 139.68, 129.67, 127.42, 118.18, 111.92, 109.14, 107.09, 56.35, 56.06, 55.85, 41.38, 40.56, 29.35; IR (KBr) 3312 (NH), 1516 (C=C Ar) cm$^{-1}$. Anal. ($C_{18}H_{18}I_3NO_2$) C, H, N.

Example 22

1-(4-Amino-3,5-diiodobenzyl)-6,7-dimethoxy-1,2,3,4-tetrahydroisoquinoline

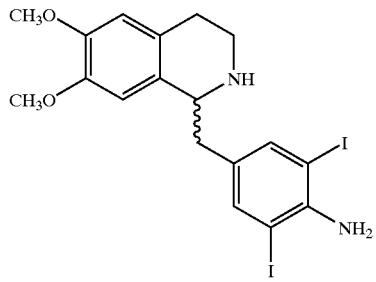

A slurry of the isoquinoline 10a (1.94 g, 3 mmol) in MeOH (260 mL) and $K_2CO_3$ (11.2 g) in $H_2O$ (80 mL) was refluxed for 1 h. MeOH was evaporated under reduced pressure, crystals filtered, dried and recrystallized from EtOAc-hexane to give the title compound (1.39 g, 84%): mp 169–171° C.; $^1$H NMR (CDCl$_3$) δ7.55 (s, 2H, ArH), 6.61 (s, 1H, ArH), 6.51 (s, 1H, ArH), 4.54 (s, 2H, NH$_2$), 4.04 (dd, J=9.6, 4.0 Hz, 1H, CH), 3.86 (s, 3H, OMe), 3.84 (s, 3H, OMe), 3.18 (m, 1H, CH), 3.03 (dd, J=13.8, 4.0 Hz, 1H, CH), 2.92 (ddd, J=12.1, 6.8, 5.2 Hz, 1H, CH), 2.82–2.61 (m, J=13.8, 9.6 Hz, 3H, CH); $^{13}$C NMR (CDCl$_3$) δ147.51, 147.05, 144.66, 139.97, 132.36, 130.14, 127.38, 111.88, 109.28, 81.59, 56.79, 56.01, 55.83, 40.87, 40.72, 29.47; IR (KBr) 3416 (NH), 3331 (NH), 1607 (NH bend), 1571, 1512 (C=C Ar) cm$^{-1}$. Anal. ($C_{18}H_{20}N_2I_2$) C, H, N.

Example 23

6,7-Dihydroxy-1-(3,5-diiodobenzyl)-1,2,3,4-tetrahydroisoquinoline Hydrobromide

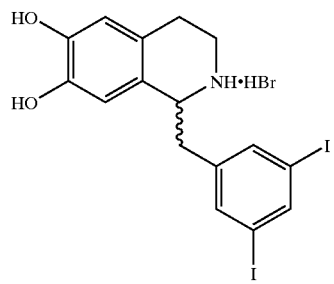

The isoquinoline 20a (0.19 g, 0.35 mmol) was demethylated using the same procedure as 15. Recrystallization from MeOH-ether gave 0.20 g (96%) of the title compound: mp 157–159° C. (dec.); $^1$H NMR (DMSO-D$_6$) δ9.13 (bs, 1H, OH), 8.88 (bm, 2H, NH+OH), 8.57 (bm, 1H, NH), 8.02 (t, J=1.4 Hz, 1H, ArH), 7.80 (d, J=1.4 Hz, 2H, ArH), 6.61 (s, 1H, ArH), 6.56 (s, 1H, ArH), 4.63 (bm, 1H, CH), 3.22–3.41 (m, 2H, CH), 3.14 (m, 1H, CH), 2.71–2.96 (m, 3H, CH); $^{13}$C NMR (CD$_3$OD) δ147.01 and 145.79 (C-6 and C-7), 145.69 (C-4'), 139.18 (C-2' and C-6'), 141.15 (C-1'), 123.76 and 123.03 (C-4a and C-8a), 116.30 (C-5), 114.21 (C-8), 96.14 (C-3' and C-5'), 57.25 (C-1), 41.02 (C-3), 40.08 (CH$_2$Ar), 25.60 (C-4); IR (KBr) 3600–2700 (br. OH, NH). 1617, 1521 (C=C Ar) cm$^{-1}$. Anal. ($C_{16}H_{15}BrI_3NO_2$) C, H, N.

Example 24

6,7-Dihydroxy-1-(3,4,5-triiodobenzyl)-1,2,3,4-tetrahydroisoquinoline Hydrobromide

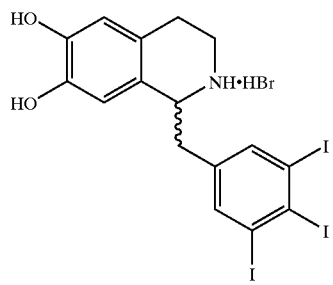

The isoquinoline 20b (0.23 g, 0.35 mmol) was demethylated using the same procedure as 15. Recrystallization from MeOH-ether gave 0.24 g (97%) of the title compound: mp 210–213° C. (dec.); $^1$H NMR (MeOH-D$_4$) δ7.92 (s, 2H, ArH), 6.63 (s, 1H, ArH), 6.56 (s, 1H, ArH), 4.64 (dd, J=5.7 and 3.1 Hz, 1H, CH), 3.3.42–3.53 (m, 1H, CH), 3.2–3.34 (m, 2H, CH), 2.83–3.07 (m, 3H, CH), $^{13}$C NMR (CD$_3$OD) δ147.11 and 145.90 (C-6 and C-7), 141.06 (C-2' and C-6'), 140.21 (C-1'), 123.70 and 122.98 (C-4a and C-8a), 120.90 (C-4'), 116.31 (C-5), 114.14 (C-8), 108.68 (C-3' and C-5'), 57.04 (C-1), 41.01 (C-3), 39.38 (CH$_2$Ar), 25.62 (C-4); IR (KBr) 3600–2700 (br. OH, NH). 1617, 1540 (C=C Ar) cm$^{-1}$. Anal. (C$_{16}$H$_{16}$BrI$_2$NO$_2$) C, H, N.

Example 25

1-(4-Amino-3,5-diiodobenzyl)-6,7-dihydroxy-1,2,3,4-tetrahydroisoquinoline Dihydrochloride

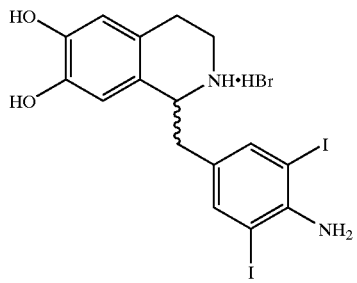

The isoquinoline 20c (1.21 g, 2.2 mmol) was demethylated in the same manner as 20b to give 1.14 g (76%) of the dihydrobromide salt: mp 155–157° C. (dec.). The product was dissolved in MeOH, chromatographed (silica gel, EtOAc-NH$_4$OH 100:1), evaporated with EtOH (×5). To an ethanol solution was added 1N etherial solution of HCl (3 mL), concentrated, precipitated with EtOAc and recrystallized from MeOH-i-PrOH: mp 176–178° C. (dec.); $^1$H NMR (DMSO-D$_6$) δ9.15 (br s, 1H, OH), 8.89 (br.s, 1H, NH$_2$$^+$), 7.68 (s, 2H, H-2'), 6.64 (s, 1H, H-5), 6.55 (s, 1H, H-8), 5.06 (br s, 2H, NH$_2$), 4.47 (m, 1H, H-1), 3.40–2.67 (m, 6H, H-3+H-4+CH$_2$Ar); $^{13}$C NMR (CD$_3$OD) δ147.99 (C-4'), 146.84 and 145.75 (C-6 and C-7), 141.60 (C-2' and C-6'), 128.78 (C-1'), 123.75 and 123.33 (C-4a and C-8a), 116.24 (C-5), 114.16 (C-8), 81.86 (C-3' and C-5'), 57.59 (C-1), 41.07 (C-3), 39.07 (CH$_2$Ar), 25.68 (C-4); IR (KBr) 3600–2500 (br, OH, NH), 1607 (NH bend), 1529 (C=C Ar) cm$^{-1}$. Anal. (C$_{16}$H$_{16}$I$_2$N$_2$O$_2$·2HCl·H$_2$O) C, H, N.

Example 26

1-(4-Acetamido-3-iodobenzyl)-6,7-dimethoxy-2-trifluoroacetyl-1,2,3,4-tetrahydroisoquinoline

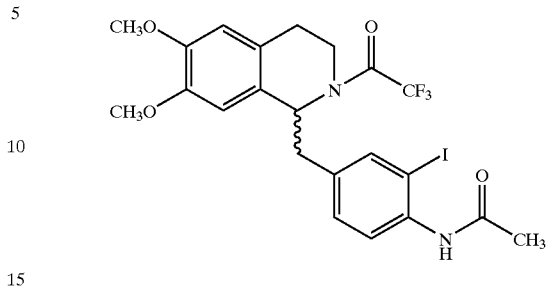

To a solution of isoquinoline 9a (0.52 g, 1 mmol) in hot benzene (15 mL) was added Ac$_2$O (0.51 g, 5 mmol). The solution was refluxed for 1 h. Reaction mixture was allowed to cool. A white crystals were filtered. Mother liquor was concentrated and hexane was added. Slightly creamy crystals were filtered, total yield 0.53 g (94%). To get analytical sample the compound was recrystallized from EtOAc-hexane: mp 174–175° C.; $^1$H NMR (CDCl$_3$) δ8.11 (d, J=8.3 Hz, 1H, H-5'), 7.52 (d, J=1.5 Hz, 1H, H-2'), 7.36 (s, 1H, NH), 7.10 (dd, J=8.3, 1.5 Hz, 1H, ArH), 6.60 (s, 1H, ArH), 6.32 (s, 1H, ArH), 5.23 (t, J=6.6 Hz, CH), 3.94 (m, 1H, CH), 3.87 (s, 3-H, OMe), 3,72 (s, 3-H, OMe), 3.54 (ddd, OMe=14.1, 10.4 Hz, 3.8 Hz, 1H, CH), 3.06 (m, 2H, CH), 2.90 (ddd, J=15.9 Hz, 10.4 Hz, 5.2 Hz, 1H, CH), 2.68 (dt, J=16.0, 4 Hz, 1H, CH), 2.23 (s, 3H, Ac); $^{13}$C NMR (CDCl$_3$) δ168.12, 155.90 (q), 148.30, 147.63, 139.63, 137.12, 134.95, 130.53, 126.19, 124.95, 121.73, 116.44 (q), 111.10, 110.17, 89.68, 55.91, 55.33, 40.75, 40.50 (q), 28.51, 24.75; IR (KBr) 3395 (NH), 1688 (C=O), 1519 (C=C Ar) cm$^{-1}$. Anal. (C$_{22}$H$_{22}$F$_3$IN$_2$O$_4$) C, H, N.

Example 27

1-(4-Acetamido-3-iodobenzyl)-6,7-dimethoxy-1,2,3,4-tetrahydroisoquinoline

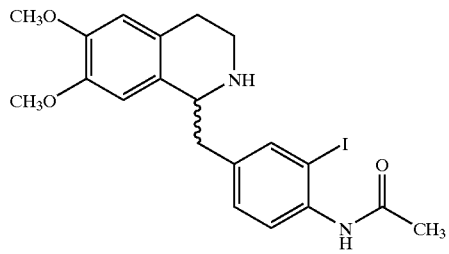

The title compound (0.57 g, 69%) as a glassy solid was obtained from the isoquinoline 22 (0.99 g, 1.76 mmol) in the same manner as 20c. $^1$H NMR (CDCl$_3$) δ8.12 (d, J=8.3 Hz, 1H, H-5'), 7.70 (d, J=1.7 Hz, 1H, ArH), 7.38 (s, 1H, NH), 7.26 (dd, J=8.3, 1.7 Hz, 1H, ArH), 6.63 (s, 1H, ArH), 6.60 (s, 1H, ArH), 4.11 (dd, J=9.6 Hz, 3.8, 1H, CH), 3.10–3.25 (m, 2H, CH), 2.92 (m, 1H, CH), 2.63–2.86 (m, 3H, CH$_2$Ar, CH), 2.25 (s, 3H, Ac); $^{13}$C NMR (CDCl$_3$) δ168.19, 147.54, 147.05, 139.31, 137.30, 136.66, 130.12, 129.92, 127.28, 122.25, 111.85, 109.27, 90.50, 56.64, 55.99, 55.79, 41.63, 40.61, 29.30, 24.66; IR (KBr) 3391 (NH), 1676 (C=O), 1515 (C=C Ar) cm$^{-1}$. Anal. (C$_{20}$H$_{23}$IN$_2$O$_3$) C, H, N.

Example 28
1-(4-Amino-3-iodobenzyl)-6,7-dihydroxy-1,2,3,4-tetrahydroisoquinoline Dihydrochloride

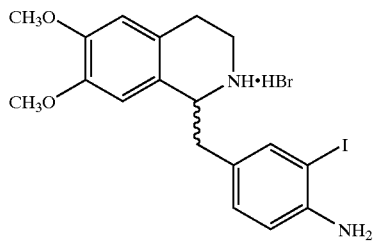

The title compound was obtained in the same manner as 21c from the isoquinoline 23 (0.42 g, 0.90 mmol). The product was recrystallized from MeOH (twice) to give 0.32 g (64%). The compound was dissolved in $NaHCO_3$ solution and extracted with EtOAc (×5). The solution was dried ($MgSO_4$) and evaporated. 1M HCl in ether (2 mL) was added to the methanol solution of the residue. The solution was concentrated and put in a refrigerator. The white crystals were filtered, washed with EtOAc and dried: dec.p. 186–190° C.; $^1$H NMR (DMSO-$D_6$) δ9.05 (bs, 1H, OH), 7.68 (d, J=1.7 Hz, 1H, ArH), 7.16 (dd, J=8.2 Hz, 1.7 Hz, 1H, ArH), 6.94 (d, J=8.2 Hz, 1H, ArH), 6.57 (s, 1H, ArH), 6.55 (s, 1H, ArH), 4.46 (m, 1H, CH), 3.27 (m, 1H, CH), 3.00–3.20 (m, 2H, CH), 2.80–3.00 (m, 2H, CH), 2.74 (dt, J=16.8 Hz, 5.9 Hz, CH); $^{13}$C NMR (CD$_3$OD) δ147.00 and 145.76 (C-6 and C-7), 1412.68 (C-2'), 138.21 (C-4'), 136.27 (C-1'), 132.35 (C-6), 123.82 and 123.10 (C-4a and C-8a), 116.27 (C-5), 114.33 (C-8), 124.24 (C-5'), 91.49 (C-3'), 57.27 (C-1), 40.90 (C-3), 39.87 (CH$_2$Ar), 25.659 (C-4); IR (KBr) 3600–2300 (br, OH, NH), 1607 (NH bend), 1526 (C=C Ar) cm$^{-1}$. Anal. ($C_{16}H_{17}IN_2O_2$·2HCl) C, H, N.

Example 29
1-(4-Acetamido-3-iodobenzyl)-6,7-dibenzyloxy-2-tert-butoxycarbonyl-1,2,3,4-tetrahydroisoquinoline

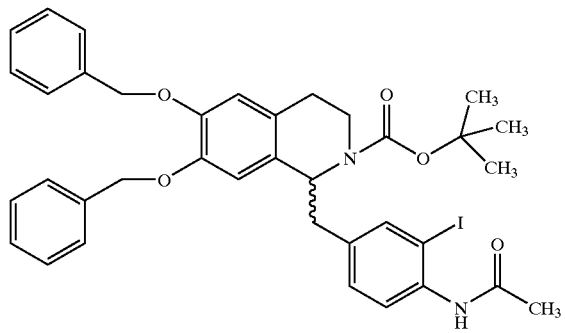

To a cold solution (0° C.) of isoquinoline 9b (0.68 g, 1 mmol) and Et$_3$N (0.34 g, 3 mmol) in CH$_2$Cl$_2$ (10 mL) was added AcCl (0.16 g, 2 mmol). The cooling bath was removed and the mixture was stirred overnight. The solution was washed with water (2×), dried over MgSO$_4$, filtered, evaporated. Ether was added and evaporated again to give glassy solid (0.65 g, 90%): mp 62–64° C.; $^1$H NMR (CDCl$_3$) δ(the spectrum consists of 2 rotamers of 5:3 ratio) 8.12 and 8.06 (d, J=8.2), 7.59–7.25 (m, 11H, ArH), 7.06 and 6.98 (m, 1H, ArH), 6.70 and 6.65 (s, 1H, ArH), 6.48 and 6.35 (s, 1H, ArH), 5.24–4.87 (m, 5H, CH$_2$O +CH), 4.12 and 3.73 (m, 1H, CH), 3.27–3.11 (m, 1H, CH), 2.98–2.60 (m, 3H, CH$_2$Ar+ CH), 2.60–2.37 (m, 1H, CH), 2.22 (s, 3H, Ac), 1.43 and 1.31 (s, 9H, t-Bu); IR (KBr) 3389 (NH), 1688 (C=O), 1512 (C=C Ar) cm$^{-1}$. Anal. ($C_{37}H_{39}IN_2O_5$) C, H, N.

Example 30
1-(4-Benzoylamino-3-iodobenzyl)-6,7-dibenzyloxy-2-tert-butoxycarbonyl-1,2,3,4-tetrahydroisoquinoline

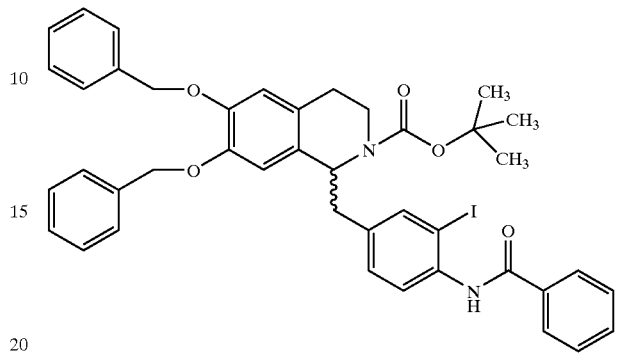

To a cold solution (0° C.) of isoquinoline 9b (0.68 g, 1 mmol) and Et$_3$N (0.30 g, 3 mmol) in 10 mL of CH$_2$Cl$_2$ was added benzoyl chloride (0.28 g, 2 mmol), the cooling bath was removed and the mixture was stirred overnight. CH$_2$Cl$_2$ was added (30 mL), the solution was washed with water, dried over MgSO$_4$, filtered and evaporated till dryness. The oily residue was dissolved in ether and evaporated to give 0.60 g (76%) of a glassy solid. The compound was purified by column chromatography (silica gel, EtOAc-hexane 1:2): mp 151–153° C.; $^1$H NMR (CDCl$_3$) δ8.42–6.36 (m, 18H, Ar), 5.20–4.90 (m, 5H, 2×CH$_2$O+H-1), 4.20–2.15 (m, 6H, aliphatic), 1.56–1.25 (m, 9H, t-Bu); IR (KBr) 3397 (NH), 1687 (C=O), 1513 (C=C Ar) cm$^{-1}$. Anal. ($C_{42}H_{41}IN_2O_5$) C, H, N.

Example 31
1-(4-Acetamido-3-iodobenzyl)-6,7-dihydroxy-1,2,3,4-tetrahydroisoquinoline Hydroiodide

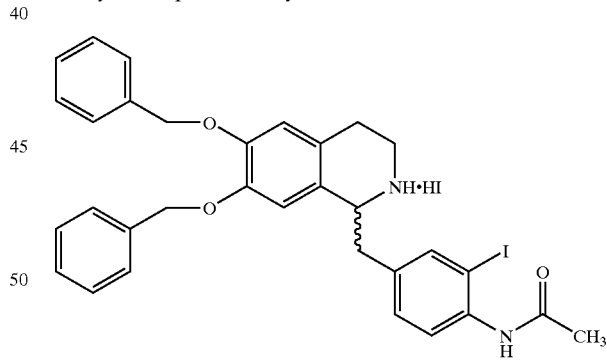

To a solution of isoquinoline 25a (0.40 g, 0.5 mmol) in anhydrous MeCN (5 mL) was added TMSI (0.40 g, 2 mmol) via syringe in argon atmosphere. The solution was stirred for 6 h followed by MeOH (1 mL) was added and stirring continued for 30 min. CH$_2$Cl$_2$ (30 mL) was added to reaction mixture and yellow crystals were filtered, yield 0.19 g (67%). The compound was dissolved in MeOH, AcOEt was added and the solution was concentrated under reduced pressure. The crystals were filtered: dec.p. 172–174° C.; $^1$H NMR (DMSO-D6) δ9.39 (s, 1H, NH), 8.86 (bs, 1H, OH), 8.50 (bs, 1H, OH), 7.90 (d, J=1.7 Hz, 1H, ArH), 7.41 (d, J=8.2 Hz, 1H, ArH), 7.35 (dd, J=8.2, 1.7 Hz, 1H, ArH), 6.63 (s, 1H, ArH), 6.56 (s, 1H, ArH), 4.63 (m, 1H, CH), 3.43–2.70

(m, 6H, CH), 2.06 (s, 3H, Ac); $^{13}$C NMR (CD$_3$OD) δ172.65 (C=O), 146.98 and 145.81(C-6 and C-7), 142.68 (C-2'), 140.11 (C-4'), 137.15 (C-1'), 131.30 (C-6'), 129.10 (C-5'), 123.63 and 123.27 (C-4a and C-8a), 116.27 (C-5), 114.15 (C-8), 91.49 (C-3'), 57.60 (C-1), 41.01 (C-3), 39.98 (CH$_2$Ar), 25.68 (C-4), 23.09 (COC̲H$_3$); IR (KBr) 3600–2400 (br, OH, NH), 1655 (C=O), 1624 (NH bend), 1522 (C=C Ar) cm$^{-1}$; MS m/z (m+): 439. Anal. (C$_{18}$H$_{19}$IN$_2$O$_3$.HI.0.25 EtOAc) C, H, N.

Example 32

1-(4-Benzoylamino-3-iodobenzyl)-6,7-dihydroxy-1,2,3,4-tetrahydroisoquinoline Hydroiodide

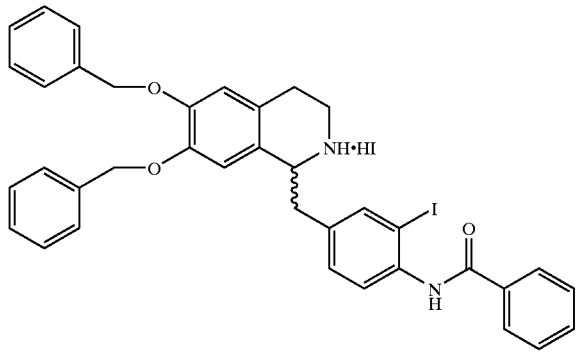

To a mixture of isoquinoline 25b (0.16 g, 2 mmol) in MeCN (4 mL) was added TMSI (0.16 g, 0.8 mmol) under argon atmosphere and the solution was stirred at room temperature for 7 h. MeOH (1 mL) was added, stirred for 1 h followed by ether (40 mL) was added and the yellow precipitate was filtered to give 0.10 g (80%) of the product. The compound was dissolved in MeOH, EtOAc was added and concentrated until the beginning of crystallization: mp 185–188° C. (dec.); $^1$H NMR (DMSO-D6) δ9.98 (s, 1H, NH̲COPh), 9.18 (s, 1H, NH), 8.88 (br, 2H, OH+NH), 8.54 (br, 1H, OH), 8.03–7.93 (m, 3H, ArH), 7.64–7.42 (m, 3H, ArH), 7.49 (d, J=8.1 Hz, 1H, ArH), 7.41 (dd, J=8.1, 1.4 Hz, 1H, ArH), 6.65 (s, 1H, ArH), 6.58 (s, 1H, ArH), 3.43–2.70 (m, 6H, CH; IR (KBr) 3500–2700 (br, NH, OH), 1649 (C=O), 1518 (C=C Ar) cm$^{-1}$. Anal. (C$_{23}$H$_{21}$IN$_2$O$_3$.HI.0.33 EtOAc) C, H, N.

Example 33

1-(3,5-Bis-trifluoromethylbenzyl)-6,7-dihydroxy-1,2,3,4-tetrahydroisoquinoline Hydrochloride

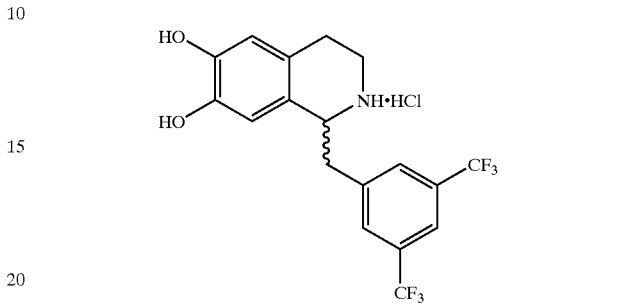

The title compound was obtained from 6c in the same manner as 15. The product was converted to the hydrochloride salt and recrystallization from methanol-ether gave the product as white crystals: mp 239–242° C.; $^1$H NMR (CD$_3$OD-D$_4$) δ7.95 (s, 3H, ArH), 6.65 (s, 1H, ArH), 6.44 (s, 1H, ArH), 4.77 (t, J=7.7 Hz), 3.51 (dt, J=6.88, 12.74 Hz), 3.33 (m, 2H, CH), 3.0 (m, 2H, CH), $^{13}$C NMR (CD$_3$OD) δ147.15 and 145.81 (C-6 and C-7), 140.21 (C-1'), 133.21 (C-3' and C-5'), 131.61 (C-2' and C-6'), 124.79 (CF$_3$), 123.79 and 122.63 (C-4a and C-8a), 122.58 (C-4'), 116.40 (C-5), 114.35 (C-8), 57.11 (C-1), 41.77 (C-3), 40.55 (CH$_2$Ar), 25.56 (C-4); IR (KBr) 3420 (NH), 1282 (C—O) cm$^{-1}$; Anal. (C$_{18}$H$_{16}$ClF$_6$NO$_2$) C, H, N.

Example 34

The compounds of the foregoing examples 1 to 33 were subjected to elemental analysis to further support the structural determinations. The results are summarized in Table I:

TABLE I

Elemental Analyses

| Example | Calculated, % | | | | Found, % | | |
|---|---|---|---|---|---|---|---|
| | C | H | N | Formula | C | H | N |
| 5a | 62.78 | 5.85 | 8.13 | C$_{18}$H$_{20}$N$_2$O$_5$ | 62.62 | 5.84 | 8.05 |
| 5c | 55.17 | 4.40 | 3.22 | C$_{20}$H$_{13}$F$_6$NO$_3$ | 55.10 | 4.41 | 3.20 |
| 6a | 65.84 | 6.14 | 8.53 | C$_{18}$H$_{20}$N$_2$O$_4$ | 65.19 | 6.17 | 8.46 |
| 6c | 51.68 | 4.55 | 3.01 | C$_{20}$H$_{19}$F$_6$NO$_2$.HCl.0.5H$_2$O | 51.70 | 4.53 | 2.99 |
| 7a | 56.60 | 4.51 | 6.60 | C$_{20}$H$_{19}$F$_3$N$_2$O$_5$ | 56.59 | 4.52 | 6.66 |
| 7b | 64.47 | 6.59 | 6.54 | C$_{23}$H$_{28}$N$_2$O$_6$ | 64.57 | 6.66 | 6.48 |
| 7c | 72.40 | 6.25 | 4.82 | C$_{35}$H$_{36}$N$_2$O$_6$ | 72.32 | 6.26 | 4.79 |
| 8a | 60.91 | 5.37 | 7.10 | C$_{20}$H$_{21}$F$_3$BN$_2$O$_3$ | 60.97 | 5.39 | 7.18 |
| 8b | 69.32 | 7.59 | 7.03 | C$_{23}$H$_{30}$N$_2$O$_4$ | 69.21 | 7.61 | 7.05 |
| 8c | 76.34 | 6.96 | 5.09 | C$_{35}$H$_{38}$N$_2$O$_4$ | 76.22 | 6.98 | 5.03 |
| 9a | 46.17 | 3.87 | 5.38 | C$_{20}$H$_{20}$F$_3$IN$_2$O$_3$ | 46.40 | 3.90 | 5.32 |
| 9b | 52.68 | 5.57 | 5.34 | C$_{23}$H$_{29}$IN$_2$O$_4$ | 52.61 | 5.56 | 5.25 |
| 9c | 62.13 | 5.51 | 4.14 | C$_{35}$H$_{37}$IN$_2$O$_4$ | 62.05 | 5.50 | 4.04 |
| 10a | 37.18 | 2.96 | 4.34 | C$_{20}$H$_{19}$F$_3$N$_2$O$_3$ | 37.45 | 3.05 | 4.32 |
| 11 | 37.29 | 2.66 | 4.35 | C$_{40}$H$_{34}$F$_6$I$_4$N$_4$O$_6$ | 37.65 | 2.77 | 4.34 |
| 12 | 39.44 | 3.31 | 5.11 | C$_{36}$H$_{34}$I$_4$N$_4$O$_4$ | 39.58 | 3.30 | 5.09 |
| 13 | 38.40 | 3.08 | 4.07 | C$_{22}$H$_{21}$F$_3$I$_2$N$_2$O$_4$ | 38.50 | 3.27 | 4.05 |
| 14 | 39.69 | 4.24 | 4.21 | C$_{20}$H$_{22}$I$_2$N$_2$O$_3$.HCl.0.5Et$_2$O | 39.64 | 3.94 | 4.44 |
| 15 | 34.36 | 3.25 | 4.23 | C$_{18}$H$_{18}$I$_2$N$_2$O$_3$.HBr.0.25Et$_2$O | 34.27 | 3.34 | 4.23 |
| 16 | 39.47 | 3.17 | 3.84 | C$_{24}$H$_{23}$F$_3$I$_2$N$_2$O$_5$ | 39.41 | 3.18 | 3.85 |
| 18 | 32.22 | 2.80 | 2.29 | C$_{16}$H$_{15}$I$_2$NO$_3$.HBr.0.1Et$_2$O | 32.30 | 2.76 | 2.33 |

TABLE I-continued

Elemental Analyses

| Example | Calculated, % | | | Formula | Found, % | | |
|---|---|---|---|---|---|---|---|
| | C | H | N | | C | H | N |
| 19a | 38.06 | 2.87 | 2.22 | $C_{20}H_{18}F_3I_2NO_3$ | 38.11 | 2.93 | 2.21 |
| 19b | 31.73 | 2.26 | 1.85 | $C_{20}H_{17}F_3I_3NO_3$ | 31.87 | 2.32 | 1.84 |
| 20a | 40.40 | 3.58 | 2.62 | $C_{18}H_{19}I_2NO_2$ | 40.52 | 3.65 | 2.59 |
| 20b | 32.70 | 2.74 | 2.12 | $C_{18}H_{18}I_3NO_2$ | 32.58 | 2.73 | 2.05 |
| 20c | 39.30 | 3.66 | 5.09 | $C_{18}H_{20}I_2N_2O_2$ | 39.56 | 3.73 | 5.00 |
| 21a | 32.68 | 2.74 | 2.38 | $C_{16}H_{15}I_2NO_2$·HBr | 32.77 | 2.78 | 2.33 |
| 21b | 26.22 | 2.12 | 1.96 | $C_{16}H_{14}I_3NO_2$·HBr | 27.06 | 2.19 | 1.91 |
| 21c | 31.35 | 3.29 | 4.57 | $C_{16}H_{16}I_2N_2O_2$·2HCl·$H_2O$ | 31.49 | 3.19 | 4.35 |
| 22 | 48.99 | 4.11 | 4.76 | $C_{22}H_{22}F_3IN_2O_4$·0.33PhH | 49.05 | 4.10 | 4.72 |
| 23 | 51.51 | 4.97 | 6.01 | $C_{20}H_{23}IN_2O_3$ | 51.73 | 5.00 | 5.98 |
| 24 | 40.96 | 4.08 | 5.97 | $C_{16}H_{17}IN_2O_2$·2HCl | 41.04 | 4.13 | 5.94 |
| 25a | 61.84 | 5.47 | 3.90 | $C_{37}H_{39}IN_2O_5$ | 61.91 | 5.46 | 3.94 |
| 25b | 64.26 | 5.29 | 3.59 | $C_{42}H_{41}IN_2O_5$ | 64.71 | 5.32 | 3.67 |
| 26a | 38.80 | 3.77 | 4.76 | $C_{18}H_{19}IN_2O_3$·0.25EtOAc | 38.65 | 3.87 | 4.57 |
| 26b | 44.44 | 3.78 | 4.26 | $C_{23}H_{22}IN_2O_3$·0.33EtOAc | 44.68 | 3.79 | 4.40 |

Thiazolopyridine Derivatives

2-Amino-4-(2-phthalimidoethyl)thiazole Hydrobromide (13). To a solution of 12 (2.08 g, 7.0 mmol) in acetone (45 ml) was added a solution of thiourea (0.535 g, 7.0 mmol) in acetone (25 ml) with rapid rate at room temperature. Just after the addition was complete, a precipitate appeared, the suspension was stirred overnight at room temperature and filtered to afford 2.45 g (98.5%) of 13 as a colorless powder: m.p. 258–260° C. (dec) (lit. 195° C. (dec starting point)); $^1$H NMR (DMSO-$d_6$), 2.82 (t, J=6.3 Hz, 2H), 3.83 (t, J=6.2 Hz, 2H), 6.56 (s, 1H), 7.81–7.88 (m, 4H), 9.01 (bs, 2H); IR (KBr) 3214, 3092, 1767, 1721, 1633, 1573, 1402 cm$^{-1}$. Anal. ($C_{13}H_{12}N_3O_2SBr$): C, H, N.

N-2-(2'-amino-4'-thiazolyl)ethyl-3,4,5-trimethoxyphenylacetamide (17). (a) To a suspension of 3,4,5-trimethoxyphenylacetic acid (4.52 g, 0.02 mol) in dry benzene (200 ml) was added dropwise oxalyl chloride (20 ml, 0.23 mol) at 0° C. After the addition was complete, the reaction mixture was stirred at room temperature until a clear solution was obtained (about 1 h). The solution was then heated at reflux for 2.5 h. The reaction mixture was cooled to room temperature and evaporated to give a yellow oil. It was dissolved in benzene (~50 ml) and evaporated again (repeated for two more times). 4.9 g (100%) of the acid chloride was obtained as a viscous yellow oil after dried in vacuo. $^1$H NMR (CDCl$_3$), δ3.83 (s, 3H), 3.84 (s, 6H), 4.05 (s, 2H), 6.45 (s, 2H); IR (neat) 300, 2941, 2840, 1799, 1593 cm$^{-1}$. (b) To a well-stirred suspension of 14 (976 mg, 3.2 mmol), NaOH (512 mg, 12.8 mmol) in CHCl$_3$ (7 ml) and H$_2$O (5 ml) was added slowly a solution of above-obtained 3,4,5-trimethoxyphenylacetyl chloride (784 mg, 3.2 mmol) in CHCl$_3$ (6 ml) at room temperature. After the addition was complete, the reaction mixture was stirred vigorously at room temperature for 1.5 h. The CHCl$_3$ layer was separated and the H$_2$O layer was extracted with CHCl$_3$. The combined organics were dried over anhydrous Na$_2$SO$_4$, and concentrated under reduced pressure. The oily residue was dissolved in CHCl$_3$ (40 ml), and to which HCl (1.0 M solution in dry Et$_2$O) (10 ml) was added at 0° C. The whole mixture was concentrated, the oily residue was dissolved in H$_2$O (10 ml). The aqueous solution was washed successively with EtOAc, Et$_2$O, CHCl$_3$ and basified with 20% NaOH. The product was extracted with CHCl$_3$, the combined organics were washed with brine, dried over anhydrous Na$_2$SO$_4$ and concentrated, the resulting solid residue was crystallized from EtOAc to afford 803 mg (71.4%) of 17 as a colorless crystal: m.p. 148–149.5° C.; $^1$H NMR (CDCl$_3$, δ2.57 (t, J=6.2 Hz, 2H), 3.42 (q, J=5.8 Hz, 2H), 3.46 (s, 2H), 3.79 (s, 3H), 3.80 (s, 6H), 5.16 (bs, 2H), 5.96 (s, 1H), 6.43 (s, 2H), 6.50 (bs, 1H); $^{13}$C NMR (CDCl$_3$), δ30.64, 38.88, 44.08, 56.11, 60.78, 103.10, 106.78, 130.53, 136.90, 150.07, 153.29, 167.89, 170.71; IR (KBr) 3433, 3266, 3080, 2939, 1646, 1624, 1590 cm$^{-1}$. Anal. ($C_{16}H_{21}N_3SO_4$): C, H, N.

2-Amino-4-(3',4',5'-trimethoxyphenylmethyl)-4,5,6,7-tetrahydrothiazolo[5,4-c]pyridine Dihydrochloride (7). A mixture of 17 (70.3 mg, 0.2 mmol) and phosphorus oxychloride (0.27 ml, 2.9 mmol) in CH$_3$CN (4 ml) was stirred and heated at reflux for 5 h. After the reaction mixture was cooled and concentrated under reduced pressure, the residue was dissolved in MeOH (2 ml) and the solution was heated at reflux for 30 min. After evaporation, the residue was dissolved in MeOH and evaporated again (repeated three more times). To the stirred solution of the resulting residue in MeOH (10 ml) was added NaBH$_4$ (757 mg, 20 mmol) in portions cautiously at 0° C. After the addition was complete, the reaction mixture was stirred overnight at room temperature. After the reaction mixture was evaporated to dryness under reduced pressure, the residue was dissolved in H$_2$O (5 ml), cooled with an ice-water bath and was basified with 20% NaOH. The basic solution was extracted with EtOAc, the combined organics were washed with brine, dried over anhydrous Na$_2$SO$_4$ and concentrated to give a viscous yellow oil. The oily residue was dissolved in CHCl$_3$ (5 ml), and to which HCl (1.0 M solution in dry Et$_2$O) (2 ml) was added at 0° C. The precipitate was filtered off and washed successively with Et$_2$O, EtOAc, CHCl$_3$ and crystallized from MeOH-Et$_2$O to afford 36.5 mg (44.7%) of 7 as a pale yellow powder: m.p. 230–231° C. (dec); $^1$H NMR (DMSO-$d_6$), δ2.71–2.90 (m, 2H), 2.96–3.03 (m, 1H), 3.17–3.23 (m, 3H), 3.64 (s, 3H), 3.75 (s, 6H), 4.77 (bs, 1H), 6.67 (s, 2H), 8.48 (bs, 1H), 9.68 (bs, 1H), 9.85 (bs, 1H); $^{13}$C NMR (CD$_3$OD), δ21.78, 39.79, 41.02, 54.83, 56.84, 61.17, 108.31, 112.94, 130.73, 133.85, 139.15, 155.19, 171.53; IR (KBr) 3392, 2940, 2839, 2771, 1632, 1593 cm$^{-1}$. Anal. ($C_{16}H_{23}N_3SO_3Cl_2$·0.5H$_2$O): C, H, N.

N-2-(2'-Amino-4'-thiazolyl)ethyl-3,5-diiodo-4-methoxyphenylacet-amide (18). In the same manner as 17, the title compound was prepared from 14 (590.3 mg, 1.94 mmol) and 3,5-diiodo-4-methoxyphenylacetyl chloride (844.8 mg, 1.94 mmol) which in turn was obtained by treating its corresponding acid[36] with oxalyl chloride as described above for 3,4,5-trimethoxyphenylacetic acid. Recrystallization from EtOAc gave 642.8 mg (61.0%) of 18 as a colorless crystal: m.p. 175–176° C.; $^1$H NMR (CD$_3$OD), δ2.63 (t, J=6.8 Hz, 2H), 3.35 (s, 2H), 3.41 (t, J=6.8 Hz, 2H), 3.79 (s, 3H), 6.05 (t, J=0.8 Hz, 1H), 7.72 (s, 2H); $^{13}$C NMR (CD$_3$OD), δ31.87, 39.72, 41.80, 61.14, 90.93, 103.35, 137.10, 141.64, 149.90,159.38, 171.47, 172.89; IR (KBr) 3431, 3272, 3083, 2933, 1643, 1623, 1579, 1524 cm$^{-1}$. Anal. (C$_{14}$H$_{15}$N$_3$SO$_2$I$_2$): C, H, N.

2-Amino-4-(3',5'-diiodo-4'-methoxyphenylmethyl)-4,5,6,7-tetrahydrothiazolo[5,4-c]pyridine Dihydrochloride (9). In the same manner as 7, the title compound was prepared from 18 (380.1 mg, 0.7 mmol). After flash column chromatography on silica gel, eluting with MeOH/CHCl$_3$ (1:30), 72 mg (19.5%) of the free base form of the product was obtained as a white solid, it was treated with HCl (1.0 M solution in dry Et$_2$O) to afford 9 as a pale yellow solid: m.p. 201–203° C. (dec); $^1$H NMR (DMSO-d$_6$), δ2.67–2.77 (m, 2H), 3.02–3.11 (m, 2H), 3.15–3.35 (m, 2H), 3.74 (s, 3H), 4.74 (bs, 1H), 7.90 (s, 2H), 8.31 (bs, 2H), 9.59 (bs, 1H), 9.79 (bs, 1H); $^{13}$C NMR, δ22.45, 38.02, 41.48, 54.86, 61.21, 91.85, 112.55, 135.12, 135.46, 142.57, 160.65, 171.36; IR (KBr) 3421, 2964, 2937, 2775, 1628, 1577 cm$^{-1}$. Anal. (C$_{14}$H$_{17}$N$_3$SOCl$_2$I$_2$): C, H, N.

N-2-(2'-Acetamido4'-thiazolyl)ethyl-3,5-diiodo-4-methoxyphenylacetamide (19). To a stirred suspension of 18 (434.5 mg, 0.8 mmol) in dry CH$_3$CN (1.8 ml) was added dropwise a solution of acetic anhydride (o.16 ml, 1.7 mmol) in dry benzene (0.6 ml). After the addition was complete, the reaction mixture was heated at reflux for 2.5 h. After the reaction mixture was cooled to room temperature and concentrated under reduced pressure to remove solvents completely, H$_2$O (5 ml) was added to the residue and the mixture was basified with saturated NaHCO$_3$ aqueous solution to pH 7.5–8.0. The solid material was filtered off and crystallized from CH$_3$CN to afford 430 mg (91.8%) of 19 as a colorless crystal: m.p. 231–232° C.; $^1$H NMR(DMSO-d$_6$), δ2.10 (s, 3H), 2.69 (t, J=7.0 Hz, 2H), 3.29–3.32 (m, 4 H), 3.71 (s, 3H), 6.70 (s, 1H), 7.67 (s, 2H), 8.08 (t, J=5.4 Hz, 1H), 12.04 (s, 1H); $^{13}$C NMR (DMSO-d$_6$), δ22.45, 31.09, 38.17, 40.12, 60.23, 90.94, 107.97, 136.65, 139.93, 148.29, 156.96, 157.52, 168.19, 169.32; IR (KBr) 3429, 3273, 3062, 1644, 1554, 1537 cm$^{-1}$. Anal. (C$_{16}$H$_{17}$N$_3$SO$_3$I$_2$): C, H, N.

2-Acetamido-4-(3',5'-diiodo-4'-methoxyphenylmethyl)-4,5,6,7-tetrahydrothiazolo[5,4-c]pyridine Maleate (10). In the same manner as 7, the title compound was prepared from 19 (300 mg, 0.51 mmol). After flash column chromatography on silica gel, eluting with acetone/hexane (1:3), 150 mg (51.7%) of the free base form of 10 was obtained as a white powder: m.p. 170–172° C.; $^1$H NMR (DMSO-d$_6$), δ2.09 (s, 3H), 2.53–2.60 (m, 2H), 2.66–2.73 (m, 1H), 2.77–2.86 (m, 1H), 2.89–2.95 (m, 1H), 3.09–3.15 (m, 1H), 3.72 (s, 3H), 4.12–4.13 (m, 1H), 7.80 (s, 2H), 11.91 (bs, 1H); $^{13}$C NMR (DMSO-d$_6$), δ22.45, 27.03, 40.41, 40.82, 53.87, 60.22, 90.86, 124.18, 139.29, 140.43, 143.70, 155.49, 156.72, 167.99; IR (KBr) 3428, 3252, 2914, 1675, 1636, 1565. Anal. (C$_{16}$H$_{17}$N$_3$SO$_2$I$_2$): C, H, N. 10 was obtained as a white powder by treating the above-obtained free base with maleic acid in CH$_3$CN: m.p. 121° C. (dec); $^1$H NMR (CD$_3$OD), δ2.18 (s, 3H), 2.93–3.09 (m, 4H), 3.38–3.44 (m, 1H), 3.63–3.71 (m, 1H), 4.93–4.96 (m, 1H), 6.26 (s, 8/3H), 7.85 (s, 2H); $^{13}$C NMR (DMSO-d$_6$), δ22.40, 23.37, 37.73, 40.42, 53.73, 60.26, 91.59, 118.22, 134.71, 135.43, 140.67, 142.07, 157.45, 157.78, 167.07, 168.60; IR (KBr) 3436, 3049, 2968, 2946, 1700, 1686, 1624, 1571 cm$^{-1}$. Anal. (C$_{16}$H$_{17}$N$_3$SO$_2$I$_2$.4/3C$_4$H$_4$O$_4$.1/3Et$_2$O): C, H, N.

2-Amino-5-(2-phthalimidoethyl)thiazole Hydrobromide (27). In the same manner as 13, the title compound was prepared from thiourea (2.75 g, 36.1 mmol) and 26[32] (crude, 10.69 g, 36.1 mmol). Recrystallization from MeOH/EtOH (1:10) gave 6.19 g (46% based on aldehyde 25[32]) of 27 as colorless plates: m.p. 244–246° C. (dec) (lit.[32] 180° C. (dec starting point)); $^1$H NMR (DMSO-d$_6$), δ2.96 (t, J=6.2 Hz, 2H), 3.77 (t, J=6.3 Hz, 2H), 7.08 (s, 1H), 7.82–7.89 (m, 4H), 9.01 (bs, 2H); IR (KBr) 3308, 3222, 3108, 2975, 1764, 1711, 1618, 1608, 1554, 1402 cm$^{-1}$. Anal. (C$_{13}$H$_{12}$N$_3$O$_2$SBr): C, H, N.

N-2-(2'-Amino-5'-thiazolyl)ethyl-3,4,5-trimethoxyphenylacetamide (21), In the same manner as 17, the title compound was prepared from 20[32] (1.95 g, 6.4 mmol) and 3,4,5-trimethoxyphenylacetyl chloride (1.57 g, 6.4 mmol). Recrystallization from CHCl$_3$/hexanes gave 1.42 g (63.3%) of 21 as colorless crystals: m.p. 121–122° C.; $^1$H NMR (CDCl$_3$), δ2.74 (t, J=6.0 Hz, 2H), 3.34 (q, J=6.3 Hz, 2H), 3.43 (s, 2H), 3.79 (d, 9H), 5.22 (bs, 2H), 5.78 (t, J=5.6 Hz, 1H), 6.39 (s, 2H), 6.59 (s, 1H); $^{13}$C NMR (CDCl$_3$), δ26.84, 40.39, 43.99, 56.07, 60.78, 106.35, 124.42, 130.29, 135.80, 137.09, 153.48, 167.34, 170.90; IR (KBr) 3294, 3114, 2995, 2936, 1654, 1636, 1588 cm$^{-1}$. Anal. (C$_{16}$H$_{21}$N$_3$SO$_4$): C, H, N.

N-2-(2'-Amino-5'-thiazolyl)ethyl-3,4,5-trimethoxyphenethylamine Dihydrochloride (24). To a suspension of 21(176 mg, 0.5 mmol) in dry THF (0.5 ml) was added dropwise slowly BH$_3$.THF(1.0 M in THF, 3.5 ml). After the addition was complete, the reaction mixture was stirred at room temperature for 30 min, and then was heated at reflux for 1 h. The reaction mixture was cooled to room temperature and treated cautiously with 10% HCl aqueous solution (3 ml), and the solution was heated at reflux for 30 min. After removal of THF, H$_2$O (10 ml) was added to the residue. The acidic solution was basified with 10% NaOH aqueous solution at 0° C. The product was extracted with CHCl$_3$ (20, 20, 10 ml), the combined organic was washed with brine (20 ml), and dried over anhydrous Na$_2$SO$_4$. After filtration and evaporation, a viscous oil was obtained, it was dissolved in CHCl$_3$ (8 ml) and was treated with HCl (1.0 M in dry Et$_2$O). The whole mixture was evaporated to dryness and the resulting white solid was crystallized in MeOH/Et$_2$O to give 109 mg (53.1%) of 24 as white crystals: m.p. 235° C. (dec); $^1$H NMR (CD$_3$OD), δ2.98–3.03 (m, 2H), 3.11–3.16 (m, 2H), 3.29–3.34(m, 4H), 3.72 (s, 3H), 3.84 (s, 6H), 6.63 (s, 2H), 7.18 (s, 1H); $^{13}$C NMR (CD$_3$OD), δ24.63, 33.53, 48.38, 50.25, 56.73, 61.07, 107.24, 121.73, 125.27, 133.76, 138.28, 154.87, 172.01; IR (KBr) 3427, 2947, 2767, 1630, 1590 cm$^{-1}$. Anal. (C$_{16}$H$_{25}$N$_3$SO$_3$Cl$_2$): C, H, N.

Radoiligand Binding Studies with β$_1$ Adrenoreceptors, β$_2$ Adrenoreceptors and β$_3$-Adrenoreceptors Expressed in CHO Cells Competitive and comparative binding experiments on β$_1$ Adrenoreceptors,.β$_2$ Adrenoreceptors and β$_3$-Adrenoreceptors expressed in CHO cells were performed as described previously. Fraundorfer, P. F.; Fertel, R. H.; Miller, D. D.; Feller, D. R. "Biochemical and pharmacological characterization of high-affinity trimetoquinol analogs on guinea pig and human beta adrenergic receptor subtypes: evidence for partial agonism." *J Pharmacol Exp Ther* 1994, 270, 665–74. ("Fraundorfer II", supra) CHO cells expressing human β$_1$ Adrenoreceptors, β$_2$ Adrenoreceptors and β$_3$-Adrenoreceptors (provided by A. D. Strosberg, Institut Cochin de Genetique Moleculaire, Paris, France; and David Bylund, University of Nebraska, Omaha, Nebr.; respectively) were cultured in Ham's F-12 medium supplemented with 10% fetal bovine serum, 50 U/mL-50 μg/mL of penicillin-streptomycin, 2 mM L-glutamine and 50 μg/mL of Geneticin in a humidified atmosphere of 5% CO$_2$-95% air. CHO cells grown to a confluence in 150-mL flasks were detached into Ham's F-12 medium after treatment with 0.05% trypsin-0.53 mM EDTA solution. The cells were then pelleted and washed three times with Tris-EDTA buffer (50 mM Tris-HCl, 150 mM NaCl, 20 mM EDTA, pH 7.4) and resuspended in the same buffer.

Data are expressed as the means±SE of the given number of experiments. All concentration-response and competition binding curves were analyzed using GraphPad Prism (GraphPad Software, San Diego, Calif., USA). $pK_{act}$ values are expressed relative to the maximal effect for each compound or effect at the highest concentration tested (for compounds with limited solubility). Relative efficacies ($e_π$) were calculated from plots of fractional percent occupancy versus response (% increase in cAMP accumulation) as described by Furchgott and Bursztyn (1967). The relative efficacies are expressed relative to (−)-isoproterenol, a reference β-adrenoceptor agonist.

Competition binding experiments were performed in duplicates using these whole cells. Aliquots (150 μL) of cells were added to tubes containing 50 μL of [$^{125}$I]ICYP (1.5–5× $10^4$ cells/20–60 pM of ICYP) and varying concentrations of competing drugs. The final volume in each tube was 0.25 mL. Nonspecific binding (5–30%) was determined in the presence of 1 μM (±)-propranolol. Incubations were carried out for 60 min at 37° C. Binding reactions were terminated by rapid filtration through Whatman GF/B glass fiber filters on a Brandel model 12-R tissue harvester. Filters were washed twice with ice cold Tris-EDTA buffer to remove free ICYP. The filters were dried under tissue harvester vacuum and radioactivity was measured by gamma scintillation spectrometry (Beckman model 8000 gamma counter, Palo Alto, Calif.). Specific binding to β Adrenoreceptor sites in these cells varied from 94 to 100%

Thromboxane $A_2$/Prostaglandin $H_2$ (TP) Receptor Sites in Human Platelets

For binding experiments, human platelet rich plasma (PRP) was centrifuged and re-suspended in 50 mM Tris-saline buffer, pH 7.4. Shin, Y.; Romstedt, K. J.; Miller, D. D.; Feller, D. R. "Interactions of nonprostanoid trimetoquinol analogs with thromboxane $A_2$/prostaglandin $H_2$ receptors in human platelets, rat vascular endothelial cells and rat vascular smooth muscle cells." *J Pharmacol Exp Ther* 1993, 267, 1017–23. Platelets were incubated with 5 nM [$^3$H]SQ 29,548 in a final vol of 0.5 mL as described by Hedberg, A.; Hall, S.; Ogletree, M.; Harris, D.; Liu, E. "Characterization of [5–6$^3$H]SQ 29,548 as a high affinity ligand for thromboxane $A_2$/prostaglandin $H_2$ receptors in human platelets". *J. Pharmacol. Exp. Ther*. 1988, 245, 786–792. Unlabelled SQ 29,548 (50 μM) was used to determine nonspecific binding. Varying concentrations of each competing drug were used to quantify the inhibition of specific [$^3$H]SQ 29,548 binding. Samples were incubated 30 min at room temperature, and rapidly filtered by vacuum through Whatman GF/C glass fiber filters on a Brandel cell harvester and washed for 10 sec with ice cold TRIS-saline buffer. Filters were placed in plastic scintillation vials containing 10 mL of an emulsion-type scintillation mixture and radioactivity measured by liquid scintillation spectrometry. Specific binding to human platelets varied between 88 to 95%.

Competitive binding data were analyzed using the PC-version of the radioligand binding program LIGAND (McPherson, 1985). Inhibitory concentration-50 ($IC_{50}$) value of each competing drug was determined graphically from individual plots of percent radioligand bound versus log drug concentration on β-adrenoceptors and human platelets. According to the reported method (Cheng, Y.; Prusoff, W. H. Relationship between the inhibition constant ($K_i$) and the concentration of the inhibitor which causes 50 percent inhibition ($I_{50}$) of an enzymatic reaction, *Biochem. Pharmacol*. 1973, 22, 3099–3108), $K_i$ values were calculated from the obtained $IC_{50}$ values. Dissociation constants ($K_i$) for each competing drug were calculated using the equation:

$$K_i = \frac{IC_{50}}{\left(1 + \frac{L}{K_L}\right)}$$

and the data expressed as $pK_i$ (i.e., $-\log K_i$) values. The $K_L$ values used in the above equation are 17 pM, for $β_1$ Adrenoreceptor; 10 pM for $β_2$ Adrenoreceptor; 11 pM for $β_3$-Adrenoreceptor; and 3.1 nM for Thromboxane $A_2$/Prostaglandin $H_2$ receptors, respectively.

cAMP Radioimmunoassay (cAMP-RIA Assay). Chinese hamster ovary (CHO) cells expressing either human $β_1$-, $β_2$- or $β_3$-adrenoceptor (AR) subtypes were used as previously described (Fraundorfer, P. F.; Lezama, E. J.; Salazar-Bookaman, M. M.; Fertel, R. H.; Miller, D. D.; Feller, D. R. Isomeric-activity ratios of trimetoquinol enantiomers on β-adrenergic receptor subtypes: functional and biochemical studies, *Chirality* 1994, 6, 76–85). These cells were grown to confluence in 60 mm dishes, washed with Hank's balanced salt solution, and then incubated with Hank's balanced salt solution (pH 7.4) containing 20 mM HEPES and 1 mM 3-isobutyl-1-methylxanthine (IBMX) and 1 mM L-ascorbic acid for 30 min at 37° C. Varying concentrations ($10^{-11}$ to $10^{-4}$ M) of the drugs were added with an additional 30 min of incubation. After removal of the Hank's buffer, the cAMP generated within the cells was extracted by the addition of trichloroacetic acid (6% w/v). cAMP content was determined as the amount of [$^{125}$I]-labeled succinyl-cAMP tyrosine methyl ester/antibody precipitated, as described by Brooker et al. (Brooker, G.; Harper, J. F.; Terasaki, W. L.; Moylan, R. D. Radioimmunoassay of cyclic AMP and cyclic GMP. In *Advances in Cyclic Nucleotide Research*; Brooker, G., Greengard, P. and Robinson, A., Ed.; Raven Press: New York, 1979, pp 1–33). The precipitated protein was dissolved in 0.1N NaOH. Protein content was determined by the method of Lowry et al. (Lowry, O. H.; Rosebrough, N. J.; Farr, A. L.; Randall, R. J. Protein measurement with the Folin phenol reagent., *J. Biol. Chem*. 1951, 193, 265–275), using bovine serum albumin as the standard. Data are expressed as the means±SE of the given number of experiments. All concentration-response and competition binding curves were analyzed using GraphPad Prism (GraphPad Software, San Diego, Calif., USA). $pK_{act}$ values are expressed relative to the maximal effect for each compound or effect at the highest concentration tested (for compounds with limited solubility). Relative efficacies ($e_π$) were calculated from plots of fractional percent occupancy versus response (% increase in cAMP accumulation) as described by Furchgott and Bursztyn (Furchgott, R. F., and Bursztyn, P. "Comparison of dissociation constants and relative efficacies of selected agonists on parasympathetic receptors" *Ann. N.Y. Acad. Sci*. 1967, 882–889).

cAMP response element (CRE)-luciferase(LUC) reporter gene (CRE-LUC) assay. CHO cells stably expressing human $β_1$-, $β_2$-, or $β_3$-AR subtypes were transfected with a 6 CRE-LUC plasmid (gift from Dr. A. Himmler, Vienna, Austria) using electroporation with a single 70 ms, 150V pulse (Vansal, S. S.; Feller, D. R. Development of a rapid and efficient cyclic AMP assay for evaluating β-adrenergic receptor ligands., *Naunyn-Schmiedeberg's Arch. Pharmacol. Suppl*. 2 1998, 258, R659). The transfected CHO cells were seeded at a density of 40,000/well in 96 well microtiter plates (Culturplate, Packard) and allowed to grow for 20 hours. After 20 hours, the cells were treated with varying drug concentrations ($10^{-11}$ to $10^{-4}$ M) for 4 hours. Following drug exposures, the cells were lysed and luciferase activity measured using the LucLite® assay kit (Packard). Changes in light production were measured by a Topcount® luminometer (Packard).

Functional Activity of TMQ Analogs in Isolated Rat Tissues

Male Sprague Dawley rats (Harlan Industries, Cumberland, Ind.) housed under a 12 hour light/dark cycle and fed Purina Rodent Laboratory Chow (Ralston Purina., St. Louis, Mo.) and water ad libitum, were used for the studies. On the day of the experiment, the rats weighting 200–430 g were killed by cervical dislocation and tissues were quickly removed according to standard procedures (Staff of the Department of Pharmacology, University of Edinburg, in Pharmacological Experiments on Isolated Preparations, p. 104. Livingstone, London, 1968). Chronotopic responses of spontaneously beating right atria were used as a model for measuring $\beta_1$-AR mediated activity (Konkar, A. A., Fraundorfer, P. F., Fertel, R. H., Burkman, A. M., Miller, D. D., and Feller, D. R. "Pharmacological Activities of trimetoquinol and 1-benzyl halogen-substituted analogues on rat $\beta$-adrenoceptor subtypes. Eur. J. Pharmacol. 1996, 305, 63–71). Relaxations of spirally cut tracheal strips precontracted with $3\times10^{-7}$M carbachol, and of longitudinal segments of the esophageal smooth muscle precontracted with $10^{-6}$M carbachol (in the presence of 1 $\mu$M pindolol and 10 $\mu$M phentolamine), were used to measure $\beta_2$-and $\beta_3$-AR-mediated activity, respectively (Konkar, A. A., Fraundorfer, P. F., Fertel, R. H., Burkman, A. M., Miller, D. D., and Feller, D. R. "Pharmacological Activities of trimetoquinol and 1-benzyl halogen-substituted analogues on rat $\beta$-adrenoceptor subtypes. Eur. J. Pharmacol. 1996, 305, 63–71; Lezama, E. J., Konkar, A. A., Salazaar-Bookaman, M. M., Miller, D. D., and Feller, D. R. "Pharmacological study of atypical $\beta$-adrenoceptors in rat esophageal smooth muscle. Eur. J. Pharmacol., 1996, 308, 69–80). Contractions of spirally cut aortic strips and inhibition of phenylephrine-induced contraction of the tissue, were used to measure $\alpha$-AR mediated agonist or antagonist activity of the compounds respectively. The tissues were isolated and prepared for measurement of functional activity as per protocols described earlier (Konkar, A. A., Fraundorfer, P. F., Fertel, R. H., Burkman, A. M., Miller, D. D., and Feller, D. R. "Pharmacological Activities of trimetoquinol and 1-benzyl halogen-substituted analogues on rat $\beta$-adrenoceptor subtypes. Eur. J. Pharmacol. 1996, 305, 63–71; Staff of the Department of Pharmacology, University of Edinburg, in Pharmacological Experiments on Isolated Preparations, p. 104. Livingstone, London, 1968). All tissues were suspended and equilibrated in modified Kreb's buffer in water-jacketed baths at 37° C. Resting tensions of 1 g for right atria, trachea and aorta, and of 200 mg for esophageal smooth muscle were used. All tissue responses were measured on a Grass Polygraph Model 7C with a Grass FT-03C isometric force-displacement transducer. Cumulative concentration response curves for each drug were constructed by the method of van Rossum (van Rossum, J. M. "Cumulative dose-response curves. II. Technique for making of dose-response curves in isolated organs and the evaluation of drug parameters. Arch. Int. Pharmacodyn. 1963, 143, 299–300). Increasing concentrations of compounds were added every 2–3 min with (−)-isoproterenol and every 10–15 min with TMQ analogs, or until no further change in response was observed.

In the right atrium, the concentration response curve for (−)-isoproterenol was followed by complete washout of the drug, after which a curve for either acetamido- or chloroacetamido DITMQ was constructed. The tissue was again washed 6–7 times with 10 ml of buffer, followed by repeated washes every 10–15 min. Changes observed in the duration of chronotropic effect following repeated washes was used as an indicator of 'irreversible' binding of the compound to the atrial tissue. A second concentration response curve with (−)-isoproterenol was constructed in atria to determine desensitization effects.

The concentration response curves in trachea and esophagus culminated with a final concentration of $10^{-5}$M(−)-isoproterenol, to determine the maximal relations induced in the tissue and express functional responses of the TMQ analogs as a percentage of maximal (−)-isoproterenol-induced response. Carbachol-precontracted tissues were included as controls through the duration of relaxation studies.

Studies with aorta were performed in the presence of 1 $\mu$m pindolol, to block $\beta$-AR-mediated effects. Concentration response curves to phenylephrine were followed by washout of the drug 30 min incubation with $10^{-5}$ M acetamido- or chloroacetamido-DITMQ. A second phenylephrine concentration-response was then constructed to determine any $\alpha$-AR blocking activity of the TMQ analogs. In control experiments, second concentration response curves of phenylephrine were constructed in the absence of treatment with the compounds.

TABLE 1

Human $\beta_2$-Adrenoceptor Expressed in CHO Cells and Platelet Thromboxane $A_2$/Prostaglandin (TP) Receptor Binding Affinities of Trimetoquinol (TMQ) Analogs.

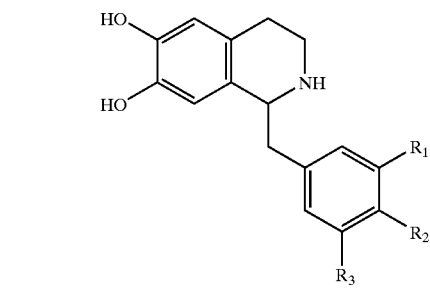

| | 1-Benzyl Substituents | | | Human $\beta_2$ Adrenoreceptor CHO[a] | | Human TP receptors[b] | |
|---|---|---|---|---|---|---|---|
| Compnd | $R_1$ | $R_2$ | $R_3$ | pKi ± SEM | P.R.[c] | pKi ± SEM | P.R.[c] |
| 1 | OCH$_3$ | OCH$_3$ | OCH$_3$ | 7.36 ± 0.23 | 1.0 | 6.79 ± 0.09 | 1.00 |
| 2 | I | OCH$_3$ | I | 8.69 ± 0.16 | 21 | 7.33 ± 0.07 | 3.5 |

TABLE 1-continued

Human β$_2$-Adrenoceptor Expressed in CHO Cells and Platelet Thromboxane A$_2$/Prostaglandin (TP) Receptor Binding Affinities of Trimetoquinol (TMQ) Analogs.

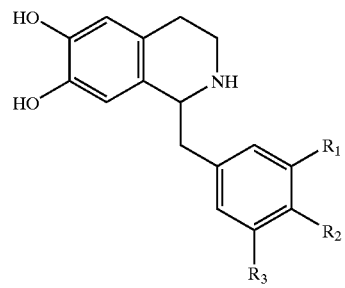

| Compnd | 1-Benzyl Substituents | | | Human β$_2$ Adrenoreceptor CHO[a] | | Human TP receptors[b] | |
|---|---|---|---|---|---|---|---|
| | R$_1$ | R$_2$ | R$_3$ | pKi ± SEM | P.R.[c] | pKi ± SEM | P.R.[c] |
| 21c | I | NH$_2$ | I | 8.81 ± 0.15 | 28 | 6.73 ± 0.12 | 0.87 |
| 24 | I | NH$_2$ | H | 8.19 ± 0.27 | 6.8 | 6.00 ± 0.02 | 0.16 |
| 15 | I | NHCOCH$_3$ | I | 8.06 ± 0.13 | 5.0 | 6.45 ± 0.11 | 0.46 |
| 26a | I | NHCOCH$_3$ | H | 8.11 ± 0.16 | 5.6 | 5.83 ± 0.14 | 0.11 |
| 21a | I | H | I | 9.52 ± 0.13 | 150 | 6.75 ± 0.07 | 0.91 |
| 21b | I | I | I | 8.82 ± 0.18 | 29 | 4.22 ± 0.03 | 0.003 |
| 26b | I | NHCOPh | H | 8.70 ± 0.03 | 22 | 5.27 ± 0.13 | 0.03 |
| 18 | I | OH | I | 7.93 ± 0.03 | 3.7 | 4.72 ± 0.09 | 0.009 |
| 27 | CF$_3$ | H | CF$_3$ | 5.36 ± 0.32 | 0.01 | 4.08 ± 0.02 | 0.002 |

[a]Using [$^{125}$I] ICYP as radioligand, N = 4–9
[b]Using [$^3$H] SQ 29,548 as radioligand, N = 4–9
[c]PR = potency ratio relative to cmpd. 1 (TMQ). PR = antilog [pKi(drug)-pKi(TMQ)]

TABLE 2

Selectivity of Trimetoquinol (TMQ) Analogs for Human β$_2$-and β$_1$-Adrenoceptors Expressed in CHO cells

| | pKi ± SEM | | |
|---|---|---|---|
| Compound | human β$_1$ CHO[a] | human β$_2$ CHO[a] | β$_2$/β$_1$ selectivity[b] |
| 1 | 6.49 ± 0.06 | 7.36 ± 0.23 | 7.4 |
| 2 | 7.10 ± 0.06 | 8.69 ± 0.16 | 39 |
| 21a | 6.74 ± 0.30 | 9.52 ± 0.13 | 600 |

[a]using [125[]] ICYP as radioligand for β$_1$-and β$_2$ Adrenoreceptor expressed in CHO cells, N = 4–9 bβ$_2$/β$_1$-selectivity = Ki (β$_1$ Adrenoreceptor)/Ki (β$_2$ Adrenoreceptor)

TABLE 3

Agonist Activities of (–)-Isoproterenol, AcetamidolDITMQ and Chloracetamido-DITMQ on β-Adrenoceptors in Isolated Rat Tissues.

| | Right Atria (β-AR) | Trachea | Esophageal Smooth Muscle (Atypical-β/β$_3$-AR) |
|---|---|---|---|
| (–)Isoproterenol | | | |
| pEC$_{50}$ | 8.95 ± 0.06 | 8.00 ± 0.05 | 7.34 ± 0.08 |
| I.A. | 1.00 | 1.00 | 1.00 |
| (n) | (5) | (8) | (12) |
| AcetamidoDITMQ (A-14) | | | |
| pEC$_{50}$ | 8.96 ± 0.04 | 9.22 ± 0.07† | 8.68 ± 0.12 |
| I.A. | 0.93 ± 0.04 | 0.84 ± 0.02† | 0.99 ± 0.03t |

TABLE 3-continued

Agonist Activities of (−)-Isoproterenol, AcetamidolDITMQ and Chloracetamido-DITMQ on β-Adrenoceptors in Isolated Rat Tissues.

| | Right Atria (β-AR) | Trachea | Esophageal Smooth Muscle (Atypical-β/β$_3$-AR) |
|---|---|---|---|
| (n) | (4) | (4) | (7) |
| ChloroacetamidoDITMQ | | | |
| (A-37) | | | |
| pEC$_{50}$ | 8.94 ± 0.07 | 8.90 ± 0.05† | 8.08 ± 0.03† |
| I.A. | 0.81 ± 0.05† | 0.83 ± 0.02† | 0.99 ± 0.01† |
| (n) | (4) | (4) | (6) |

Data are calculated as pEC$_{50}$ (-log EC$_{50}$, concentration required to produce a response equal to 50% of maximal response elected by the drug) and I.A. (Intrinsic activity, maximal drug-induced response relative to the maximal response elicited by (−)-isoproterenol). The values are mean ± SEM of the number of experiments indicated in parentheses. † Indicates significant difference in value of TMQ analog compared to corresponding value of (−)-isoproterenol ($P < 0.05$).

TABLE 4

| COMPOUND | pK$_i$ | pK$_{act}$ | E$_{max}$ |
|---|---|---|---|
| (−)Isoproterenol | 4.45 ± 0.06 (14) | 7.90 ± 0.12 (16) | 100 |
| BRL 37344 | 6.96 ± 0.08 (5) † | 8.90 ± 0.12 (9) † | 103.3 ± 6.80 |
| S(−)TMQ | 5.67 ± 0.03 (5) † | 8.19 ± 0.19 (7) | 87.65 ± 6.90 |
| (±)TMQ | 5.11 ± 0.12 (8) † | 8.69 ± 0.14 (10) † | 125.3 ± 9.20 |
| DITMQ (A-11) | 6.34 ± 0.03 (5) † | 9.40 ± 0.08 (9) † | 96.90 ± 10.10 |
| AminoDITMQ (A-35) | 6.14 ± 0.08 (5) † | nd | nd |
| AcetamidoDITMQ (A-14) | 7.28 ± 0.06 (5) † | 9.34 ± 0.12 (6) † | 89.57 ± 6.93 |
| ChloroacetamidoDITMQ (A-37) | 6.49 ± 0.05 (5) † | 9.05 ± 0.16 (6) † | 92.48 ± 6.59 |
| BromoacetamidoDITMQ (A-38) | 6.70 ± 0.05 (6) † | 9.36 ± 0.39 (5) † | 87.27 ± 12.21 |
| 6,7-Dimethoxy-acetamidoDITMQ | 4.84 ± 0.03 (5) † | nd | nd |
| 6,7-Dimethoxy TMQ | 3.88 ± 0.07 (4) † | no activity up to $3 \times 10^{-5}$ M M | |
| 6,7-Methylenedioxy TMQ | 4.29 ± 0.05 (5) | 5.92 ± 0.12 (8) † | 70.90 ± 4.41†* |
| DemethoxyDITMQ | 5.80 ± 0.03 (5) † | 8.74 ± 0.10 (4) † | 97.69 ± 5.85 |
| IsothiocyanatolTMQ (A-46) | 5.83 ± 0.12 (4) † | 8.61 ± 0.15 (4) † | 104.1 ± 7.10 |

Inhibition constants (-log K$_i$ or pK$_i$) for binding and functional activity constants (-log EC$_{50}$ or pK$_{act}$) for cAMP accumulation in CHO cells expressing rat-β$_3$-AR. E$_{max}$ is the maximal cAMP accumulation stimulated by the compounds relative to that of (−)-isoproterenol. Values are mean ± SEM of the number of experiments indicated in parentheses. nd = value not determined. †Indicates significant difference in value of TMQ analog compared to corresponding to value of (−)-isoproterenol ($P < 0.05$).

TABLE 5

Human β3-Adrenoceptors Binding Affinities of TMQ Analogs

| | pK, ± SEM[a] | | |
|---|---|---|---|
| | Human β$_1$-AR | Human β$_2$-AR | Human β$_3$-AR |
| ISO | 5.80 ± 0.07 | 6.17 ± 0.12 | 4.73 ± 0.25 |
| TMQ | 6.49 ± 0.06 | 7.36 ± 0.23 | 5.43 ± 0.28 |
| 8 (A-11) | 7.10 ± 0.06 | 8.69 ± 0.16 | 7.67 ± 0.24 |
| 7 (B-29) | 5.21 ± 0.08 | 6.21 ± 0.12 | 4.17 ± 0.05 |
| 9 (B-28) | 6.14 ± 0.08 | 6.37 ± 0.08 | 5.83 ± 0.15 |

[a]Human β$_1$-β$_2$- and β$_3$-AR were expressed in CHO cells. [$^{125}$I] ICYP was used as the radioligand. K$_i$ values were calculated using the following equation: K$_i$ (nM) = IC$_{50}$ (1 + [L]/K$_d$), wherein IC$_{50}$ is the concentration (nM) of an analog at which the radioligand binding was reduced by 50%; [L] is the radioligand concentration used; K$_d$ is the radioligand equilibrium dissociation constant.

pK$_i$ = −logK$_i$; SEM = standard error of mean. N = 3–9.

TABLE 6

Human β-Adrenoceptors (AR) Functional Activities of TMQ Analogs

| | Human β$_1$-AR | | Human β$_2$-AR | | Human β$_3$-AR | |
|---|---|---|---|---|---|---|
| | pK$_{act}$ ± SEM[a] | I.A. ± SEM[b] | pK$_{act}$ ± SEM | I.A. ± SEM | pK$_{act}$ ± SEM | I.A. ± SEM |
| A. cAMP-RIA ASSAY[c] | | | | | | |
| Iso | 8.75 ± 0.14 | 100 | 84.0 ± 0.17 | 100 | 7.37 ± 0.11 | 100 |
| TMQ | 8.70 ± 0.11 | 109 ± 10 | 8.33 ± 0.24[d] | 95 ± 3 | 8.60 ± 0.15 | 95 ± 3 |
| 8 (A-11) | 8.11 ± 0.13 | 103 ± 4 | 8.47 ± 0.12 | 56 ± 9 | 8.76 ± 0.2 | 120 ± 9 |
| 7 (B-29) | N.A.[e] | <10 | N.A. | 20 ± 1 | 5.06 ± 0.01 | 54 ± 1 |
| 9 (B-28) | N.A. | <5 | N.A. | <5 | 6.95 ± 0.11 | 67 ± 3 |
| 10 | N.A. | <10 | N.A. | <10 | N.A. | <10 |
| B. CRE-LUC assay[c] | | | | | | |
| 9 (B-28) | N.A. | <10 | N.A. | <15 | 6.71 ± 0.18 | 62 ± 3 |
| 24 | N.B. | <10 | N.A. | <10 | N.A. | <10 |

[a]Human β$_1$-, β$_2$- and β$_3$-AR were expressed in CHO cells.
K$_{act}$ is the molar drug concentration which produces a cAMP response equal to 50% of its maximal response, pK$_{act}$ = –logK$_{act}$.
[b]I.A. = Intrinsic Activity, expressed as the percentage of a maximal analog response relative to the maximal response (100%) of R-(–)-isoproterenol (ISO).
[c]see Experimental Section.
[d]Data is for S-(–)-TMQ isomer.
[e]N.A. '2 Not active at 100 µM.
Values are the mean ± SEM of N '2 4–12.

TABLE 7

Data on TMQ analogs using the CRE-LUC assay

| | β$_1$-AR | | | β$_2$-AR | | | β$_3$-AR | | |
|---|---|---|---|---|---|---|---|---|---|
| Compound | pK$_{act}$ ± SEM (n) | | I.A. | pk$_{act}$ ± SEM (n) | | I.A. | pK$_{act}$ ± SEM (n) | | I.A. |
| 6-Monophenolic TMQ analog (A-4) | 5.71 ± 0.13 (8) | | 58 | 6.64 ± 0.15 (8) | | 38 | 7.45 ± 0.09 (8) | | 90 |
| Non-catechol TMQ Analog (A-3) | N.D. (8) | | 22 | N.D. (8) | | 21 | 7.54 ± 0.22 (8) | | 62 |

Agonist potencies (pKact values) and intrinsic activities (IA) of noncatechol (A3) and 6-monophenolic (A4) analogs for human β-adrenoceptor subtypes expressed in Chinese hamster ovary cells.
IA values are expressed relative to the maximal response to (–)-isoproterenol in these CHO cell systems expressing the three human β-adrenoceptor subtypes.
Agonist activities were measured using the cyclic AMP response element-luciferase reporter gene (CRE-LUC) assay.

TABLE 8

Selectivity of TMQ Analogs for Human $\beta_1$, $\beta_2$, and $\beta_3$ Adrenoreceptors Expressed in CHO Cells and Functional Activities of TMQ Analogs in CHO Cells Expressing Human $\beta_3$ Adrenoreceptors.

| MOLECULAR STRUCTURE | h$\beta_3$ cAMP EC$_{50}$ (nM) +/− SEM | h$\beta_3$ cAMP % Iso +/− SEM | h$\beta_1$ Binding KI (nM) | h$\beta_2$ Binding ki (nM) |
|---|---|---|---|---|
| (structure 1) | 506 +/− 137 | 32.3 +/− 5 | 8400 +/− 8100 | 534 +/− 67 |
| (structure 2) | 45 +/− 9 | 81 +/− 3 | 14.2 +/− 9.8 | 24 +/− 9 |
| (structure 3) | <4 | 119 +/− 6 | 25 +/− 1.3 | 3.1 +/− 1.7 |
| (structure 4) | <4 | 108 +/− 2 | 63.4 +/− 0.9 | |
| (structure 5) | >3160 | | >3000 | >3000 |

TABLE 8-continued

Selectivity of TMQ Analogs for Human $\beta_1$, $\beta_2$, and $\beta_3$ Adrenoreceptors Expressed in CHO Cells and Functional Activities of TMQ Analogs in CHO Cells Expressing Human $\beta_3$ Adrenoreceptors.

| MOLECULAR STRUCTURE | h$\beta_3$ cAMP EC$_{50}$ (nM) +/− SEM | h$\beta_3$ cAMP % Iso +/− SEM | h$\beta_1$ Binding KI (nM) | h$\beta_2$ Binding ki (nM) |
|---|---|---|---|---|
| (structure with NH·HCl, OCH$_3$, I, I) | 33.5 +/− 7 | 89 +/− 5 | 278 +/− 59 | 47 +/− 4.3 |
| Trimetoquinol (structure with OMe, OMe, OMe) | >1 | 100 +/− 2 | 6.7 +/− 1.3 | 6.5 +/− 1.5 |

Conclusion

The invention has been described herein with regard to particular preferred operating circumstances and requirements, and in a particular context. Those of ordinary skill will clearly understand the application of the invention and its uses in other diverse circumstances and will, with the guidance provided herein, be able to adapt the invention to the particular requirements of other contexts of practice of the invention.

The foregoing description and disclosure of the present invention is intended to be illustrative for the guidance of those of ordinary skill in the art to which the invention pertains, and is not intended to define or limit the scope of the invention. The scope of the invention is defined and limited only in the appended claims.

What is claimed is:

1. A compound having the structure:

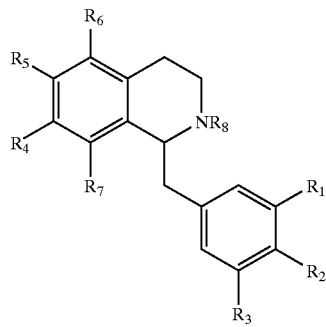

wherein:
$R_1$ and $R_3$ are independently selected from the group consisting of hydrogen, halogen, alkyl, aryl alkyl, CF$_3$, and OCH$_3$;

$R_2$ is selected from the group consisting of hydrogen, halogen, OH, OCH$_3$, OCH$_2$COOH, C(O)-aryl, NCS, NH$_2$, N$_3$, NHR$_8$, NHCH$_2$COOH, NHCOR$_{13}$, NHCONHR$_{13}$, and NHCOSR$_{13}$;

$R_4$ and $R_5$ are each independently selected from the group consisting of hydrogen, OH, and halogen;

$R_6$ and $R_7$ are each independently selected from the group consisting of hydrogen and halogen;

$R_8$ is selected from the group consisting of hydrogen, lower alkyl of from 1 to 8 carbons, halogen, OCH$_3$, and CF$_3$; and $R_{13}$ is selected from the group consisting of hydrogen, lower alkyl of from 1 to 8 carbons, phenyl, halogen, OCH$_3$, CF$_3$, and —CH$_2$R', wherein R' is halogen;

wherein no more than one of $R_1$, $R_2$, and $R_3$ is OCH$_3$ or hydrogen and one, but not both, of $R_4$ and $R_5$ is OH;

or a pharmaceutically acceptable salt thereof.

2. The compound of claim 1, wherein $R_4$ is OH and $R_5$ is hydrogen or halogen.

3. The compound of claim 1, wherein $R_5$ is OH and $R_4$ is hydrogen or halogen.

4. The compound of claim 1, wherein $R_6$ and $R_7$ are each halogen.

5. The compound of claim 1, wherein $R_6$ and $R_7$ are each hydrogen.

6. The compound of claim 1, wherein $R_2$ is OCH$_3$, NH$_2$, or NHCOR$_{13}$.

7. The compound of claim 1, wherein $R_1$ and $R_3$ are halogen.

8. The compound of claim 1, wherein $R_1$ is halogen, $R_2$ is $OCH_3$ or $NH_2$, and $R_3$ is hydrogen.

9. The compound of claim 1, wherein $R_5$ is OH, $R_4$ is hydrogen or halogen, $R_2$ is $OCH_3$, $NH_2$, or $NHCOR_{13}$, and $R_1$ and $R_3$ are halogen.

10. A pharmaceutical composition, comprising a pharmaceutically acceptable carrier and at least one compound having the structure:

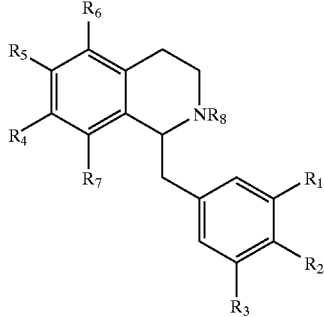

wherein:
$R_1$ and $R_3$ are independently selected from the group consisting of hydrogen, halogen, alkyl, aryl alkyl, $CF_3$, and $OCH_3$;
$R_2$ is selected from the group consisting of hydrogen, halogen, OH, $OCH_3$, $OCH_2COOH$, C(O)-aryl, NCS, $NH_2$, $N_3$, $NHR_8$, $NHCH_2COOH$, $NHCOR_{13}$, $NHCONHR_{13}$, and $NHCOSR_{13}$;
$R_4$ and $R_5$ are each independently selected from the group consisting of hydrogen, OH, and halogen;
$R_6$ and $R_7$ are each independently selected from the group consisting of hydrogen and halogen;
$R_8$ is selected from the group consisting of hydrogen, lower alkyl of from 1 to about 8 carbons, halogen, $OCH_3$, and $CF_3$; and
$R_{13}$ is selected from the group consisting of hydrogen, lower alkyl of from 1 to about 8 carbons, phenyl, halogen, $OCH_3$, $CF_3$, and $-CH_2R'$, wherein $R'$ is halogen;
wherein no more than one of $R_1$, $R_2$, and $R_3$ is $OCH_3$ or hydrogen and one, but not both, of $R_4$ and $R_5$ is OH;
or a pharmaceutically acceptable salt thereof.

11. The pharmaceutical composition of claim 10, wherein $R_4$ is OH and $R_5$ is hydrogen or halogen.

12. The pharmaceutical composition of claim 10, wherein $R_5$ is OH and $R_4$ is hydrogen or halogen.

13. The pharmaceutical composition of claim 10, wherein $R_6$ and $R_7$ are each halogen.

14. The pharmaceutical composition of claim 10, wherein $R_6$ and $R_7$ are each hydrogen.

15. The pharmaceutical composition of claim 10, wherein $R_2$ is $OCH_3$, $NH_2$, or $NHCOR_{13}$.

16. The pharmaceutical composition of claim 10, wherein $R_1$ and $R_3$ are halogen.

17. The pharmaceutical composition of claim 10, wherein $R_1$ is halogen, $R_2$ is $OCH_3$ or $NH_2$, and $R_3$ is hydrogen.

18. The pharmaceutical composition of claim 10, wherein $R_5$ is OH, $R_4$ is hydrogen or halogen, $R_2$ is $OCH_3$, $NH_2$, or $NHCOR_{13}$, and $R_1$ and $R_3$ are halogen.

19. A method of stimulating, regulating or modulating metabolism of fats in adipose tissue in animals, comprising administering an effective amount of at least one compound having the structure:

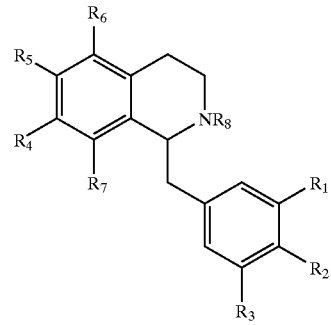

wherein:
$R_1$ and $R_3$ are independently selected from the group consisting of hydrogen, halogen, alkyl, aryl alkyl, $CF_3$, and $OCH_3$;
$R_2$ is selected from the group consisting of hydrogen, halogen, OH, $OCH_3$, $OCH_2COOH$, C(O)-aryl, NCS, $NH_2$, $N_3$, $NHR_8$, $NHCH_2COOH$, $NHCOR_{13}$, $NHCONHR_{13}$, and $NHCOSR_{13}$;
$R_4$ and $R_5$ are each independently selected from the group consisting of hydrogen, OH, and halogen;
$R_6$ and $R_7$ are each independently selected from the group consisting of hydrogen and halogen;
$R_8$ is selected from the group consisting of hydrogen, lower alkyl of from 1 to about 8 carbons, halogen, $OCH_3$, and $CF_3$; and
$R_{13}$ is selected from the group consisting of hydrogen, lower alkyl of from 1 to about 8 carbons, phenyl, halogen, $OCH_3$, $CF_3$, and $-CH_2R'$, wherein $R'$ is halogen;
wherein no more than one of $R_1$, $R_2$, and $R_3$ is $OCH_3$ or hydrogen and one, but not both, of $R_4$ and $R_5$ is OH;
or a pharmaceutically acceptable salt thereof.

20. The method of claim 19, wherein $R_4$ is OH and $R_5$ is hydrogen or halogen.

21. The method of claim 19, wherein $R_5$ is OH and $R_4$ is hydrogen or halogen.

22. The method of claim 19, wherein $R_6$ and $R_7$ are each halogen.

23. The method of claim 19, wherein $R_6$ and $R_7$ are each hydrogen.

24. The method of claim 19, wherein $R_2$ is $OCH_3$, $NH_2$, or $NHCOR_{13}$.

25. The method of claim 19, wherein $R_1$ and $R_3$ are halogen.

26. The method of claim 19, wherein $R_1$ is halogen, $R_2$ is $OCH_3$ or $NH_2$, and $R_3$ is hydrogen.

27. The method of claim 19, wherein the compound is administered with at least one pharmaceutically acceptable carrier.

28. The method of claim 19, wherein $R_5$ is OH, $R_4$ is hydrogen or halogen, $R_2$ is $OCH_3$, $NH_2$, or $NHCOR_{13}$, and $R_1$ and $R_3$ are halogen.

* * * * *